(12) United States Patent
Kawaura et al.

(10) Patent No.: US 10,206,674 B2
(45) Date of Patent: Feb. 19, 2019

(54) PUNCTURE DEVICE

(71) Applicant: TERUMO KABUSHIKI KAISHA, Shibuya-ku, Tokyo (JP)

(72) Inventors: Masakatsu Kawaura, Sunnyvale, CA (US); Nao Yokoi, Sunnyvale, CA (US); Shigeki Ariura, Ebina (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 457 days.

(21) Appl. No.: 14/869,712

(22) Filed: Sep. 29, 2015

(65) Prior Publication Data
US 2016/0089140 A1 Mar. 31, 2016

Related U.S. Application Data

(63) Continuation of application No. PCT/JP2013/059895, filed on Apr. 1, 2013.

(51) Int. Cl.
*A61B 17/06* (2006.01)
*A61B 17/34* (2006.01)
(Continued)

(52) U.S. Cl.
CPC .... *A61B 17/06109* (2013.01); *A61B 17/3403* (2013.01); *A61B 17/3468* (2013.01);
(Continued)

(58) Field of Classification Search
CPC .... A61B 17/06066; A61B 2017/00805; A61B 17/0482; A61B 17/06109; A61B 17/062;
(Continued)

(56) References Cited

U.S. PATENT DOCUMENTS

| 5,544,664 A | 8/1996 | Benderev et al. |
| 6,245,082 B1 | 6/2001 | Gellman et al. |

(Continued)

FOREIGN PATENT DOCUMENTS

| JP | 9-248306 A | 9/1997 |
| JP | 2001-511686 A | 8/2001 |

(Continued)

OTHER PUBLICATIONS

Extended European Search Report dated Nov. 4, 2016 by the European Patent Office in corresponding European Patent Application No. 13881239.1 (6 pages).

(Continued)

*Primary Examiner* — Kaylee R Wilson
(74) *Attorney, Agent, or Firm* — Buchanan Ingersoll & Rooney PC

(57) ABSTRACT

A puncture device is disclosed, which can include a puncture needle curved in an arc, turnably supported around an axis (J1) as a turning center, and having a needle tip which punctures a living body when the puncture needle is turned; a urethral insertion member having a urethral insertion portion of a linear shape which is inserted into the urethra; and a frame capable of connecting the puncture needle and the urethral insertion member to each other, the frame turnably supporting the puncture needle. When the puncture needle is turned, the needle tip of the puncture needle has a locus (plane f9), which is inclined by an inclination angle (θ2) of 20 to 60 degrees with respect to a plane (f2) orthogonal to the urethral insertion portion.

16 Claims, 49 Drawing Sheets

(51) Int. Cl.
    *A61M 1/00*         (2006.01)
    *A61F 2/00*          (2006.01)
    *A61B 17/04*        (2006.01)
    *A61B 17/00*        (2006.01)
    *A61B 17/42*        (2006.01)
    *A61B 90/00*        (2016.01)

(52) U.S. Cl.
    CPC ......... *A61F 2/0045* (2013.01); *A61M 1/0088* (2013.01); *A61B 17/0482* (2013.01); *A61B 17/06066* (2013.01); *A61B 17/42* (2013.01); *A61B 2017/00557* (2013.01); *A61B 2017/00566* (2013.01); *A61B 2017/00805* (2013.01); *A61B 2017/06042* (2013.01); *A61B 2017/06052* (2013.01); *A61B 2017/3405* (2013.01); *A61B 2090/0807* (2016.02); *A61F 2002/0072* (2013.01)

(58) Field of Classification Search
    CPC ...... A61B 17/3468; A61B 2017/06052; A61B 17/3403; A61B 17/42; A61F 2002/0072; A61F 2/0045; A61F 2/0063
    See application file for complete search history.

(56) References Cited

U.S. PATENT DOCUMENTS

| | | | | |
|---|---|---|---|---|
| 6,911,003 | B2 * | 6/2005 | Anderson | .......... A61B 17/0401 600/30 |
| 2003/0097038 | A1 | 5/2003 | Presthus et al. | |
| 2003/0171644 | A1 | 9/2003 | Anderson et al. | |
| 2004/0087970 | A1 | 5/2004 | Chu et al. | |
| 2006/0293554 | A1 | 12/2006 | Crawford | |
| 2007/0156012 | A1 * | 7/2007 | Tracey | ............... A61B 17/0625 600/30 |
| 2008/0242917 | A1 | 10/2008 | Kaladelfos | |
| 2009/0088599 | A1 | 4/2009 | Zook et al. | |
| 2009/0216250 | A1 | 8/2009 | Zipper | |
| 2013/0023725 | A1 | 1/2013 | Nose et al. | |
| 2015/0250573 | A1 | 9/2015 | Evans et al. | |

FOREIGN PATENT DOCUMENTS

| | | |
|---|---|---|
| JP | 2001-333911 A | 12/2001 |
| JP | 2005-509488 A | 4/2005 |
| JP | 2005-534422 A | 11/2005 |
| JP | 2010-012281 A | 1/2010 |
| JP | 2010-540121 A | 12/2010 |
| WO | WO 98/35606 A2 | 8/1998 |
| WO | WO 03/043536 A2 | 5/2003 |
| WO | WO 2004/012579 A2 | 2/2004 |
| WO | WO 2006/005117 A1 | 1/2006 |
| WO | WO 2009/042988 A2 | 4/2009 |
| WO | WO 2011/125947 A1 | 10/2011 |

OTHER PUBLICATIONS

International Search Report (PCT/ISA/210) dated Jun. 4, 2013, by the Japanese Patent Office as the International Searching Authority for International Application No. PCT/JP2013/059895.

* cited by examiner

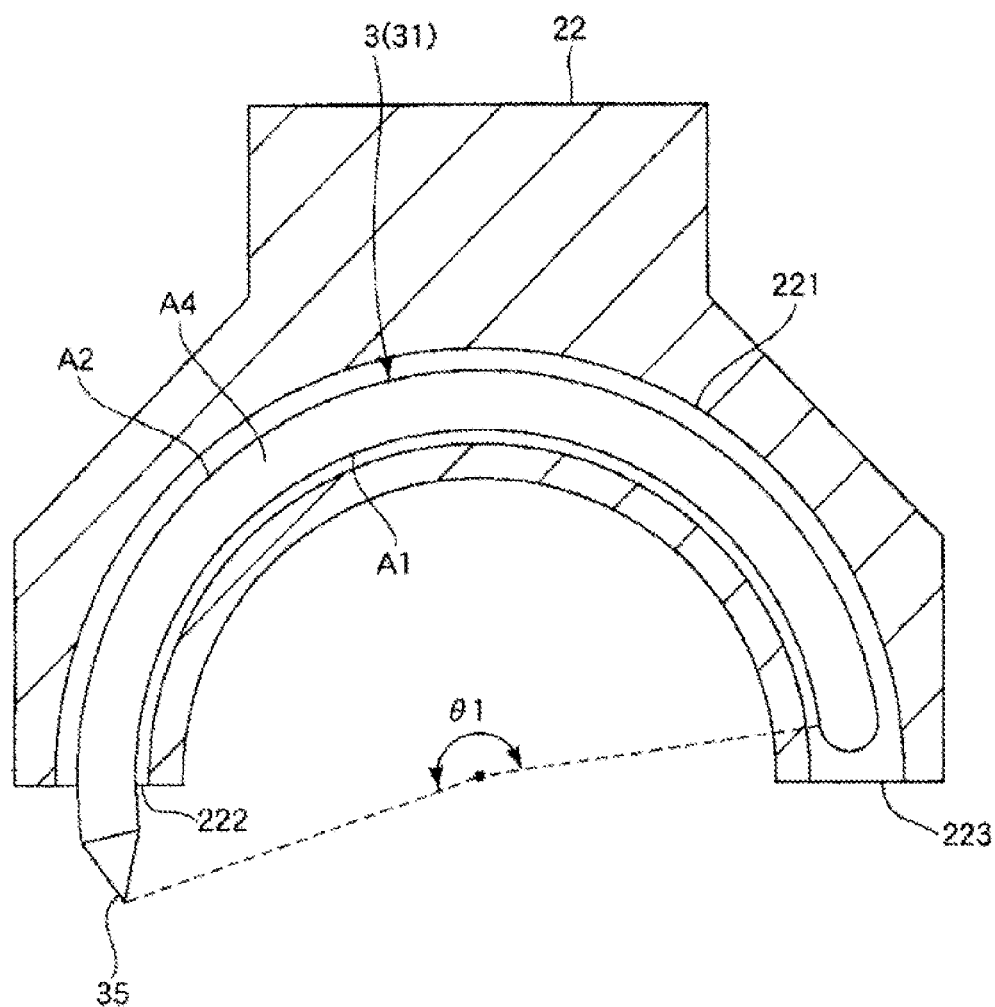
F I G . 5

F I G . 1 2 (a)
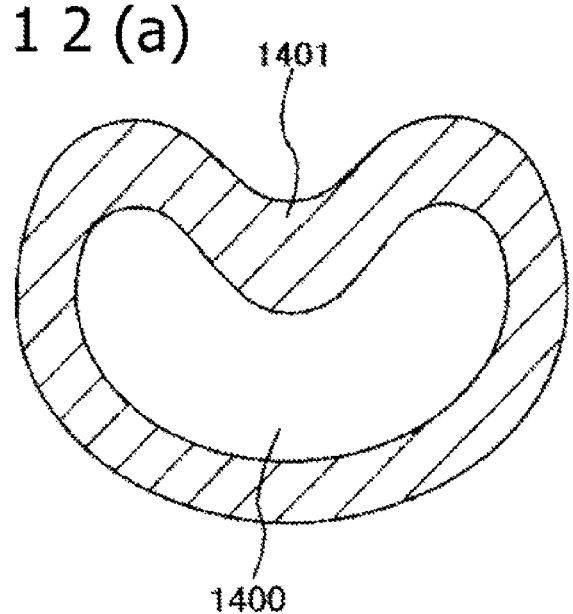
F I G . 1 2 (b)
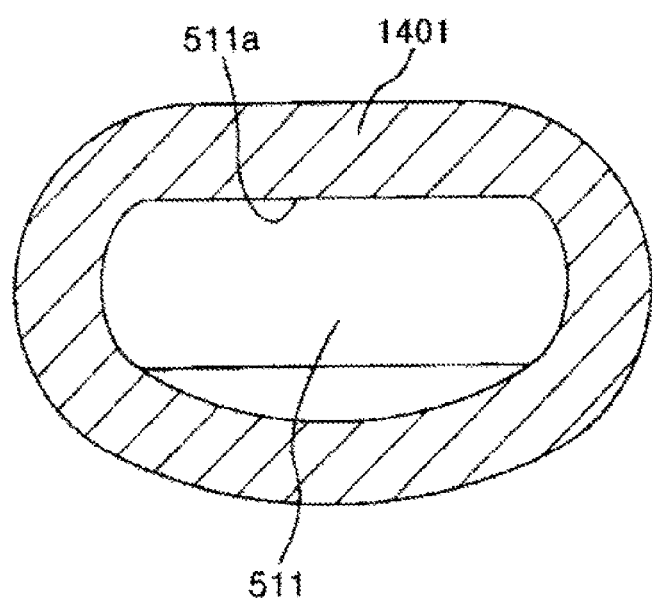

PUNCTURE DEVICE

CROSS-REFERENCES TO RELATED APPLICATIONS

This application is a continuation of International Application No. PCT/JP2013/059895 filed on Apr. 1, 2013, the entire content of which is incorporated herein by reference.

TECHNICAL FIELD

The present disclosure generally relates to a puncture device.

BACKGROUND DISCUSSION

If a person suffers from urinary incontinence, for example, from stress urinary incontinence, then urine leakage occurs when abdominal pressure is applied during normal movement or by laughing, coughing, or sneezing. This can be caused, for example, by a fact that pelvic floor muscles which are muscles which support the urethra are loosened by birth.

For the treatment of urinary incontinence, surgical therapy is effective, and for example, a living body tissue supporting strip indwelling called "sling" is used and placed into the body to support the urethra (for example, U.S. Patent Application Publication No. 2003/171644). To indwell the sling, the operator would incise the vagina with a scalpel, peel off a region between the urethra and the vagina and communicate the peeled off region and the outside through an obturator foramen using a puncture needle or the like. Then, in such a state as just described, the sling is indwelled in the body.

However, if the vagina is incised, the sling may be exposed to the inside of the vagina through a wound caused by the incision or complications, such as infection from the wound. Further, since the vagina is incised, there is a drawback that the invasion can be relatively significant and the burdensome on the patient. Further, the urethra may be damaged during the manipulation by the operator, and the operator's finger may be damaged.

SUMMARY

A puncture device is disclosed which can be stably indwelled, when, for example, an implant is to be indwelled into the living body.

A puncture device is disclosed, which can include a puncture needle curved in an arc and turnably supported around a turning center provided by the center of the arc, the puncture needle having a needle tip configured to puncture a living body when the puncture needle is turned and an insertion member having a linear portion of a linear shape at least at part thereof, the linear portion being configured to be inserted into the urethra or the vagina, wherein when the puncture needle is turned, the needle tip has a locus inclined with respect to a plane orthogonal to the linear portion.

An exemplary puncture device, wherein the inclination angle is 20 to 60 degrees.

An exemplary puncture device, wherein the puncture needle and the insertion member are connectable to each other, and the puncture device further can include a supporting member configured to turnably support the puncture needle.

An exemplary puncture device, wherein the insertion member is configured to be inserted into the urethra, and the supporting member is capable of regulating a positional relationship between the puncture needle and the insertion member such that, when the puncture needle turns to puncture the living body, the needle tip passes a farther side from the turning center of the puncture needle than the insertion member.

An exemplary puncture device, wherein, as the insertion member, a urethral insertion member configured to be inserted into the urethra and a vaginal insertion member configured to be inserted into the vagina are provided, and the supporting member is capable of regulating a positional relationship between the puncture needle and the vaginal insertion member such that, when the puncture needle turns to puncture a tissue of the living body, the needle tip does not interfere with the vaginal insertion member.

An exemplary puncture device, wherein the puncture needle has a flattened transverse sectional shape at least at a portion thereof in a longitudinal direction.

An exemplary puncture device, wherein, in a state in which the puncture needle punctures the living body, the portion of the puncture needle is positioned between the urethra and the vagina, the portion having its longitudinal axis directed substantially in parallel to the urethra.

An exemplary puncture device according, wherein the puncture needle has a portion configured from a hollow body, the hollow body accommodating therein an implant having flexibility and having a strip-like shape.

An exemplary puncture device, wherein the puncture needle has a through-hole in the proximity of the needle tip thereof, the through-hole being engageable with an implant having flexibility and having a strip-like shape.

An exemplary puncture device, further including a medical tube into which an elongated implant can be inserted, wherein the medical tube is configured from a tube open at the both ends thereof, the medical tube having a curved portion in which at least midway thereof in a longitudinal direction is curved in an arc, the curved portion maintaining the curved state thereof, and the medical tube is used after the puncture needle is turned.

An exemplary puncture device, wherein the puncture device is used to indwell an implant having a strip-like shape into the inside of the living body, the puncture needle punctures the living body to form a primary threading hole in the living body, the puncture device can include an outer pipe into and from which the puncture needle can be inserted and removed, the outer pipe passing through the primary threading hole in an assembled state in which the puncture needle is inserted and assembled, thereby changing the primary threading hole into a secondary threading hole into which the implant can be threaded, and the puncture needle has a puncture needle side expansion portion which forms the primary threading hole such that the primary threading hole is expanded to a degree substantially same as the width of the implant.

An exemplary puncture device, wherein the puncture device is used to indwell an implant having a strip-like shape into the inside of the living body, the puncture needle punctures the living body to form a primary threading hole in the living body, the puncture device can include an outer pipe into and from which the puncture needle can be inserted and removed, the outer pipe passing through the primary threading hole in an assembled state in which the puncture needle is inserted and assembled, thereby changing the primary threading hole into a secondary threading hole into which the implant can be threaded, and the outer pipe can include an outer pipe side expansion portion, so that in forming the secondary threading hole, the second insertion hole is expanded to a degree similar to the width of the implant.

An exemplary puncture device, wherein the puncture needle has a needle main body and an extension needle having the needle tip provided thereon, the extension needle being provided for relative movement with respect to the needle main body along a longitudinal direction of the needle main body, and the puncture device further can include extension means for moving the extension needle in a direction toward a distal end of the needle main body with respect to the needle main body to extend the puncture needle.

An exemplary puncture device, further including an insertion portion configured to be inserted into a living body lumen, an elongated member movably provided to pass through the living body tissue, a support member movably supports the elongated member and supports the insertion portion and a peeling off portion configured to peel off the living body tissue on the inner side of the living body in accordance with a turning movement of the puncture needle when the puncture needle is turned, the puncture device further including a restriction mechanism for restricting a direction in which the peeling portion peels off the living body tissue, the direction being fixed with respect to the insertion member.

An exemplary puncture device, wherein an implant is indwelled between the urethra and the vagina for use for medical treatment of a disease of pelvic viscera.

A puncture device is disclosed, which can include puncture needle turnably supported with a center axis as a turning center, the puncture needle having a needle tip that punctures a living body when the puncture needle is turned and an insertion member having a linear portion of a linear shape at least at part thereof, the linear portion being configured to be inserted into a urethra, wherein when the puncture needle turns, the needle tip has a locus positioned in a side farther from the center axis than the linear portion and/or an extension line of the linear portion, and the center axis and the linear portion and/or the extension line of the linear portion cross with each other.

An exemplary puncture device, wherein the puncture needle is curved in an arc and has the center axis serving as the turning center provided by the center of the arc.

A method is disclosed of forming a path in living body tissue, the method comprising: inserting an insertion member into an urethra or a vagina, the insertion member having a linear portion of a linear shape at least at part of the insertion member; puncturing the living body with a puncture needle, the puncture needle being curved in an arc and turnably supported around a turning center provided by the center of the arc, the puncture needle having a needle tip configured to puncture the living body when the puncture needle is turned; and turning the puncture needle such that the needle tip has a locus inclined with respect to a plane orthogonal to the linear portion.

With the present disclosure, when, for example, an implant is to be indwelled into a living body, the puncture needle can be turned to puncture the living body to form a puncture hole in the living body. The puncture hole can have such a shape and a posture with respect to the urethra or the vagina that the implant can be indwelled stably. Then, by threading the implant into the puncture hole, the implant can be stably indwelled in the living body.

BRIEF DESCRIPTION OF THE DRAWINGS

FIG. 4(*b*) is a sectional view taken along line IVb-IVb of FIG. 4(*a*).

FIG. 5 is a cross sectional view depicting a guide portion of a frame provided in the puncture device depicted in FIG. 1.

FIG. 10(*b*) is a front view depicting a positional relationship between the puncture member and the obturator foramen (pelvis).

FIGS. 12(*a*) and 12(*b*) are cross sectional views depicting an example of a shape of the vaginal wall.

FIG. 21(*b*) is a sectional view taken along line XXIb-XXIb of FIG. 21(*a*).

DETAILED DESCRIPTION

In the following, a puncture device of the present disclosure is described in detail with reference to preferred embodiments depicted in the accompanying drawings.

Figure 2:
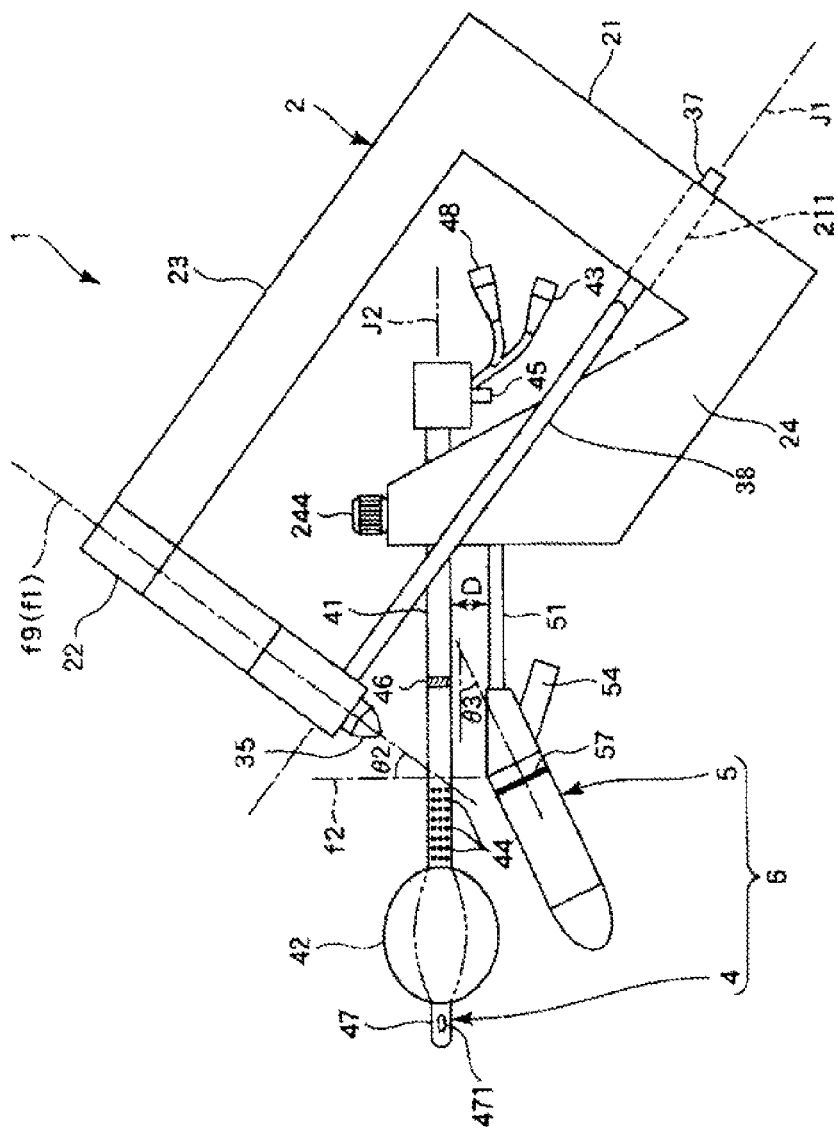
FIG. 2 is a lateral view of the puncture device depicted in FIG. 1.
Figure 3:
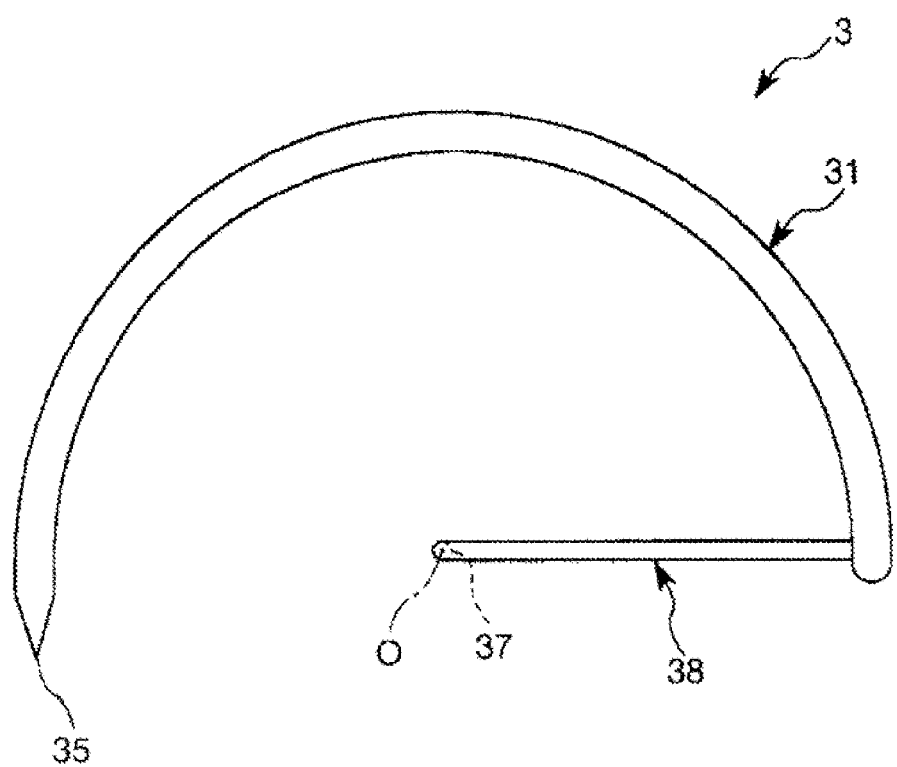
FIG. 3 is a plan view depicting a puncture member, which includes the puncture device as depicted in FIG. 1.

It is to be noted that, in the following description, the left side in FIG. 2 is referred to as "distal end," the right side as "proximal end," the upper side as "upper," and the lower side as "lower" for the convenience of description. FIG. 2 depicts a state in which the puncture device is not used as yet, and in the following description, this state is referred to also as "initial state" for the convenience of description. Further, a state in which the puncture device (insertion tool) depicted in FIG. 2 is mounted on a patient is referred to also as "mounted state."

Figure 1:
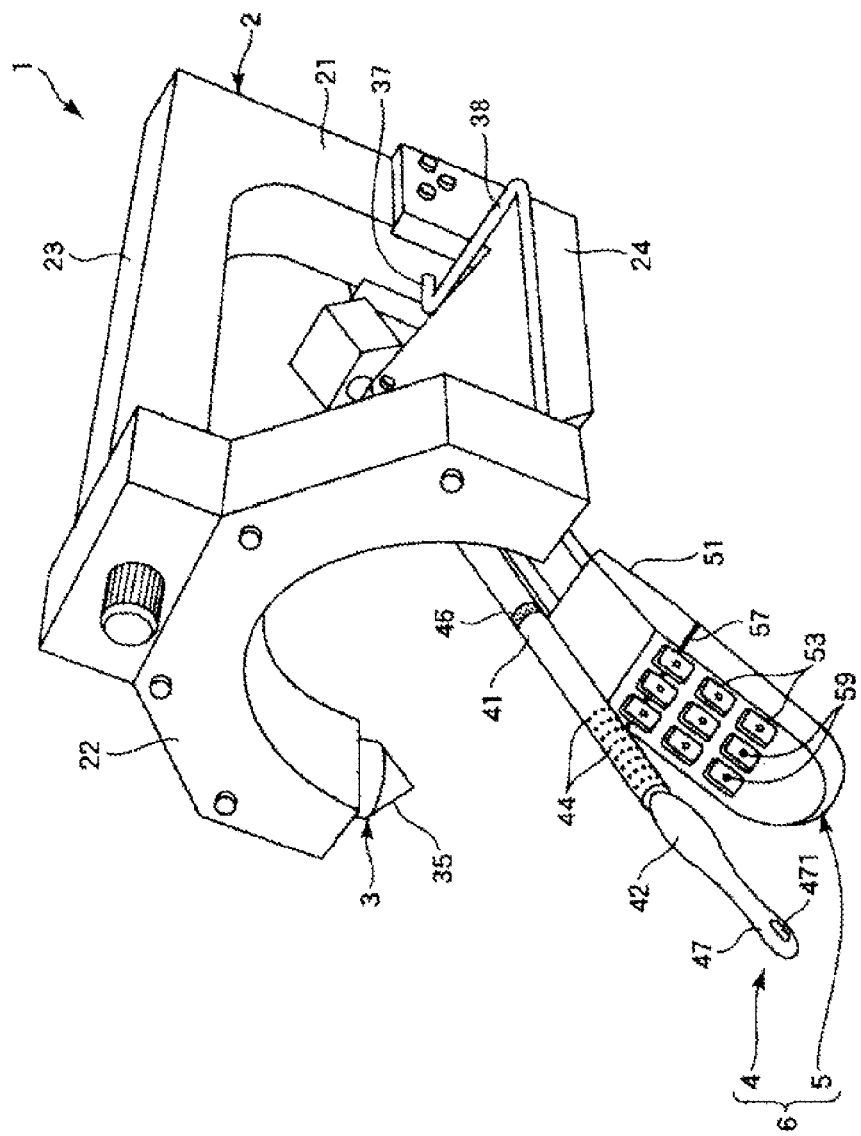
FIG. 1 is a perspective view depicting a first embodiment of a puncture device of the present disclosure.

The puncture device 1 depicted in FIGS. 1 and 2 is a device used for the treatment of female urinary incontinence, for example, for the treatment of a disease of pelvic viscera by dwelling an implant 9, which is a living body tissue supporting indwelling for the treatment of urinary incontinence, between the urethra and the vagina.

The puncture device 1 can include a frame (supporting member) 2, a puncture member 3, a urethral insertion member (insertion member) 4, and a vaginal insertion member (insertion member) 5. The puncture member 3, urethral insertion member 4 and vaginal insertion member 5 are supported on the frame 2. Further, in the puncture device 1, the urethral insertion member 4 and the vaginal insertion member 5 configure an insertion tool 6. The components mentioned are described in order.

The puncture member 3 is a member for puncturing the living body. Such a puncture member 3 as just described has a puncture needle (elongated member) 31, a shaft portion 37, and a connection portion 38 for connecting the puncture needle 31 and the shaft portion 37 to each other. The puncture needle 31, connection portion 38 and shaft portion 37 may be formed integrally, or at least one of them may be formed as a separate member from the other members.

Figure 4A:
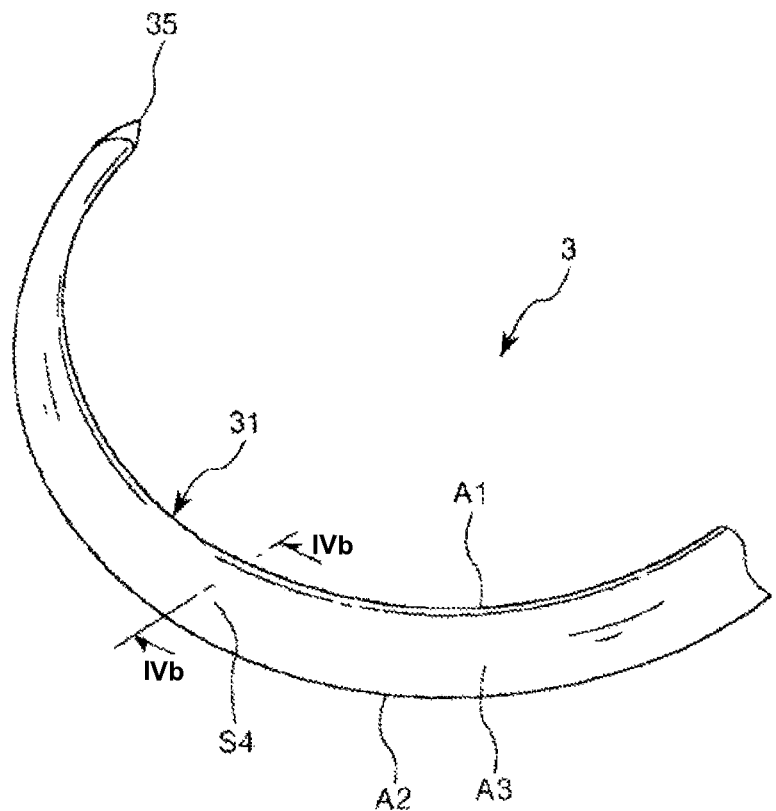
FIG. 4(*a*) is a perspective view depicting the puncture member, which includes the puncture device depicted in FIG. 1.
Figure 4B:
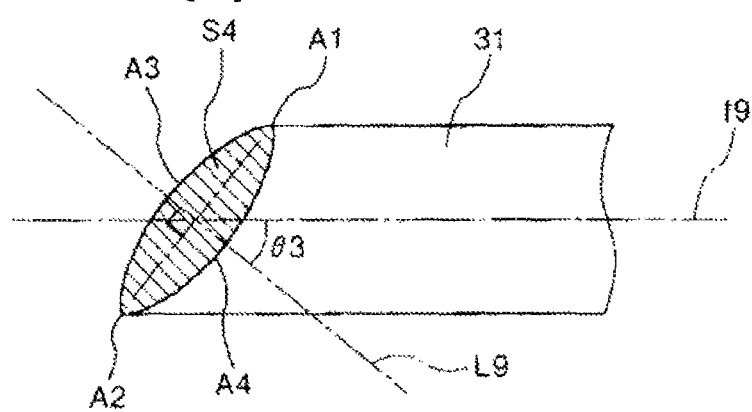

The puncture needle 31 is configured from an elongated solid body and has a sharp needle tip 35 at the distal end thereof. Further, the puncture needle 31 has a curved shape curved in an arc and has a flattened transverse cross sectional shape as depicted in FIG. 4(b). Further, the width of the puncture needle 31 is designed substantially equal to the width of an implant main body 91 (main body portion 911) of the implant 9. Consequently, the main body portion 911 can be disposed in a sufficiently developed state in the living body. It is to be noted that the flattened shape is not particularly limited, but can be made, for example, a diamond shape rounded at corners thereof, a rectangle (flattened shape) rounded at corners thereof or a spindle shape having a width greater (diameter increased) at a central portion than at the both end portions thereof.

It is to be noted that the puncture needle 31 is not limited to that of a solid body but may be that of a hollow body open at the both ends thereof. In this case, the hollow body can be used, for example, with a guide wire threaded therethrough.

In the following description, for the convenience of description, as depicted in FIG. 4(b), an end portion positioned on the inner side in a longitudinal direction is referred to also as "inner peripheral portion A1"; another end portion on the outer side also as "outer peripheral portion A2"; a face directed upward also as "front surface A3"; and another face directed downward also as "rear surface A4."

Where, as depicted in FIG. 4(b), a plane including the center point of the arc of a central portion S4 and the center point of a transverse sectional shape across the longitudinal direction of the puncture needle 31 (plane including the center axis of the puncture needle 31) is represented as plane f9 and the angle between the plane f9 and a linear line L9 which is a linear line coincident with the thicknesswise direction of the puncture needle 31 at the central portion S4 (direction orthogonal to the longitudinal direction as viewed in the transverse section) is represented as inclination angle θ3, the inclination angle θ3 preferably is an acute angle. Where the inclination angle θ3 is an acute angle, the implant 9 hereinafter described can be disposed substantially in parallel to the urethra and can support the urethra 1300 more effectively. It is to be noted that, although the inclination angle θ3 is not restricted as long as it is an acute angle, the inclination angle θ3 preferably is approximately 20 to 60 degrees, more preferably is 30 to 45 degrees, and most preferably is 35 to 40 degrees. The effect described above is further enhanced thereby.

In accordance with an exemplary embodiment, the inclination angle θ3 preferably satisfies the numerical range given hereinabove over an overall area in the extending direction of the puncture needle 31, however, the effect described above can be exhibited if at least the numerical range is satisfied in the central portion S4 in the extending direction of the puncture needle 31. It is to be noted that the "central portion S4" is a portion at least including a portion positioned between the urethra 1300 and the vagina 1400 in a state in which the puncture member 3 punctures the living body.

It is to be noted that markers may be provided at portions, at positions spaced equally from the central portion S4, of the both end portions of the puncture needle 31 which project to the outside of the living body in a state in which the puncture needle 31 is disposed in the living body (state of FIGS. 17(a) and 17(b)). Consequently, the position of the central portion S4 in the living body can be determined by comparing the positions of the two markers.

As described hereinabove, the puncture needle 31 is curved in an arc. The central angle θ1 of the arc is not limited specifically but is set suitably in accordance with various conditions. However, as hereinafter described, the central angle θ1 is set such that the needle tip 35 can enter the body from one of the inguinal regions the patient, pass between the urethra and the vagina and project to the outside of the body from the other inguinal region. In accordance with an exemplary embodiment, for example, the central angle θ1 preferably is 150 to 270 degrees, more preferably is 170 to 250 degrees, and most preferably is 190 to 230 degrees (refer to FIG. 5).

Such a puncture needle 31 as described above can turn around the turning center at the center O of the arc. The shaft portion 37 is a portion which serves as the turning center. The shaft portion 37 extends along an axis J1 that crosses with the center O of the puncture needle 31 and that crosses orthogonally with a plane f1 which can include the puncture needle 31.

The connection portion 38 connects a proximal end portion of the puncture needle 31 and a distal end portion of the shaft portion 37. Further, the connection portion 38 exhibits a substantially L shape bent substantially at the right angle in the middle thereof. Such a connection portion 38 functions also as a gripping portion to be gripped by an operator when the operator operates the puncture member 3.

Then, by gripping the connection portion 38 and operating the connection portion 38 to turn around the shaft portion 37, the living body can be punctured by the needle tip 35.

It is to be noted that each of the shaft portion 37 and the connection portion 38 is an elongated body thinner than the puncture needle 31.

As the constituent material of the puncture member 3, a hard material is used preferably. As such a hard material, for example, various resin materials such as polyethylene, polyimide, polyamide, polyester elastomer and polypropylene, various metal materials such as stainless steel, aluminum or aluminum alloy, titanium or titanium alloy and so forth or various resin materials can be used.

The frame 2 supports the puncture member 3 (puncture needle 31) for turning movement and allows the insertion tool 6 to be removably fixed thereto. By the fixation, the puncture member 3 and the insertion tool 6 are connected to each other.

The frame 2 has a function of determining a puncture path of the needle tip 35 when the puncture member 3 punctures the living body tissue. In accordance with an exemplary embodiment, for example, the frame 2 determines the positional relationship among the puncture member 3, urethral insertion member 4 and vaginal insertion member 5 such that, when the puncture member 3 is turned to puncture the living body tissue in a state in which the puncture member 3 and the insertion tool 6 are connected to each other, the locus of the needle tip 35 may pass the remote side from the center O (axis J1) of the puncture needle 31 with respect to the urethral insertion member 4 (or an extension line of the urethral insertion member 4) and the needle tip 35 may pass between the urethral insertion member 4 and the vaginal insertion member 5 without interfering with any of the urethral insertion member 4 and the vaginal insertion member 5 (refer to FIG. 2). An implant 9 can be indwelled in a puncture hole formed in the living body by the needle tip 35 in a state in which the positional relationship is regulated in this manner.

It is to be noted that, by such a frame 2 as just described, the axis J1 is positioned such that the axis J1 crosses with at least one of the urethral insertion member 4 and an extension line of the urethral insertion member 4.

As depicted in FIGS. 1 and 2, the frame 2 has a bearing portion 21 which supports the shaft portion 37 of the puncture member 3 for rotation thereon, a guide portion (holding portion) 22 which guides the puncture member 3, a connection portion 23 which connects the bearing portion 21 and the guide portion 22 to each other, and a fixing portion 24 to which the insertion tool 6 is fixed.

The bearing portion 21 is positioned on the proximal end side of the puncture device 1 and extends in a direction substantially orthogonal to the axis J1. A through-hole 211 is formed on the axis J1 of the bearing portion 21, and the shaft portion 37 is rotatably inserted in the through-hole 211. Consequently, the puncture member 3 is supported on the frame 2 in a state capable of turning around the axis J1.

The guide portion 22 is positioned on the distal end side of the puncture device 1 and disposed in an opposing relationship to the bearing portion 21. As depicted in FIG. 5, a substantially C-shaped guide groove 221 is formed in the guide portion 22 to accommodate, in an initial state depicted in FIG. 6, the puncture member 3 and guides the puncture member 3 in the guide groove 221. If the puncture member 3 is operated to turn, then the puncture member 3 gradually projects from a distal end side opening 222 side of the guide portion 22, and the needle tip finally advances into the guide portion 22 from a proximal end side opening 223 side as depicted in FIG. 7.

Figure 6:
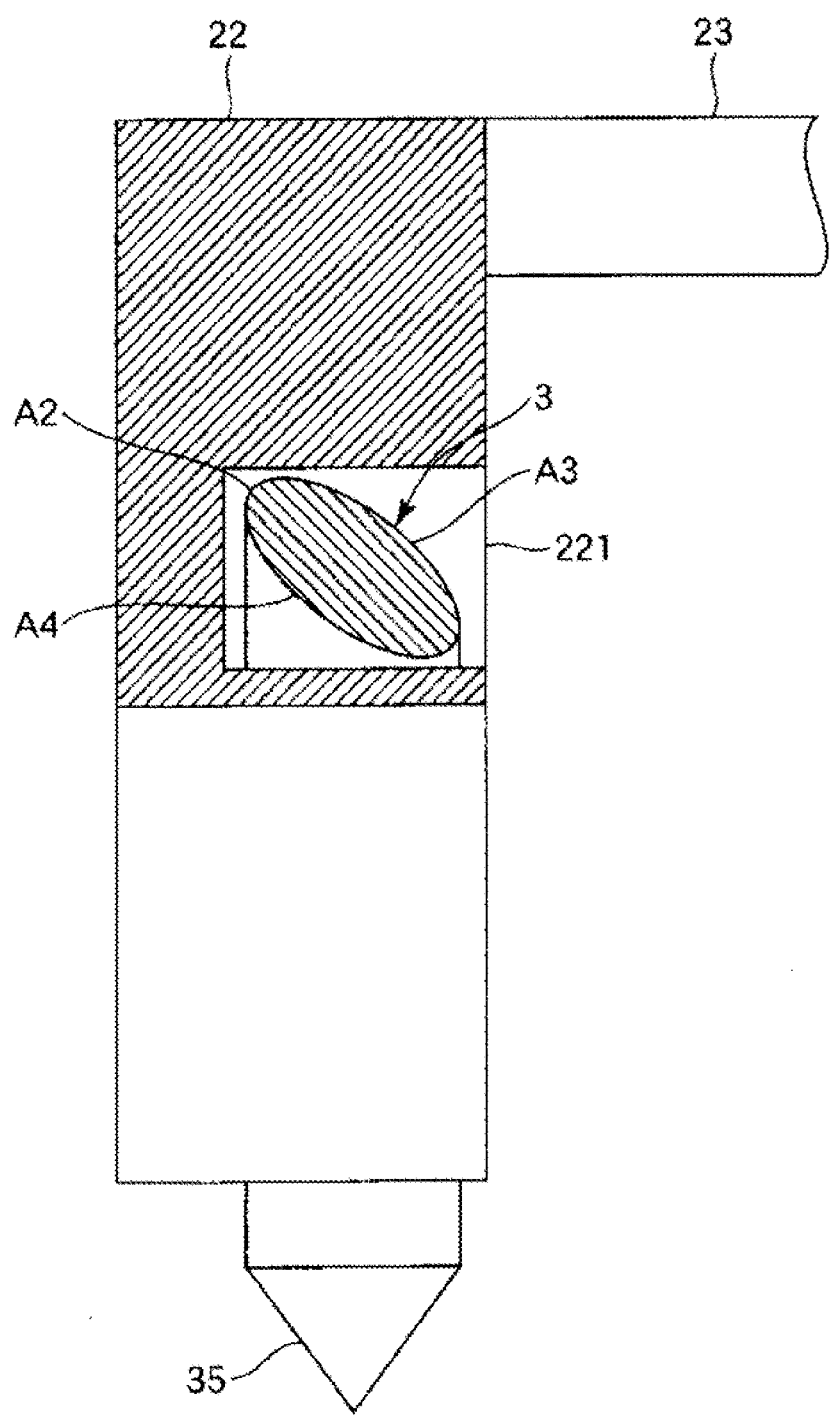
FIG. 6 is a cross sectional view depicting the guide portion of the frame provided in the puncture device depicted in FIG. 1.
Figure 7:
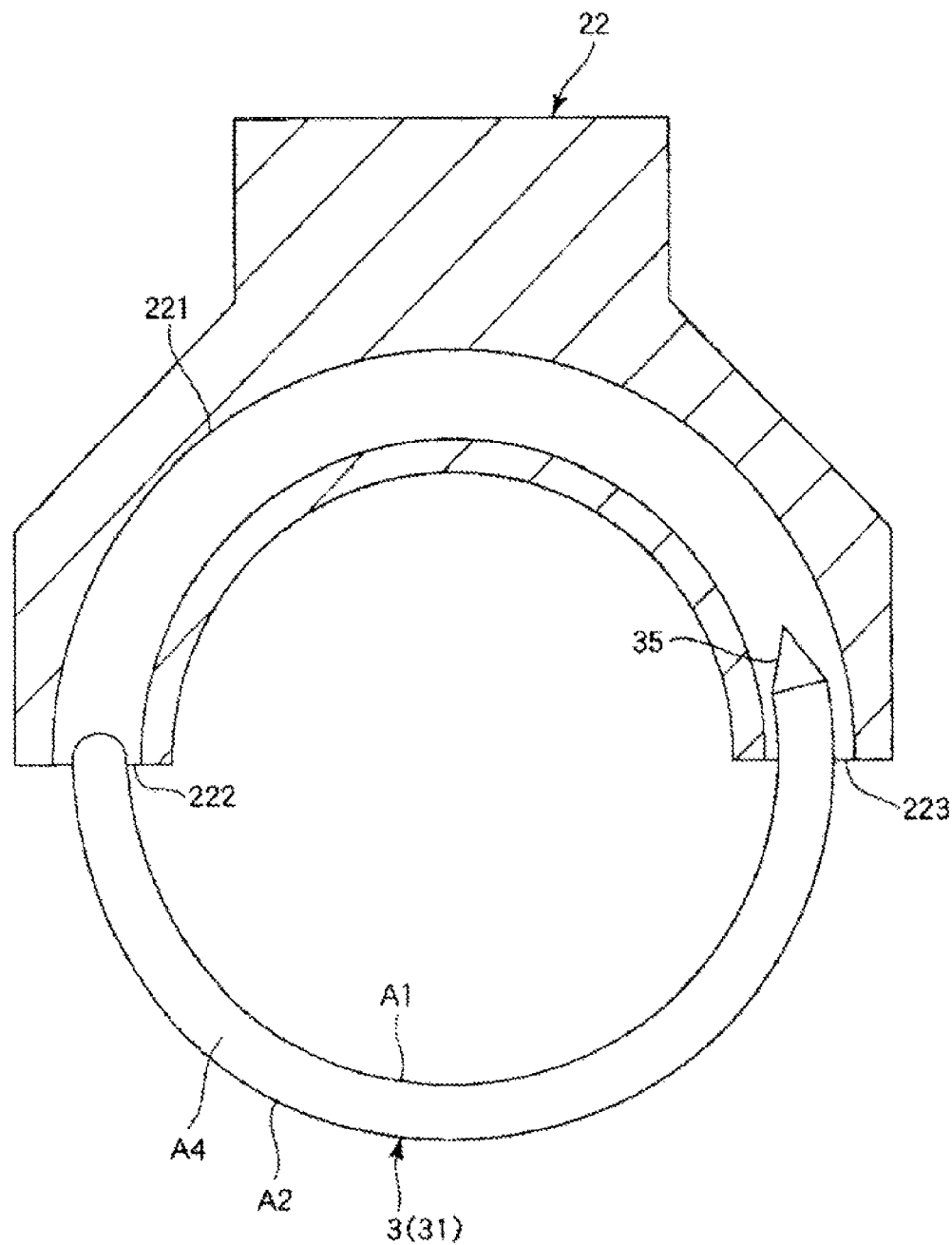
FIG. 7 is a cross sectional view depicting the guide portion of the frame provided in the puncture device depicted in FIG. 1.

Further, as depicted in FIG. 6, in a state in which the puncture member 3 is disposed in the guide groove 221, the rear surface A4 is positioned on the distal end side while the front surface A3 is positioned on the proximal end side.

The connection portion 23 connects the bearing portion 21 and the guide portion 22 to each other. Further, the connection portion 23 is in the form of a bar extending substantially in parallel to the axis J1. The connection portion 23 functions also as a gripping portion, and an operator can grip the connection portion 23 to use the puncture device 1.

Figure 8:
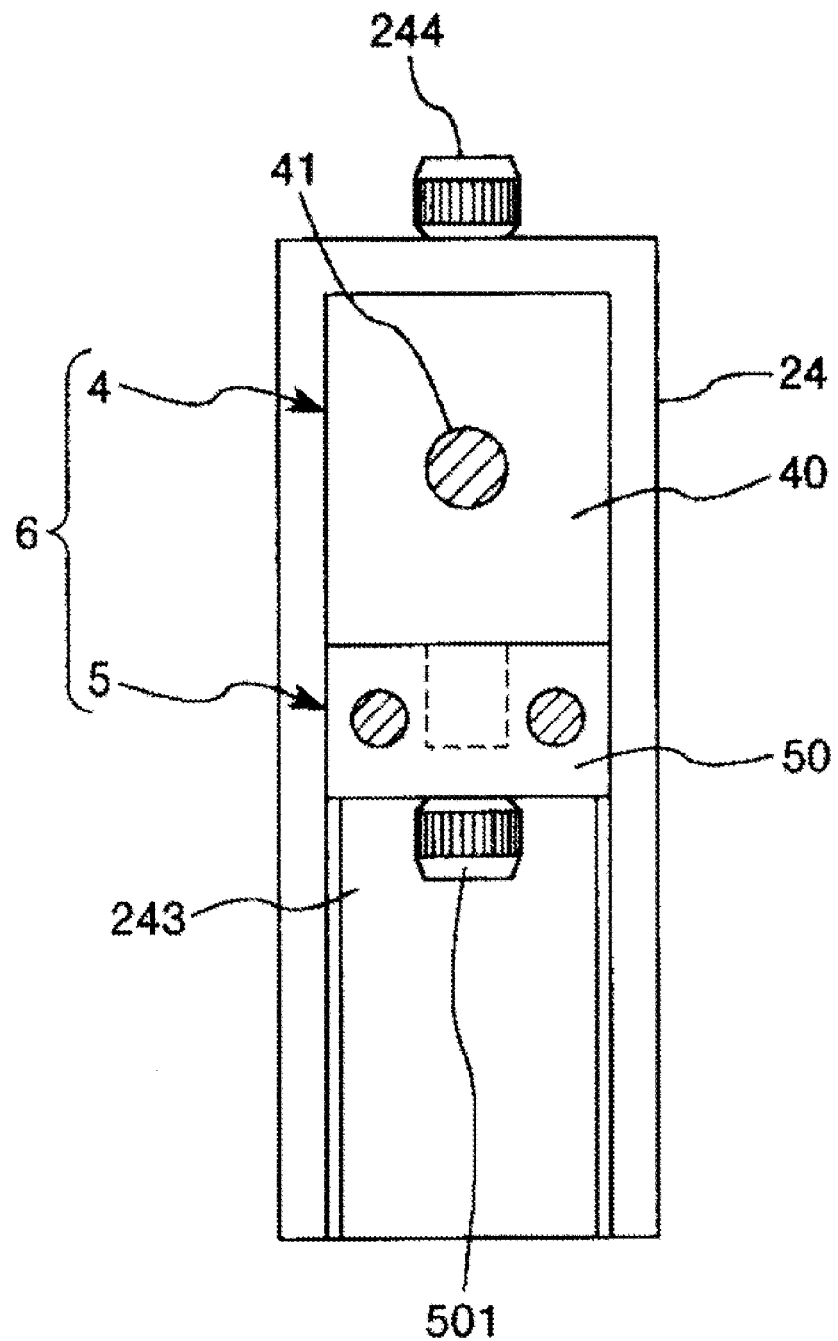
FIG. 8 is a plan view depicting a fixing portion of the frame provided in the puncture device shown in FIG. 1.

The fixing portion 24 is disposed in an opposing relationship to the connection portion 23 with the axis J1 interposed therebetween. As depicted in FIG. 8, the fixing portion 24 has a recessed portion 243 into which a supporting portion 60 hereinafter described of the insertion tool 6 is to be fitted, and a male thread 244. If the supporting portion 60 is fitted into the recessed portion 243 and the male thread 244 is tightened into a female thread (not depicted) of the supporting portion 60, the insertion tool 6 can be fixed to the fixing portion 24.

Figure 9:
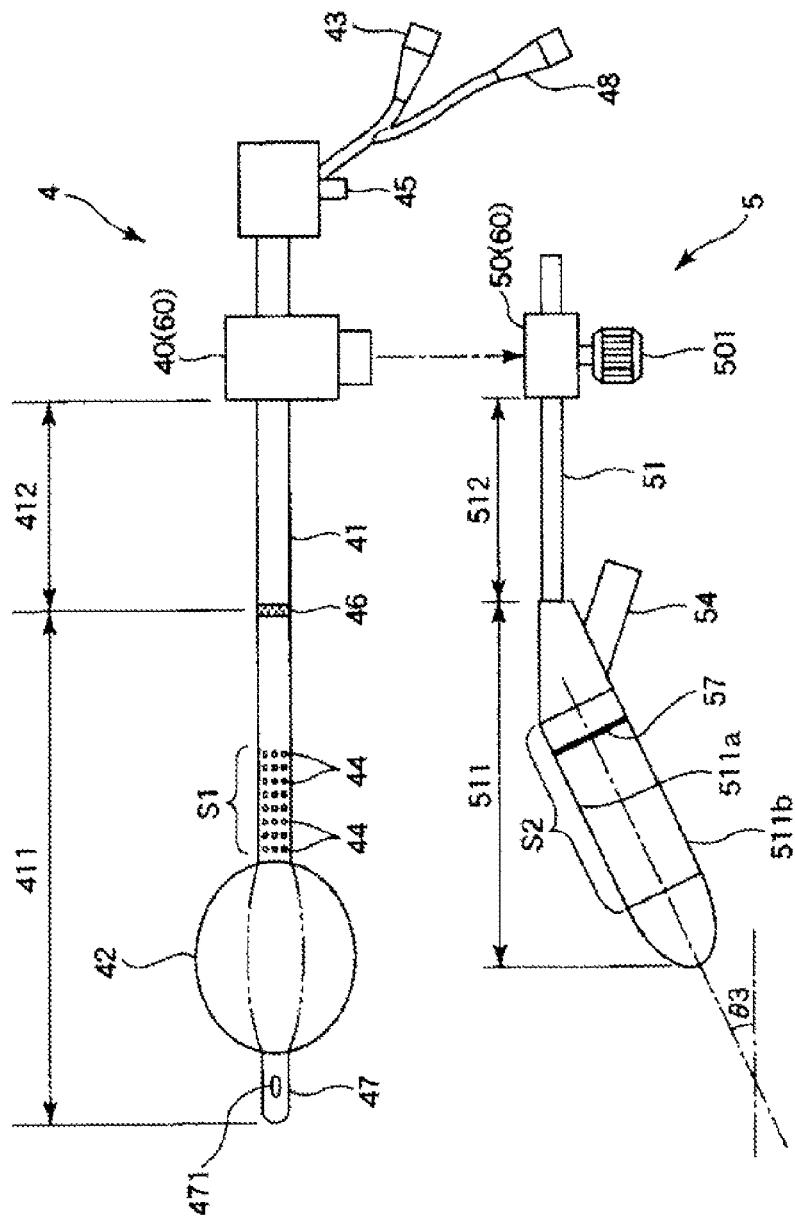
FIG. 9 is a lateral view depicting an insertion tool, which includes the puncture device depicted in FIG. 1.

As depicted in FIGS. 1 and 9, the insertion tool 6 has a urethral insertion portion (second insertion portion) 41 which is to be inserted into the urethra 1300, a vaginal insertion portion 51 (first insertion portion) which is to be inserted into the vagina 1400, and a supporting portion 60 which supports the urethral insertion portion 41 and the vaginal insertion portion 51 thereon. As described hereinabove, the insertion tool 6 is configured from the urethral insertion member 4 and the vaginal insertion member 5, and the urethral insertion member 4 can include the urethral insertion portion 41 while the vaginal insertion member 5 can include the vaginal insertion portion 51. Further, the supporting portion 60 has a supporting portion 40 which is provided on the urethral insertion member 4 and supports the urethral insertion portion 41 and a supporting portion 50 which is provided on the vaginal insertion member 5 and supports the vaginal insertion portion 51. In the insertion tool 6, the urethral insertion member 4 and the vaginal insertion member 5 can be removably mounted through the supporting portions 40 and 50, respectively. In the following, the urethral insertion member 4 and the vaginal insertion member 5 are described in order.

The urethral insertion member 4 has a urethral insertion portion (linear portion) 41 having a linear shape to the middle thereof so as to be inserted into the urethra 1300, and a supporting portion 40 which supports the urethral insertion portion 41. It is to be noted that, in the following description, a portion of the urethral insertion portion 41 which is positioned in the urethra 1300 (including the bladder 1310) is referred to also as "insertion portion 411" and another portion of the urethral insertion portion 41 which is exposed to the outside of the body from the urethral orifice in the mounted state and extends to the supporting portion 40 is referred to also as "non-insertion portion 412" for the convenience of description.

The urethral insertion portion 41 has a form of a linear pipe rounded at a distal end thereof. Further, the urethral insertion portion 41 has an expandable/contractible balloon 42 and a urine discharge portion 47 provided at a distal end portion of the insertion portion 411 thereof. The balloon 42 functions as a regulation portion for regulating the position of the urethral insertion member 4 in the axial direction in the urethra 1300. In accordance with an exemplary embodiment, for example, when the puncture device 1 is used, the balloon 42 is inserted into the bladder 1310 of the patient and then expanded. Then, the expanded balloon 42 is caught by the bladder neck thereby to fix the position of the urethral insertion member 4 with respect to the bladder 1310 and the urethra 1300. Meanwhile, the urine discharge portion 47 is used to discharge urine in the bladder 1310 therethrough.

The balloon 42 is connected to a balloon port 43 provided at a proximal end portion of the urethral insertion portion 41 passing through the inside of the urethral insertion portion 41. An expansion tool such as a syringe can be connected to the balloon port 43. If working fluid (liquid such as saline solution, gas or the like) is supplied from the balloon expansion tool into the balloon 42, then the balloon 42 is expanded, but if the working fluid is taken out from the balloon 42 by the balloon expansion tool conversely, then the balloon 42 is contracted. It is to be noted that, in FIG. 9, the balloon 42 in a contracted state is indicated by an alternate long and two short dashes line while the balloon 42 in an expanded state is indicated by a solid line.

In accordance with an exemplary embodiment, a discharge hole 471 is provided in the urine discharge portion 47 such that it communicates the inside and the outside of the urine discharge portion 47 with each other. Further, the urine discharge portion 47 passes through the inside of the urethral insertion portion 41 and is connected to a urine discharge port 48 provided at a proximal end portion of the urethral insertion portion 41. Therefore, urine introduced from the discharge hole 471 can be discharged from the urine discharge port 48.

The balloon 42 and the urine discharge portion 47 can be configured, for example, from a double lumen.

Further, a plurality of suction holes 44 are formed at an intermediate portion of the insertion portion 411. The plurality of suction holes 44 are disposed over an overall area of the urethral insertion portion 41 in a circumferential direction. Each of the suction holes 44 can extend through the urethral insertion portion 41 and is connected to a suction port 45 provided at a proximal end portion of the urethral insertion portion 41. A suction device such as a pump can be connected to the suction port 45. If the suction device is rendered operative in a state in which the urethral insertion portion 41 is inserted in the urethra 1300, then the urethral wall can be sucked and fixed to the urethral insertion portion 41. Then, if the urethral insertion portion 41 in this state is pushed to the distal end side (into the body), then also the urethra 1300 is pushed in together, and for example, the bladder 1310 can be displaced to a position which does not overlap with the puncture passage of the puncture member 3 and the puncture passage of the puncture member 3 can be assured. Therefore, the puncture of the puncture member 3 can be carried out relatively accurately and safely. It is to be noted that the number of suction holes 44 is not limited particularly and may be, for example, one. Further, the disposition of the suction holes 44 is not limited particularly, and the suction holes 44 may be formed, for example, at only part of the urethral insertion portion 41 in a circumferential direction.

Further, a marker 46 for determining the insertion depth of the urethral insertion portion 41 in the urethra 1300 is provided at a boundary portion between the insertion portion 411 and the non-insertion portion 412. The marker 46 is positioned at the urethral orifice when the urethral insertion portion 41 is inserted into the urethra 1300 until the balloon 42 is positioned in the bladder 1310. Consequently, the insertion depth of the insertion portion 411 in the urethra 1300 can be determined. As the marker 46, it is only necessary that it be visually recognized from the outside, and the marker 46 can be configured, for example, from a colored portion or a concave-convex portion. It is to be noted that the marker 46 may be replaced by graduations representing the distances from the distal end of the urethral insertion portion 41.

The length of the insertion portion 411 is not limited particularly and is set suitably depending upon the length of the urethra 1300, and the shape of the bladder 1310. Since the length of the urethra of general women is approximately 30 to 50 mm, the length of the insertion portion 411 preferably is approximately 50 to 100 mm.

Although the length of the non-insertion portion 412 (spacing distance between the urethral orifice and the supporting portion 40) is not limited particularly, it preferably is shorter than approximately 100 mm, and more preferably is approximately 20 to 50 mm. Consequently, the non-insertion portion 412 can be made with an appropriate length and is improved in operability. If the length of the non-insertion portion 412 exceeds the upper limit value given above, then depending upon the configuration of the frame 2 and so forth, the center of gravity of the puncture device 1 is located away from the patient, resulting in the stability of the puncture device 1 in the mounted state may deteriorate.

The constituent material of the urethral insertion member 4 is not limited particularly, and for example, various metal materials such as stainless steel, aluminum or aluminum alloy, titanium or titanium alloy or various resin materials can be used.

As described hereinabove, the puncture needle 31 can turn around the axis J1, and upon such turning, the needle tip 35 passes on the plane f9 (plane f1) and the locus of the needle tip 35 can be virtualized on the plane f9.

Here, the inclination angle θ2 of the plane f9 (plane f1 (locus)) with respect to a plane f2 orthogonal to the axis J2 of the urethral insertion portion 41 preferably is approximately 20 to 60 degrees, more preferably is approximately 30 to 45 degrees, and most preferably is approximately 35 to 40 degrees. In accordance with an exemplary embodiment, the puncture needle 31 preferably is indwelled in the body such that the angle between the plane f9 and a plane orthogonal to the axis of the urethra 1300 is approximately 20 to 60 degrees, more preferably is indwelled such that the angle is approximately 30 to 45 degrees, and most preferably is indwelled such that the angle is approximately 35 to 40 degrees. By such indwelling of the puncture needle 31, the puncture of the puncture member 3 can be readily carried out and the puncture distance by the puncture member 3 can be made shorter.

Figure 10A:
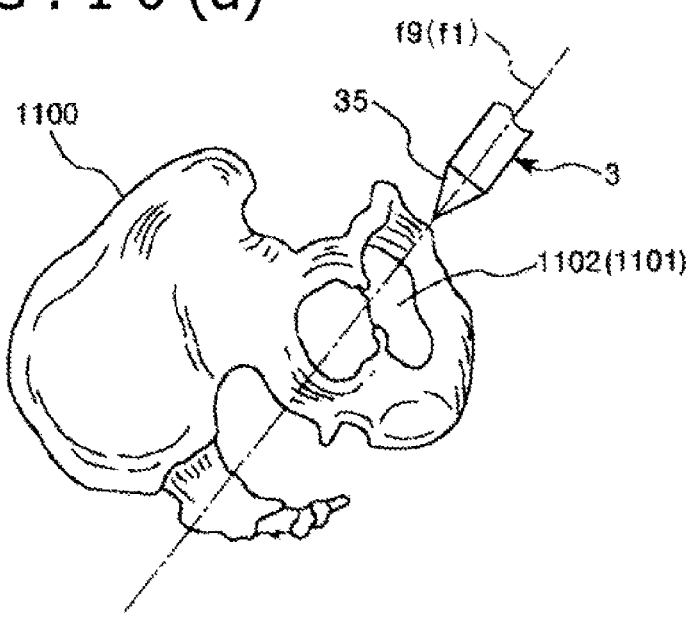
FIG. 10(*a*) is a lateral view depicting a positional relationship between the puncture member and the obturator foramen (pelvis).
Figure 10B:
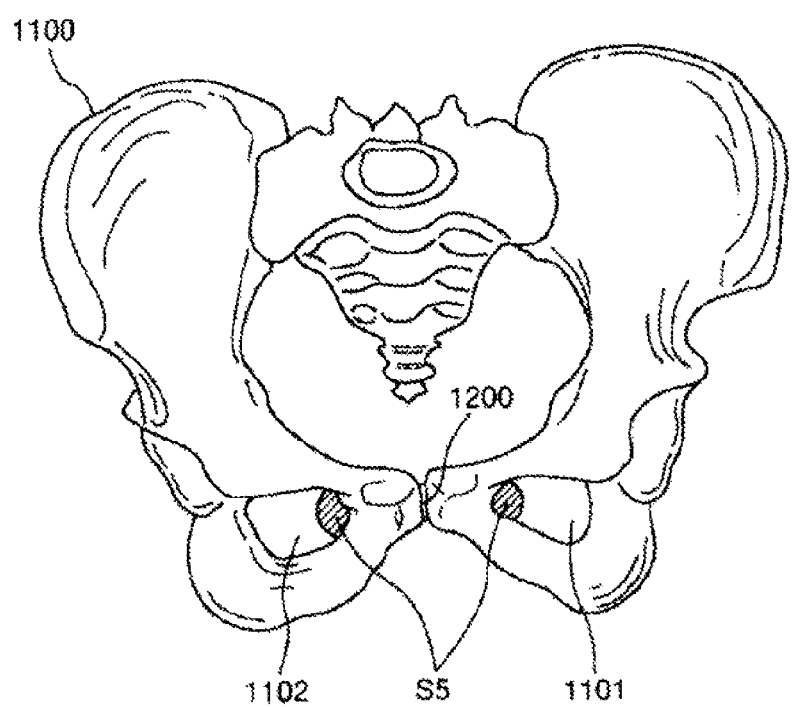

By setting the inclination angle θ2 within the range described above, the puncture member 3 can capture the left and right obturator foramens 1101 and 1102 of the pelvis 1100 widely in plane and the puncture space of the puncture member 3 can be assured wide as depicted in FIG. 10(*a*). In accordance with an exemplary embodiment, for example, in a state in which the patient is placed in a predetermined position (lithotomy position), the puncture member 3 can puncture in a comparatively vertical direction with respect to the obturator foramens 1101 and 1102. Therefore, the puncture of the puncture member 3 can be carried out readily. In addition, where the puncture member 3 punctures in a comparatively vertical direction with respect to the obturator foramens 1101 and 1102, the puncture needle 3 passes a shallow portion of the tissue, and therefore, the needle tip 35 of the puncture member 3 can pass over a shorter distance between the left and right obturator foramens 1101 and 1102.

Therefore, the puncture member 3 can pass the obturator foramens 1101 and 1102 rather near to the pubic symphysis 1200, preferably a safety zone S5, as depicted in FIG. 10(*b*). Since the safety zone S5 is a region which can include a comparatively small number of nerves and blood vessels to which damage is to be avoided, the puncture member 3 can puncture in a relative safe manner. Therefore, the invasiveness can be reduced and the burden on the patient can be suppressed. By setting the inclination angle θ2 to such a range as described above, the puncture of the patient by the puncture member 3 can be appropriately carried out. Further, by the puncture at the angle specified as above, the tissue between the central urethra which refers to a middle portion of the urethra 1300 in the lengthwise direction and the vagina 1400 can be determined as a target readily. The position between the central urethra and the vagina 1400 is a position suitable as a region into which the implant 9 is to be embedded to carry out the treatment of urinary incontinence. Further, when the implant 9 is to be indwelled into the living body, the implant 9 can be stably indwelled at such a position as just described.

In contrast, if the inclination angle θ2 is smaller than the lower limit value given hereinabove or is greater than the upper limit value given hereinabove, then depending upon the individual differences of patients, the posture during the manipulation, the puncture member 3 may not capture the obturator foramens 1101 and 1102 widely in plane or may fail to sufficiently shorten the puncture passage.

More preferably, the puncture member 3 easily punctures the region between the central urethra and the vagina 1400 if it punctures in a state in which the position thereof is displaced such that the urethra 1300, the vagina 1400 or both of the urethra 1300 and the vagina 1400 are pushed into the inner side of the body. The method of pushing one of the urethra 1300 and the vagina 1400 to the inner side of the body can be, for example, a method of placing the urethral insertion member 4 and/or the vaginal insertion member 5 into a state in which the urethral insertion member 4 and/or the vaginal insertion member 5 are inserted to appropriate positions, absorbing the urethra 1300 and/or the vagina 1400 through suction holes 44 and 59 hereinafter described provided in the urethral insertion member 4 and/or the vaginal insertion member 5 and then moving the urethral insertion member 4 and/or the vaginal insertion member 5 further to the inner side of the body to predetermined positions along the individual axial lines thereof. By causing the puncture needle 31 to vertically puncture the left and right obturator foramens 1101 and 1102 of the pelvis, a path can be formed at a position suitable to indwell the implant 9.

It can be preferable to set the locus of the puncture needle 31 so as to pass the safety zone S5 of the left and right obturator foramens 1101 and 1102 of the pelvis, displace at least one of the urethra 1300 and the vagina 1400 to the inner side of the body so that the locus may be positioned between the central urethra and the vagina 1400 and causing the puncture needle 31 to puncture along the locus to form a path.

As depicted in FIGS. 1 and 9, the vaginal insertion member 5 has an elongated vaginal insertion portion (first insertion portion) 51 which is to be inserted partway into the vagina 1400, and a supporting portion 50 which supports the vaginal insertion portion 51. It is to be noted that, in the following description, a portion of the vaginal insertion portion 51 in the vagina 1400 in the mounted state is referred to as "insertion portion 511" and another portion of the vaginal insertion portion 51 which is to be exposed to the outside of the body from the vaginal orifice in the mounted state and extends to the supporting portion 50 is referred to also as "non-insertion portion 512" for the convenience of description.

The insertion portion 511 has a linear shape. Further, the insertion portion 511 extends in an inclined relationship with respect to the insertion portion 411 such that the distal end side thereof is spaced away from the insertion portion 411. By forming the insertion portion 511 in an inclined relationship with respect to the insertion portion 411, the positional relationship of the insertion portions 411 and 511 can be made closer to the positional relationship between the urethra 1300 and the vagina 1400 in comparison with those in an alternative case in which the insertion portion 511 is not inclined. Therefore, in the mounted state, the puncture device 1 can be held stably on the patient and the burden on the patient is reduced. Although the inclination angle θ3 of the insertion portion 511 with respect to the insertion portion 411 is not limited particularly, the inclination angle θ3 preferably is, for example, approximately 0 to 45 degrees, and more preferably is approximately 0 to 30 degrees. By such an inclination angle θ3 as just described, the effect described above can be exhibited more significantly. In accordance with an exemplary embodiment, if the inclination angle θ3 is smaller than the lower limit value described above or is greater than the upper limit value described above, then depending upon the individual differences of patients, the posture during the manipulation, the vagina or the urethra may be deformed unnaturally in the mounted state and the puncture device 1 may not be held stably.

Figure 11:
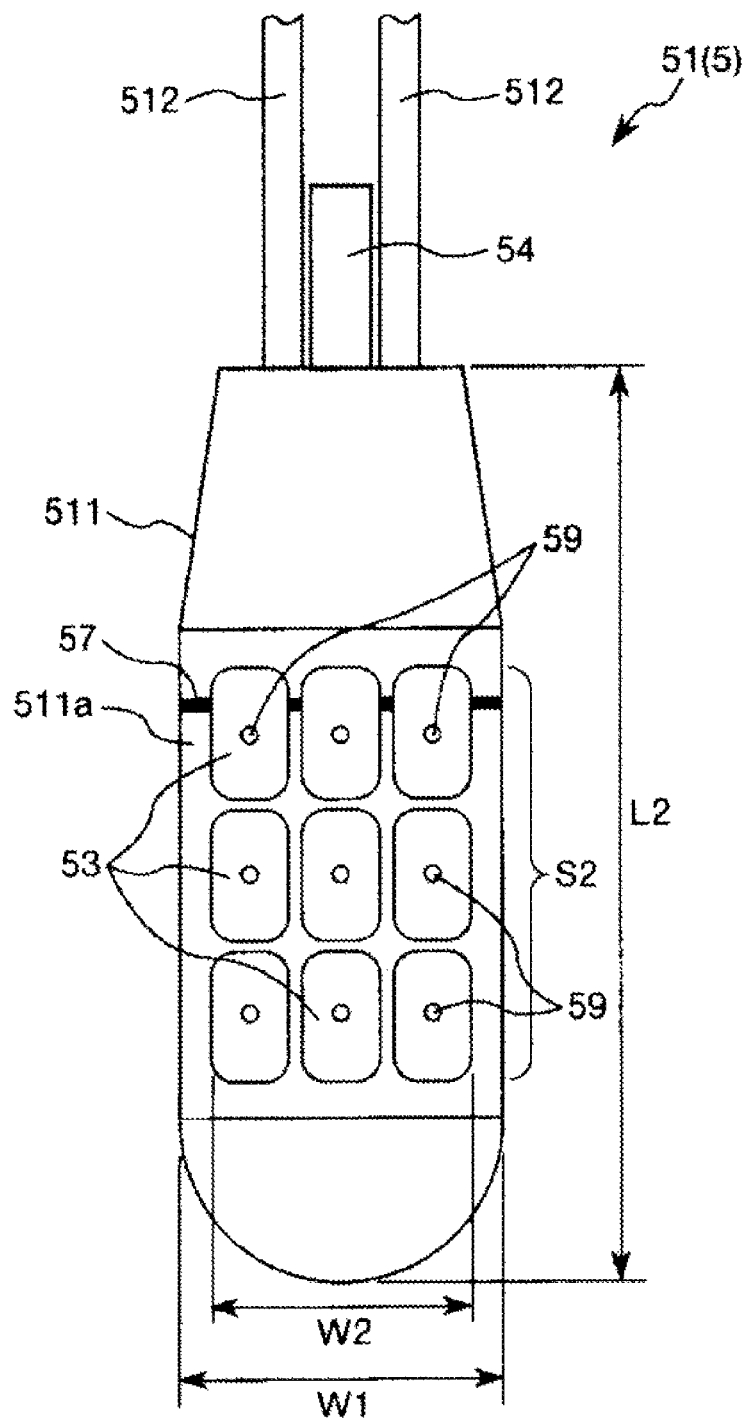
FIG. 11 is a partial enlarged view of a vaginal insertion member, which includes the insertion tool depicted in FIG. 9.

As depicted in FIG. 11, the insertion portion 511 has a flattened shape crushed in the upward and downward direction of the puncture device 1 (array direction of the urethra and the vagina). Further, the insertion portion 511 has a central portion whose width W1 is substantially fixed and a rounded distal end portion. Although the length L2 of the insertion portion 511 is not limited particularly, it preferably is approximately 20 to 100 mm, and more preferably is approximately 30 to 60 mm. Further, although the width W1 of the insertion portion 511 is not limited particularly, it preferably is approximately 10 to 40 mm, and more preferably is approximately 20 to 30 mm. Further, although the thickness of the insertion portion 511 is not limited particularly, it preferably is approximately 5 to 25 mm, and more preferably is approximately 10 to 20 mm. By forming the insertion portion 511 with such a length×width×thickness as given above, the insertion portion 511 comes to have a shape and a size suitable for general vaginas. Therefore, the stability of the puncture device 1 in the mounted state increases and the burden on the patient can be reduced.

Further, a plurality of bottomed recessed portions 53 are formed on an upper face (face on the urethral insertion portion 41 side) 511a of the insertion portion 511. It is to be noted that the number of recessed portions 53 is not limited particularly and may be, for example, one. Further, one suction hole 59 is provided on the bottom face of each recessed portion 53, and the suction holes 59 are connected to a suction port 54. The suction port 54 is provided at a proximal end portion of the insertion portion 511 past the inside of the insertion portion 511. The suction port 54 can be connected to a suction apparatus such as a pump, and if the suction apparatus is rendered operative in a state in which the insertion portion 511 is inserted in the vagina 1400, then the vaginal front wall which is an upper face of the vaginal wall is absorbed and fixed to the insertion portion 511. Then, if the vaginal insertion portion 51 is pushed into the distal end side (into the body) in a state in which the vaginal wall is absorbed and fixed, then the vaginal wall can be pushed in together with the vaginal insertion portion 51. Therefore, the disposition or the shape of the vaginal wall can be arranged and a puncture passage of the puncture member 3 can be relatively assured, and the puncture of the puncture member 3 can be carried out relatively accurately and safely.

The region S2 in which the plurality of recessed portions 53 are formed is disposed in an opposing relationship to the region S1 in which the suction holes 44 of the urethral insertion member 4 are formed. Further, the needle tip 35 of the puncture member 3 passes between the regions S1 and S2. Since the urethral rear wall which is a lower face of the urethral wall is absorbed to the insertion portion 411 in the region S1 while the vaginal front wall is absorbed to the insertion portion 511 in the region S2, the urethral wall and the vaginal wall are spaced away from each other by a greater distance between the regions S1 and S2. Therefore, by causing the puncture member 3 to pass through such a region as just described, the puncture member 3 can be caused to puncture with a higher degree of safeness.

The region S2 spans over a substantially overall area of the upper face 511a in the widthwise direction. Although the width W2 of the region S2 is not limited particularly, it preferably is approximately 9 to 39 mm, and more preferably is approximately 19 to 29 mm. With such a width W2 as just described, the vaginal front wall can be absorbed to the insertion portion 511 with a higher degree of certainty without being influenced much by the shape of the vaginal wall. In accordance with an exemplary embodiment, depending upon a patient, the vagina 1400 may be formed such that the vaginal front wall 1401 thereof partly hangs into the vagina 1400 as depicted in FIG. 12(a). Also in such a case as just described, if the region S2 has such a width W2 as described above, not only the hanging portion but also portions on the both sides of the hanging portion can be absorbed with certainty as depicted in FIG. 12(b). Therefore, the vaginal front wall 1401 can be spaced away from the urethra 1300 with a higher degree of certainty without being influenced by the shape of the vagina 1400. In accordance with an exemplary embodiment, in the present embodiment, since the insertion portion 511 has a flattened shape, the vaginal front wall 1401 can be absorbed so as to be spaced further away from the urethra 1300, and the living body tissue between the urethral wall and the vaginal wall can be widened further.

Further, a marker (puncture position determining portion) 57 is provided on the insertion portion 511 such that the puncture route of the puncture device 1 can be determined therefrom. In accordance with an exemplary embodiment, for example, the puncture device 1 can be secured such that it can puncture a region between the vaginal wall and the urethral wall which exist on an upper face at a position at which the marker 57 exists. Therefore, the operability and the safety of the insertion tool 6 can be improved. The marker 57 is provided at least on the lower face 511b of the insertion portion 511. Since the lower face 511b is a face which is directed to the vaginal orifice side in the inserted state and can be determined by the operator through the vaginal orifice, by providing the marker 57 on the lower face 511b, the puncture route of the puncture device 1 can be determined with a higher degree of certainty. In addition, the insertion depth of the insertion portion 511 in the vagina can also be determined. It is to be noted that it is only necessary for the marker 57 to be viewed from the outside, and the marker 57 can be configured, for example, from a colored portion, a concave or convex portion.

The non-insertion portion 512 has a form of a thin bar extending substantially in parallel to the urethral insertion portion 41. Although the spacing distance D between the non-insertion portion 512 and the urethral insertion portion 41 is not limited particularly, it preferably is approximately 10 to 40 mm in accordance with the spacing distance between the urethral orifice and the vaginal orifice of general women (refer to FIG. 2).

Although the length of the non-insertion portion 512 (spacing distance between the vaginal orifice and the supporting portion 50) is not limited particularly, it preferably is equal to or smaller than approximately 100 mm, and more preferably is approximately 20 to 50 mm. By the length just described, the non-insertion portion 512 can have an appropriate length, and the operability can be improved. If the length of the non-insertion portion 512 exceeds the upper limit value described above, then depending upon the configuration of the frame 2 and so forth, the center of gravity of the puncture device 1 can be spaced by a great distance from the patient, and the stability of the puncture device 1 in a mounted state may be deteriorated.

The supporting portion 50 has a male thread 501 provided thereon, and the supporting portions 40 and 50 are fixed to each other by tightening the male thread 501 into a female thread (not depicted) of the supporting portion 40.

The constituent material of the vaginal insertion member 5 is not limited particularly, and, for example, various metal materials such as stainless steel, aluminum or aluminum alloy, titanium or titanium alloy or various resin materials can be used similarly to the vaginal insertion member 4.

It is to be noted that, while, in the puncture device 1, the urethral insertion member 4 and the vaginal insertion member 5 which configure the insertion tool 6 are configured removably, the configuration of the urethral insertion member 4 and the vaginal insertion member 5 is not limited to this, and the urethral insertion member 4 and the vaginal insertion member 5 may be configured non-removably.

Further, while, in the puncture device 1, the urethral insertion portion 41 is fixed to the supporting portion 40, the configuration of the urethral insertion portion 41 and the supporting portion 40 is not limited to this, and the urethral insertion portion 41 may be configured so as to allow selection between a state in which the urethral insertion portion 41 is fixed to the supporting portion 40 and another state in which the urethral insertion portion 41 is slidably movable in the axial direction on the supporting portion 40. In accordance with an exemplary embodiment, for example, such a configuration may be adopted that, if a male thread provided on the supporting portion 40 is loosened, then the urethral insertion portion 41 is placed into a state in which it can slidably move on the supporting portion 40, but if the male thread is tightened, then the urethral insertion portion 41 is placed into another state in which it is fixed to the supporting portion 40. With the configuration just described, since the length of the non-insertion portion 412 can be adjusted, the convenience in use of the insertion tool 6 is improved. It is to be noted that this similarly applies also to the vaginal insertion portion 51.

Further, while, in the puncture device 1, the components are fixed to the frame 2 such that the inclination angle θ2 is fixed, the configuration of the components is not limited to this, and the inclination angle θ2 may be variable within the numerical range given hereinabove. If this configuration is applied, then since the inclination angle θ2 can be adjusted in accordance with the patient, the convenience in use of the puncture device 1 is further improved.

Now, the implant 9 for use with the puncture device 1 is described.

Figure 13:
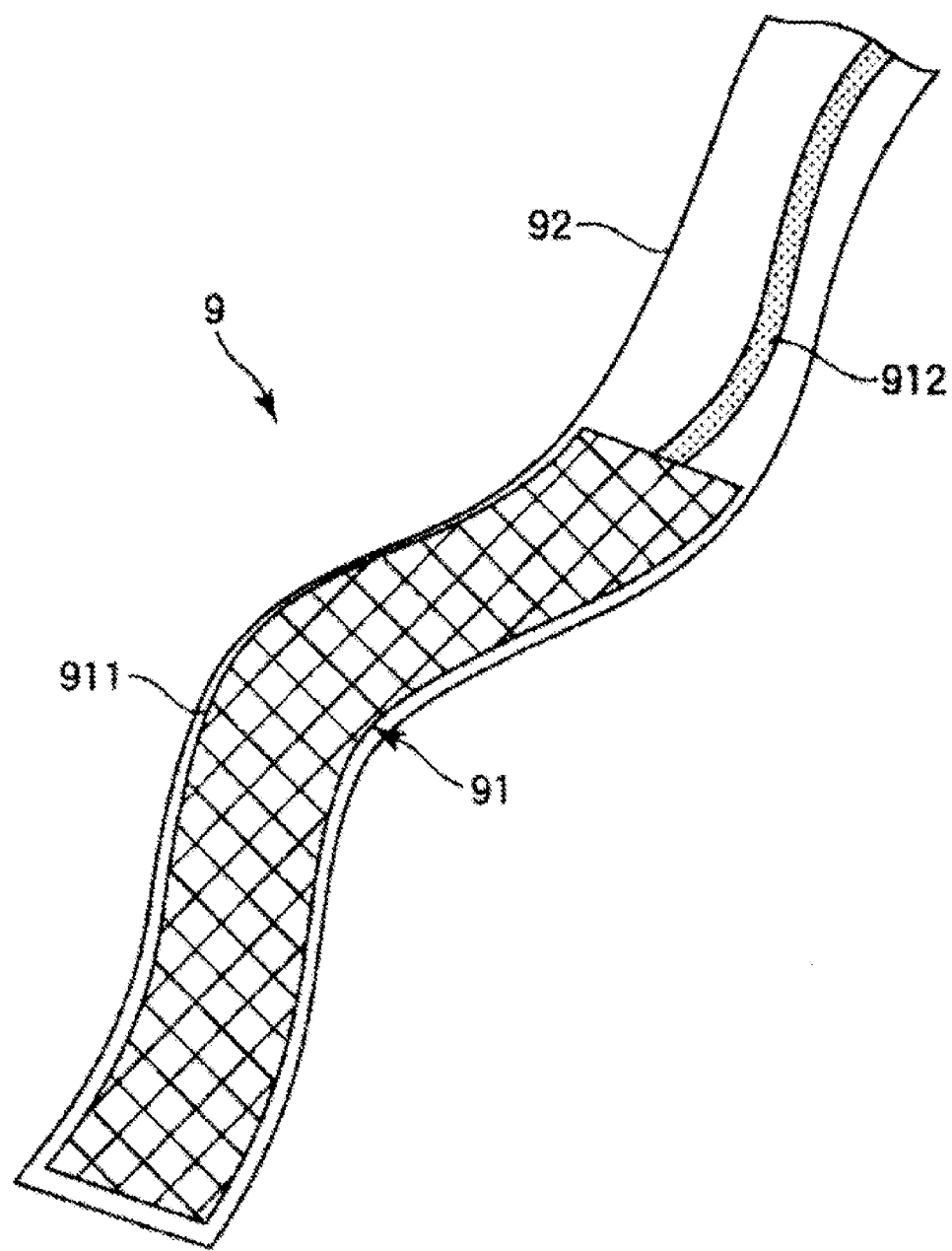
FIG. 13 is a view depicting an implant used together with the puncture device depicted in FIG. 1.

The implant (living body tissue supporting indwelling) 9 depicted in FIG. 13 is a tool which can be embedded for the treatment of urinary incontinence of a female, for example, a tool which supports, for example, when the urethra 1300 tries to move to the vaginal wall side, the urethra 1300 so as to restrict the movement of the urethra 1300 in a direction away from the vaginal wall. For the implant 9, for example, an elongated article having flexibility can be used.

The implant 9 has an implant main body 91, and a bag-shaped packaging material 92 which accommodates the implant main body 91. Further, the implant main body 91 has a main body portion 911, and a pair of strips 912 and 913 connected to the both ends of the main body portion 911. Where the implant 9 can include the packaging material 92, pollution of the implant main body 91 can be prevented effectively. It is to be noted that a guide wire, a rope, a thread or the like may be used in place of the strips 912 and 913.

The main body portion 911 has a form of a net and has a strip-like general shape. It is to be noted that the main body portion 911 can be configured from an article formed by crossing linear objects with each other into a braid, for example, a net-like braid. The linear objects may be those having a circular transverse sectional shape, or those having a flattened transverse sectional shape, for example, those of strip-like shape.

The constituent material of each of the main body portion 911, strips 912 and 913 and packaging material 92 is not limited particularly, and various resin materials, fiber and so forth having biocompatibility such as, for example, polypropylene, polyester elastomer and or nylon can be used.

It is to be noted that the implant 9 is not limited to such a net-like one as described above as long as it exhibits similar effects.

Now, an operation procedure of the puncture device 1, for example, a procedure when the implant 9 is to be embedded into the living body, is described.

Figure 14A:
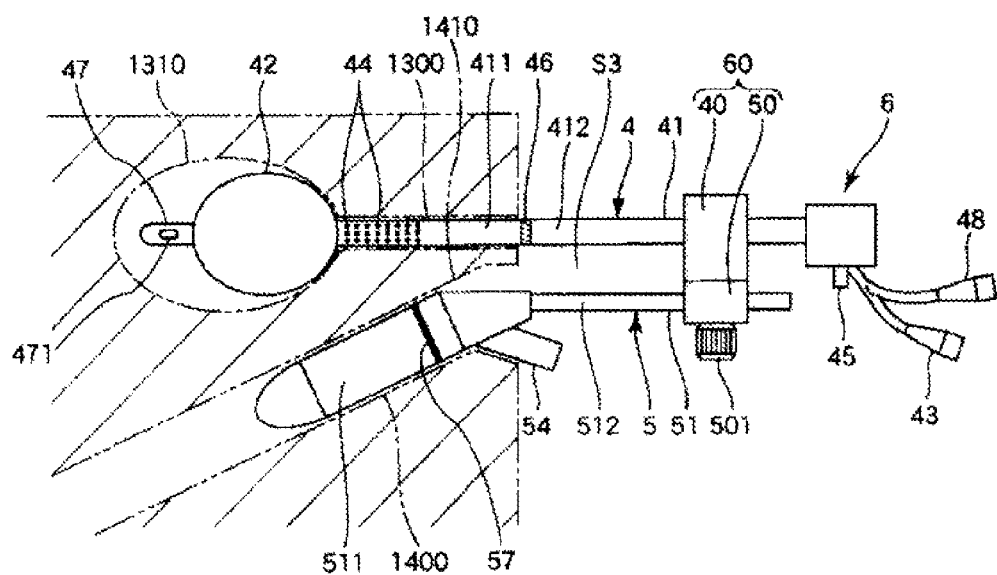
FIGS. 14(*a*) and 14(*b*) are views illustrating an operation procedure of the puncture device depicted in FIG. 1.

First, a patient is caused to assume a lithotomy position on an operating table, and the insertion tool 6 is mounted on the patient as depicted in FIG. 14(a). In accordance with an exemplary embodiment, for example, the urethral insertion portion 41 of the urethral insertion member 4 is inserted into the urethra 1300 of the patient. Thereupon, the insertion depth is measured with the marker 46 to dispose the balloon 42 in the bladder 1310. Then, the balloon 42 is expanded and, as occasion demands, the urine is discharged from within the bladder 1310 through the discharge hole 471. Further, the vaginal insertion portion 51 of the vaginal insertion member 5 is inserted into the vagina 1400 of the patient. Thereupon, the insertion depth is determined with the marker 57 to insert the vaginal insertion portion 51 to an appropriate depth. Then, the male thread 501 is operated to fix the supporting portions 40 and 50. The mounting of the insertion tool 6 on the patient is completed thereby. In this state, the non-insertion portions 412 and 512 are spaced away from each other and the supporting portion 60 is spaced away from the body surface between the urethral orifice and the vaginal orifice. Consequently, the body surface is exposed. In addition, the insertion portion 511 and the vaginal front wall are spaced away from each other, and a gap (space) is formed between them. Consequently, a space S3 through which a syringe 2000 is to puncture the living body tissue between the urethra 1300 and the vagina 1400 from the body surface between the urethral orifice and the vaginal orifice is formed.

Then, suction devices are connected to the suction ports 45 and 54 and rendered operative to absorb the urethral rear wall to the urethral insertion portion 41 and absorb the vaginal front wall to the vaginal insertion portion 51. For example, if the urethral rear wall is absorbed precisely to the urethral insertion portion 41, then since the suction hole 44 is closed up with the urethral wall, the suction from the suction port 45 is stopped or weakened. Similarly, if the vaginal front wall is absorbed precisely to the vaginal insertion portion 51, then since the suction hole 59 is closed up with the vaginal wall, the suction from the suction port 54 is stopped or weakened. Therefore, from the absorption degree from the suction ports 45 and 54 (for example, from the magnitude of sound generated by the suction), it can be determined whether or not the urethral rear wall and the vaginal front wall are absorbed precisely to the urethral insertion portion 41 and the vaginal insertion portion 51, respectively. It is to be noted that the insertion tool 6 may have a verification mechanism for allowing mechanical verification of the absorption state. Although the verification mechanism is not limited particularly if the absorption state can be determined therefrom, it may be configured, for example, such that it has a flow rate measurement unit (negative pressure gauge) for measuring the flow rate from the suction port 54 and a decision unit which decides on the basis of a measurement result from the flow rate measurement unit whether or not the absorption can be precisely carried out.

After it is confirmed that the urethral rear wall and the vaginal front wall are absorbed precisely to the urethral insertion portion 41 and the vaginal insertion portion 51, respectively, the insertion tool 6 is further pushed into the distal end side (into the living body). Consequently, since the urethra 1300 (bladder 1310) and the vagina 1400 are pushed in together with the insertion tool 6, the urethra 1300, bladder 1310, vagina 1400 and so forth can be retracted with a higher degree of certainty from the puncture passage of the puncture member 3.

Figure 14B:
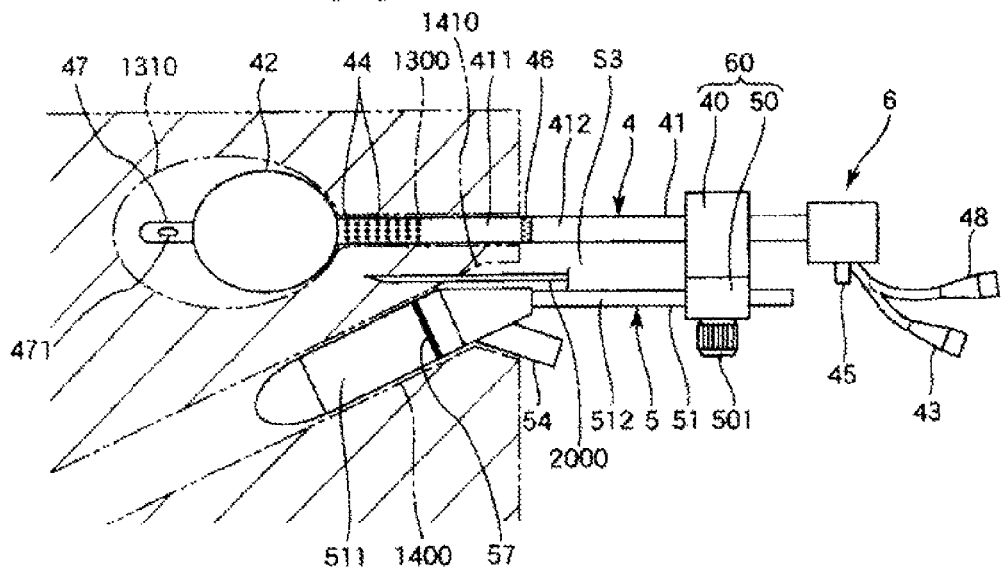

Then, humoral peeling off is carried out. In accordance with an exemplary embodiment, for example, the puncture needle of the syringe 2000 is caused to puncture through the space (space S3) between the insertion portion 511 and the vaginal front wall as depicted in FIG. 14(*b*), and liquid of saline solution or local anesthetic is injected into the living body tissue between the urethra 1300 and the vagina 1400 (between the regions S1 and S2). Consequently, the living body tissue between the regions S1 and S2 are expanded, and the urethral rear wall is pressed against the urethral insertion portion 41 while the vaginal front wall is pressed against the vaginal insertion portion 51.

Here, preferably the suction from the suction holes 44 and 59 is continuously carried out also during the humoral peeling off. When the urethral rear wall is pressed against the urethral insertion portion 41 by the humoral peeling off, since the urethral rear wall is further absorbed to the urethral insertion portion 41, the suction from the suction port 45 is stopped or weakened. Similarly, when the vaginal front wall is pressed against the vaginal insertion portion 51, it is further absorbed to the vaginal insertion portion 51, and therefore, the suction from the suction port 45 is stopped or weakened. Accordingly, the operator can determine in accordance with the absorption degrees from the suction ports 45 and 54 whether or not the humoral peeling off has been precisely carried out.

Figure 15:
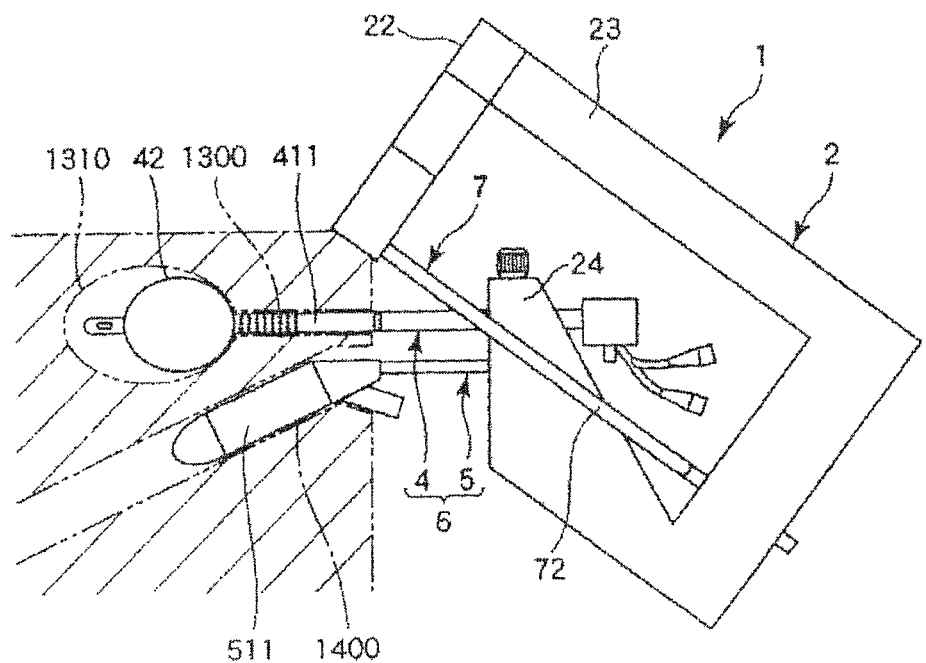
FIG. 15 is a view illustrating the operation procedure of the puncture device depicted in FIG. 1.
Figure 16:
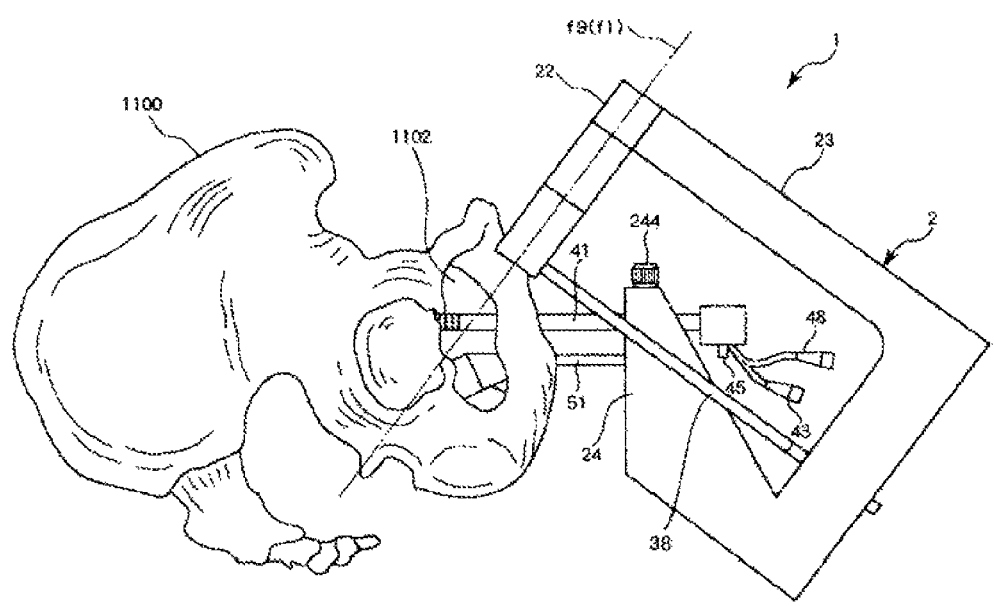
FIG. 16 is a view illustrating the operation procedure of the puncture device depicted in FIG. 1.

After the humoral peeling off is carried out and the urethral rear wall and the vaginal front wall are placed into a state in which they are spaced away from each other sufficiently, the frame 2 is fixed to the insertion tool 6 as depicted in FIG. 15. Consequently, the puncture device 1 is placed into a state in which it is mounted on the patient. In this state, the positional relationship between the pelvis 1100 and the puncture device 1 has such a state as depicted in FIG. 16.

Figure 17:
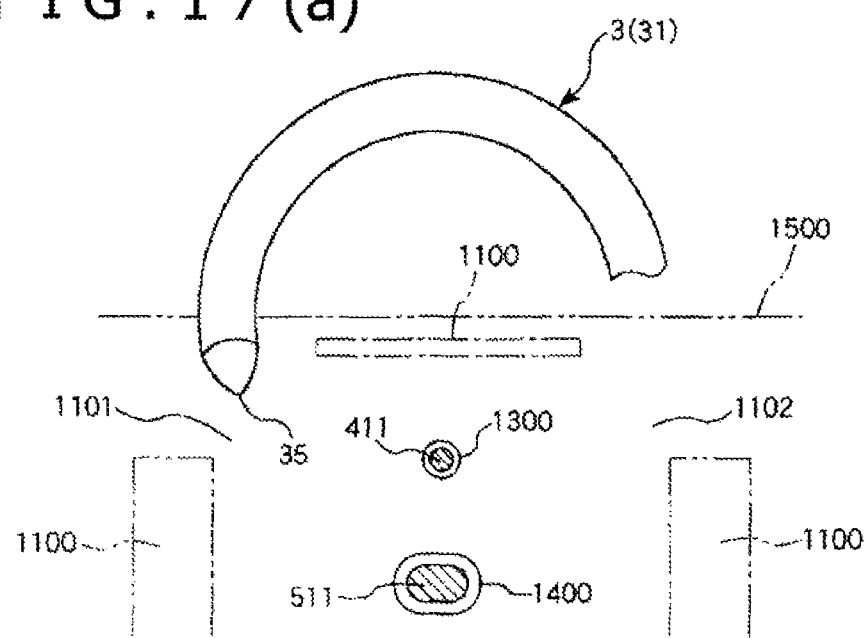
FIGS. 17(*a*) and 17(*b*) are views illustrating the operation procedure of the puncture device depicted in FIG. 1.
Figure 17:
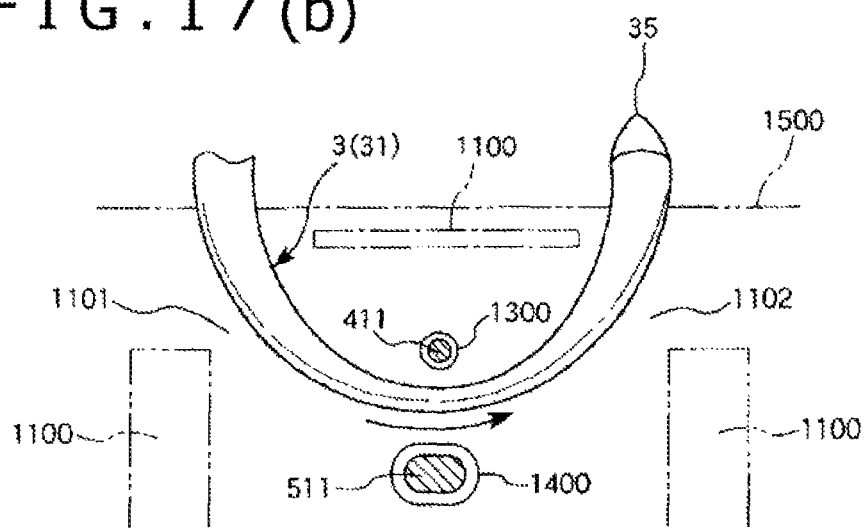
Figure 18:
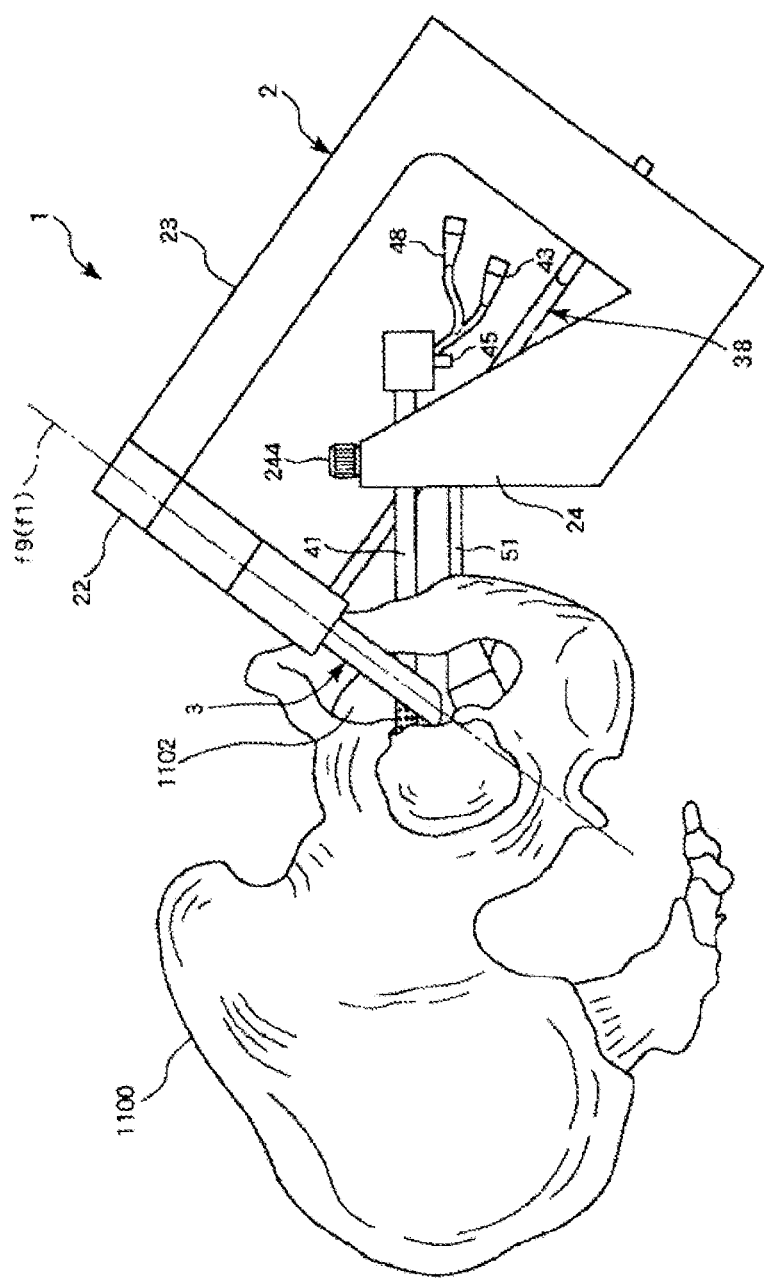
FIG. 18 is a view illustrating the operation procedure of the puncture device depicted in FIG. 1.

Then, for example, while the connection portion 23 of the frame 2 is gripped by one hand, the connection portion 38 of the puncture member 3 is gripped by the other hand to turn the puncture member 3 in the counterclockwise direction as depicted in FIGS. 17(*a*) and 17(*b*). Consequently, the needle tip 35 of the puncture member 3 punctures the body surface 1500 of the right side inguinal region or a location (first location) in the proximity of the right side inguinal region of the patient and enters the inside of the body, passes the obturator foramen 1101, a region between the urethra 1300 and the vagina 1400 and the other obturator foramen 1102 in order, projects to the outside of the body from the body surface 1500 at the left side inguinal region or a location (second location) in the proximity of the left side inguinal region, and is finally retracted into the guide portion 22 (refer to FIG. 18).

Figure 19:
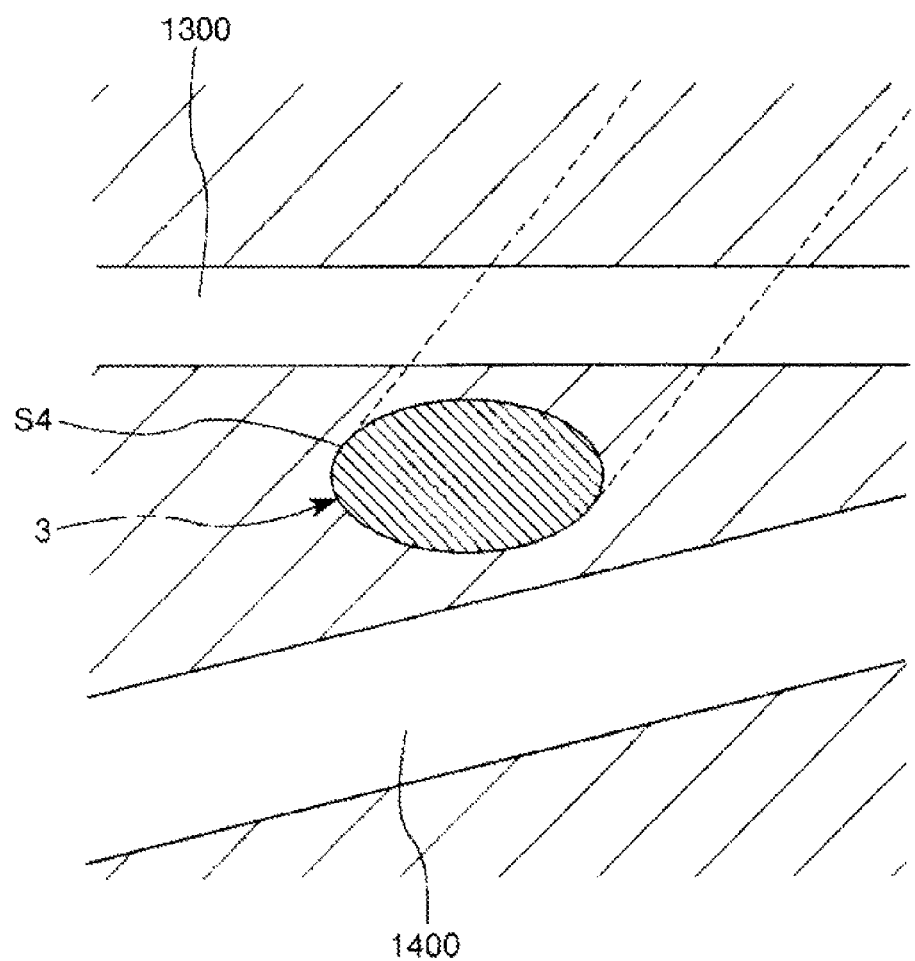
FIG. 19 is a view illustrating the operation procedure of the puncture device depicted in FIG. 1.

Consequently, a puncture hole is formed in the living body as a result of the passage of the puncture member 3 therethrough. In this state, central portion S4 is disposed such that the width W1 thereof (direction of the longitudinal axis of the transverse section) extends substantially in parallel to the urethra 1300 as depicted in FIG. 19.

Then, the puncture member 3 is turned in the reverse direction, for example, in the clockwise direction. Consequently, the puncture needle 31 is removed from the living body. Then, the puncture device 1 is removed from the patient.

Thereafter, the implant main body 91 is taken out from the packaging material 92 and, for example, using a guide wire, the guide wire is threaded into the puncture hole before placing the implant main body 91 into a state in which it is embedded in the living body. In this state, the main body portion 911 is disposed substantially in parallel to the urethra 1300 in the region between the urethra 1300 and the vagina 1400. Therefore, the urethra 1300 can be supported over a wide area by the implant main body 91.

Figure 20:
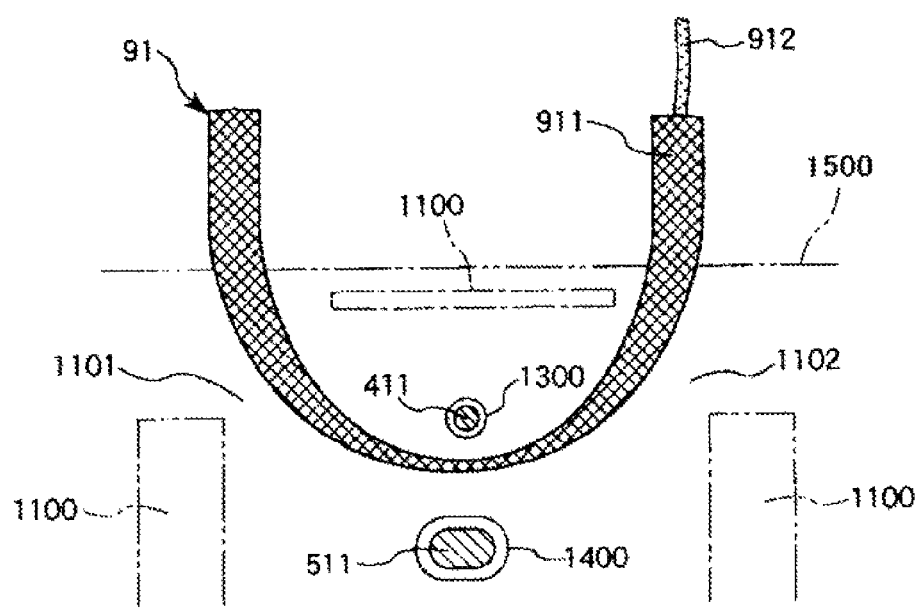
FIG. 20 is a view illustrating the operation procedure of the puncture device depicted in FIG. 1.

Then, as depicted in FIG. 20, the strips 912 and 913 are pulled to finely adjust the position of the main body portion 911 with respect to the urethra 1300, and then an unnecessary portion of the implant main body 91 is cut away, thereby ending the manipulation.

As described above, with the puncture device 1, when the implant 9 is to be indwelled, the indwelling can be coped only with the manipulation of low invasion such as puncture of the puncture member 3 and a highly invasive incision need not be carried out. Therefore, the burden on the patient can be reduced and the safety of the patient can be relatively high.

Further, since the inclination angle θ2 is restricted within the numerical range given hereinabove, the implant main body 91 threaded in the puncture hole can be embedded in parallel to the urethra 1300 with certainty. Consequently, the urethra 1300 can be supported over a wide area.

Further, the living body can be punctured by the puncture member 3 avoiding the urethra 1300 and the vagina 1400, and the puncture member 3 can be prevented from puncturing the urethra 1300 or the vagina 1400, which is relatively safe.

Further, such a situation that the implant 9 is exposed to the inside of the vagina from a wound generated by incision as in the case in which the vagina is incised in a conventional manner or such complications that infection is caused through the wound occur can be prevented. This is very safe, and the implant 9 can be embedded with relative certainty.

In the following, the second embodiment of the puncture device of the present disclosure is described with reference to FIGS. 21(*a*) and 21(*b*). However, description is given principally of differences from the embodiment described hereinabove, and description of similar matters is omitted herein.

The present embodiment is similar to the first embodiment described hereinabove except that it is different in configuration of the puncture member.

Figure 21:
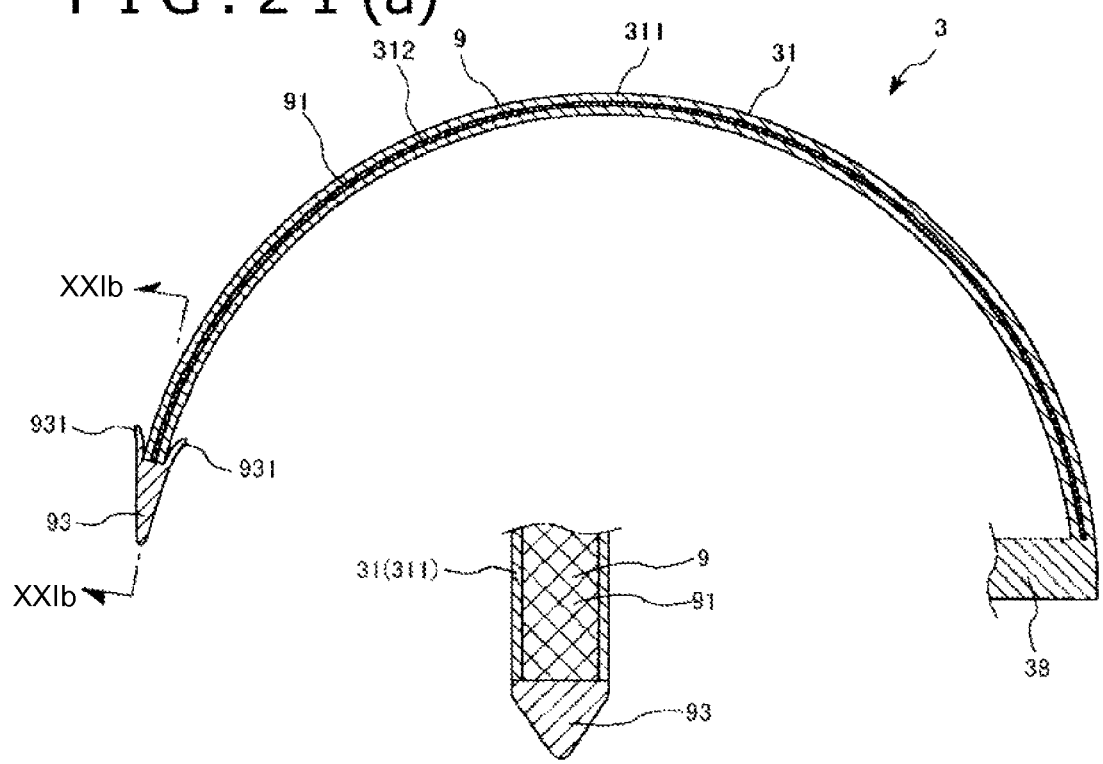
FIG. 21(*a*) is a cross sectional view of a puncture member of another puncture device (second embodiment) of the present disclosure.

As depicted in FIGS. 21(*a*) and 21(*b*), the puncture needle 31 is configured from an assembly of a hollow body 311 of a tubular shape having a hollow portion 312 and an implant 9 accommodated in the hollow portion 312. A removable needle tip unit 93 is provided at the distal end of the hollow portion 312.

The implant 9 is connected to the needle tip unit 93 through a strip 912 at a distal end portion of the implant main body 91. This needle tip unit 93 has an apex portion formed as a needle tip for puncturing the living body tissue.

A pair of projections 931 are formed on an outer peripheral portion of a proximal end portion of the needle tip unit 93 in such a manner as to project in a direction toward the proximal end. The projections 931 are disposed so as to oppose to each other across the center axis of the puncture needle 31. Further, the proximal end sides of the projections 931 are more spaced apart from each other compared to that of the distal end sides. Consequently, the needle tip unit 93 can be prevented from returning to an opposite direction to the puncturing direction of the needle tip unit 93, and an anchor effect can be achieved.

Further, the implant 9 has, at a proximal end portion of the implant main body 91 thereof, a holding member 95 which is connected thereto through a strip 913.

In such a puncture needle 31 as described above, if the puncture needle 31 is operated in the reverse direction after it punctures the living body tissue, the projections 931 are engaged with the living body tissue. Consequently, the hollow body 311 is pulled away from the living body tissue while the implant 9 remains indwelled in the living body tissue.

Figure 22:
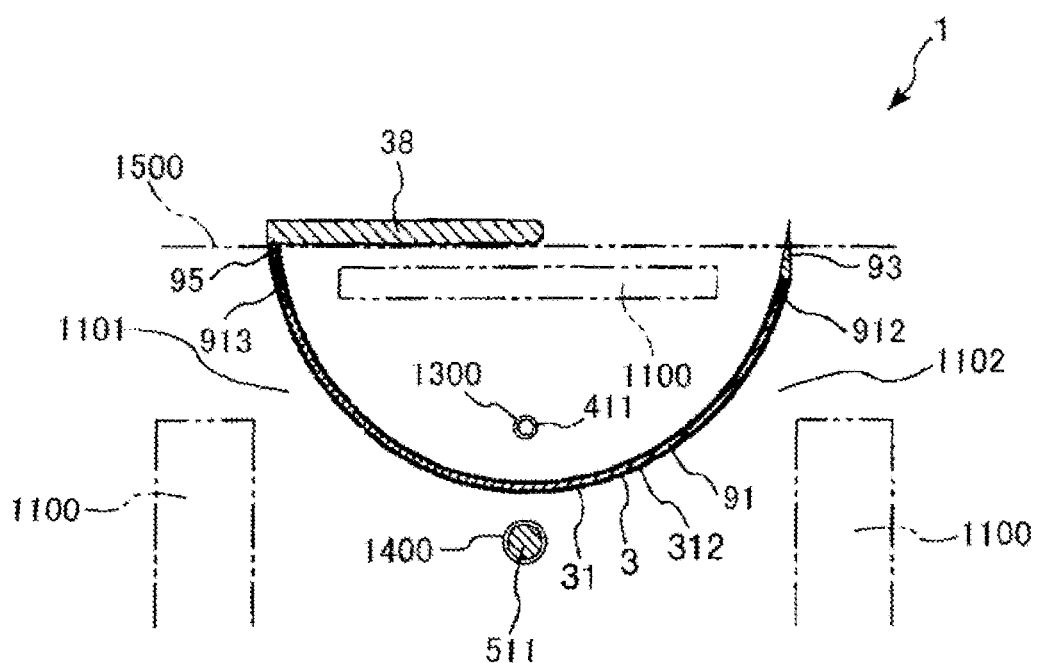
FIG. 22 is a view illustrating an operation procedure of a further puncture device (third embodiment) of the present disclosure.
Figure 23:
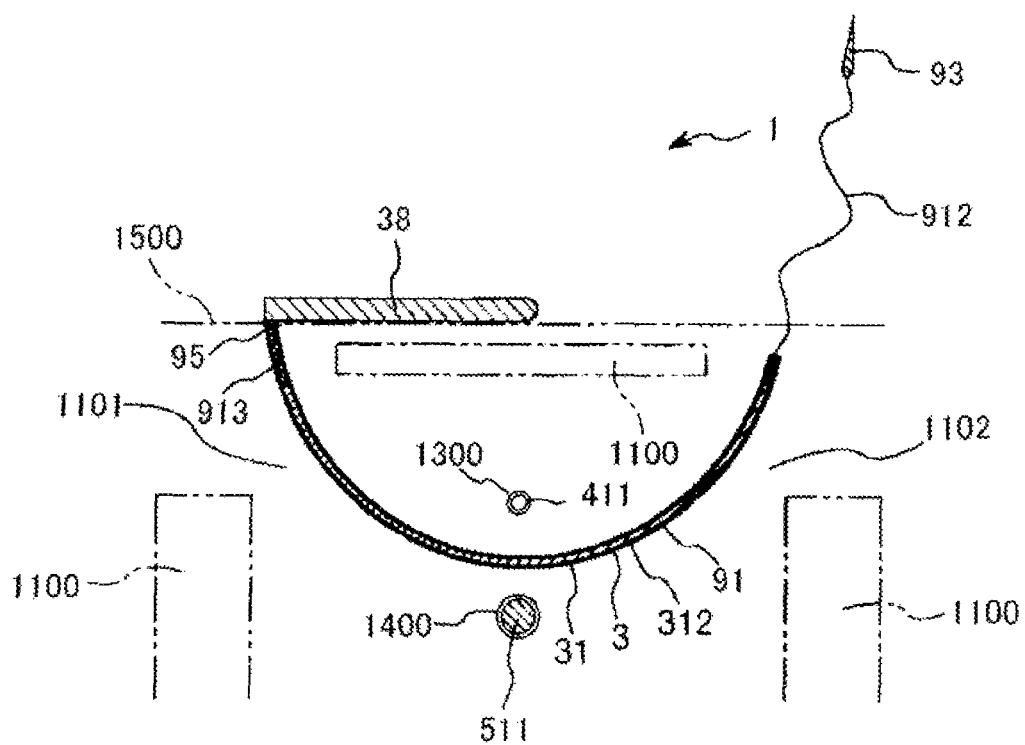
FIG. 23 is a view illustrating the operation procedure of the puncture device (third embodiment) of the present disclosure.
Figure 24:
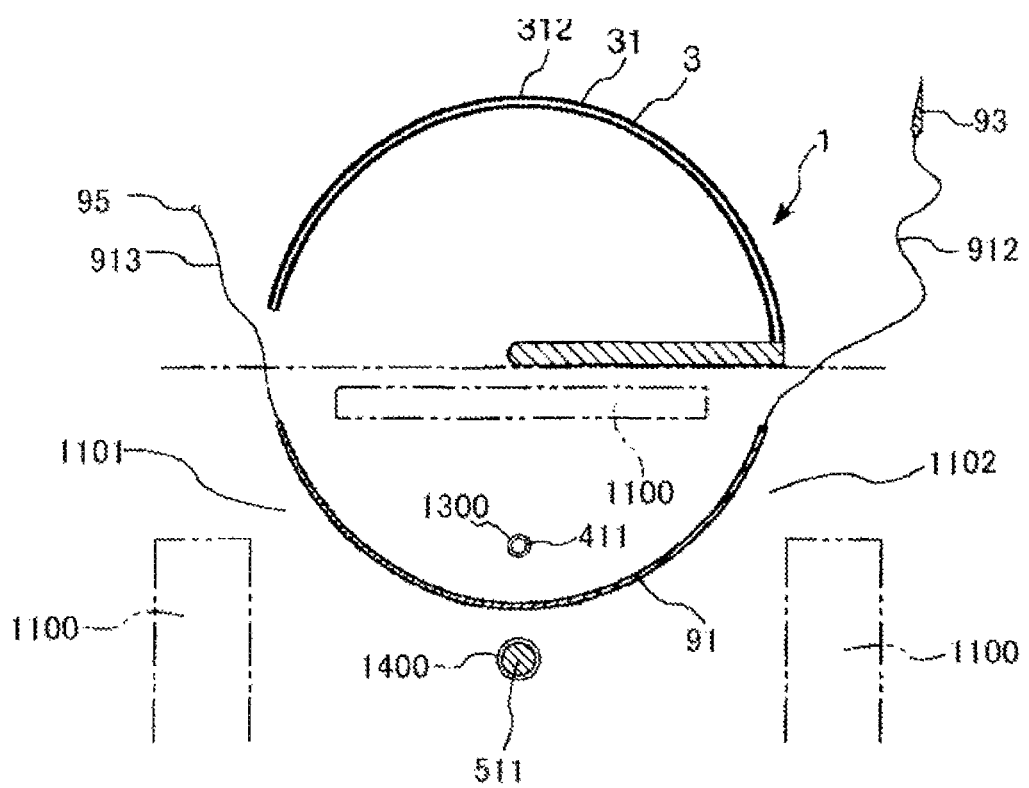
FIG. 24 is a view illustrating the operation procedure of the puncture device (third embodiment) of the present disclosure.

FIGS. 22 to 24 are views illustrating an operation procedure of a puncture device (third embodiment) of the present disclosure.

In the following, the third embodiment of the puncture device of the present disclosure is described with reference to FIGS. 22 to 24. However, description is given principally of differences from the embodiments described hereinabove, and description of similar matters is omitted herein.

The present embodiment is similar to the second embodiment except that it is different in configuration of the puncture member.

In an operation procedure of the puncture device 1 of the present embodiment, the puncture device 1 is first placed into a mounted state similarly as in the first embodiment.

Then, the puncture needle 31 is turned in the counterclockwise direction as depicted in FIG. 22. Consequently, the needle tip unit 93 punctures the body surface 1500 at the right side inguinal region or a location in the proximity of the right side inguinal region of the patient and enters the inside of the body. Then, the needle tip unit 93 passes through the obturator foramen 1101, between the urethra 1300 and the vagina 1400 and through the other obturator foramen 1102 in order, and projects to the outside of the body through the body surface 1500 at the left side inguinal region or a location in the proximity of the left side inguinal region.

Thereafter, the needle tip unit 93 is removed from the distal end portion of the puncture needle 31 as depicted in FIG. 23. The strip 912 connected to the needle tip unit 93 is drawn out from the puncture needle 31.

Then, the puncture needle 31 is turned in the clockwise direction as depicted in FIG. 24. The puncture needle 31 is drawn out to the outside of the body thereby. Further, the holding member 95 is removed from the distal end of the hollow portion 312 of the puncture needle 31. The strip 913 connected to the holding member 95 is drawn out from the puncture needle 31.

Thereafter, the puncture device 1 is taken out from the patient.

Thereafter, the position of the implant main body 91 with respect to the urethra 1300 is adjusted and an unnecessary portion of the implant main body 91 is cut away, thereby ending the manipulation. The implant main body 91 (implant 9) is embedded into the living body in this manner.

In the following, the fourth embodiment of the puncture device of the present disclosure is described with reference to FIGS. 25 to 28. However, description is given principally of differences from the embodiments described hereinabove, and description of similar matters is omitted herein.

The present embodiment is similar to the first embodiment described hereinabove except that it is different in configuration of the puncture member.

Figure 25:
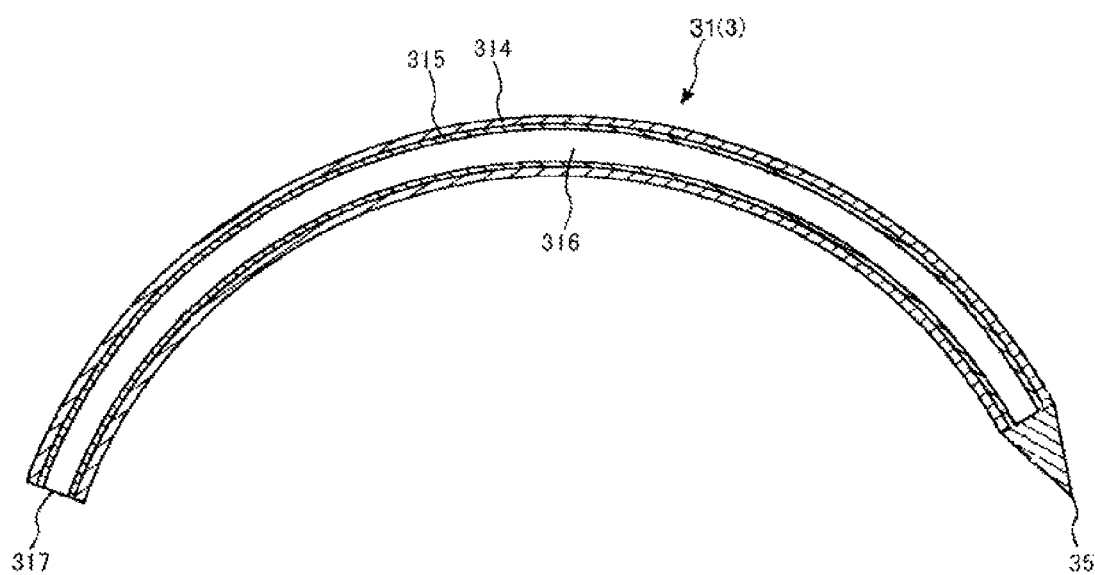
FIG. 25 is a cross sectional view of a puncture member of a puncture device (fourth embodiment) of the present disclosure.

As depicted in FIG. 25, the puncture needle 31 is configured as an assembly of a hollow needle main body 314 and an extension needle 315 inserted in the needle main body 314 and having a needle tip 35. The extension needle 315 is provided for relative movement to the needle main body 314 along a longitudinal direction of the needle main body 314. The puncture needle 31 configured as such an assembly is extended by moving the extension needle 315 in a direction toward the distal end of the needle main body 314 with respect to the needle main body 314. Further, the puncture device 1 can include, as extension means for moving the extension needle 315 in the direction toward the distal end of the needle main body 314 with respect to the needle main body 314 to extend the puncture needle 31, a pusher 7 for pushing the extension needle 315 to move in the direction toward the distal end of the needle main body 314.

Figure 26:
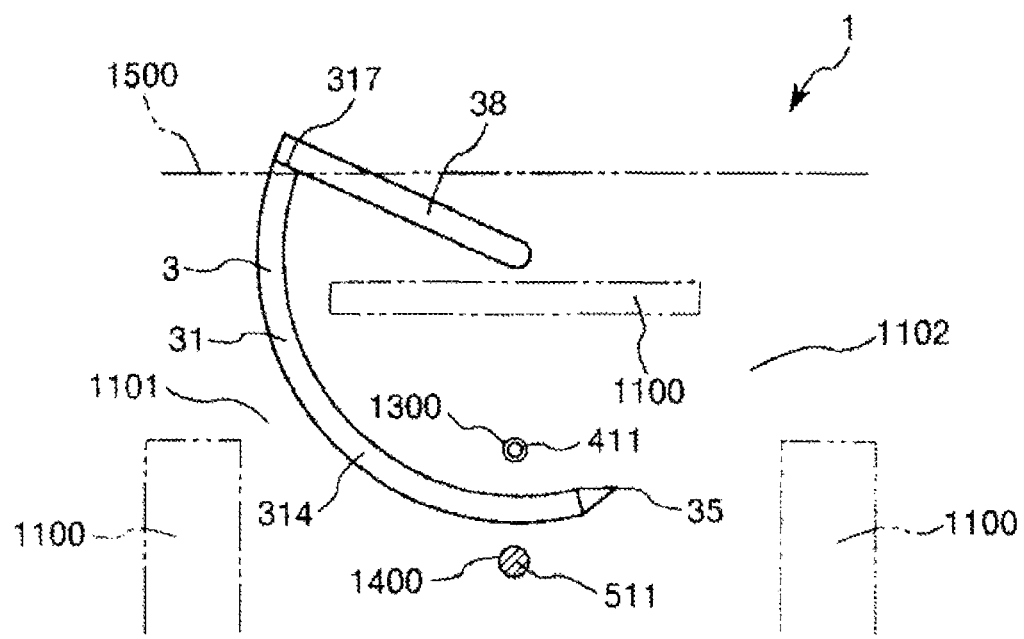
FIG. 26 is a view illustrating an operation procedure of the puncture device depicted in FIG. 25.
Figure 27:
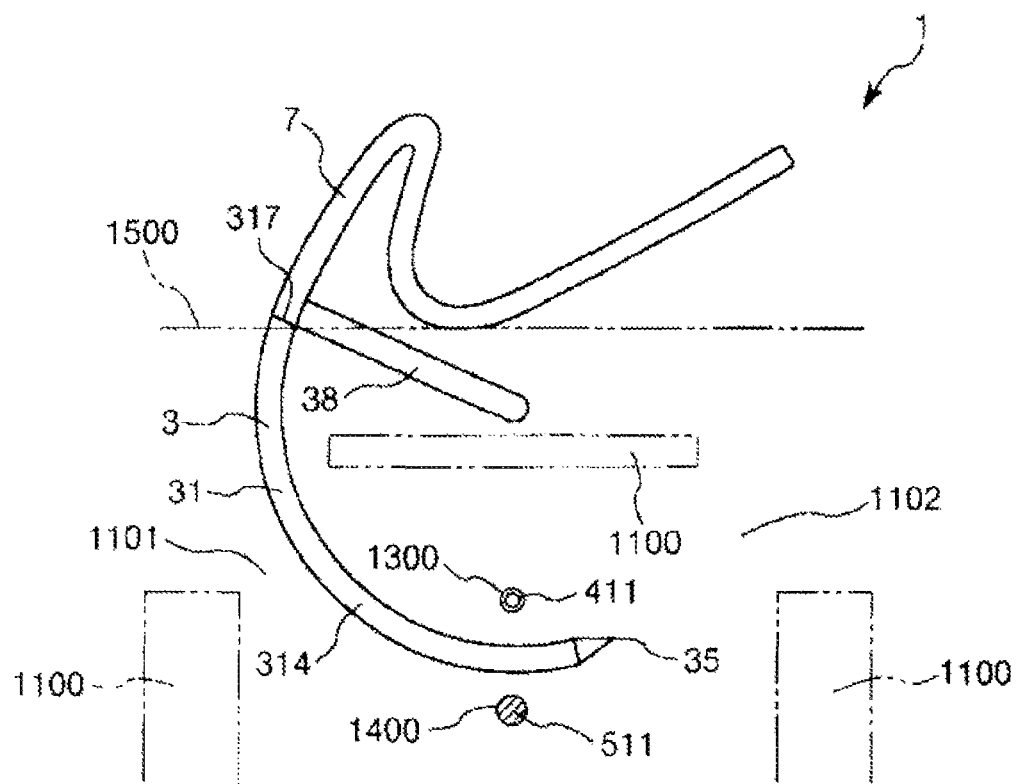
FIG. 27 is a view illustrating the operation procedure of the puncture device depicted in FIG. 25.
Figure 28:
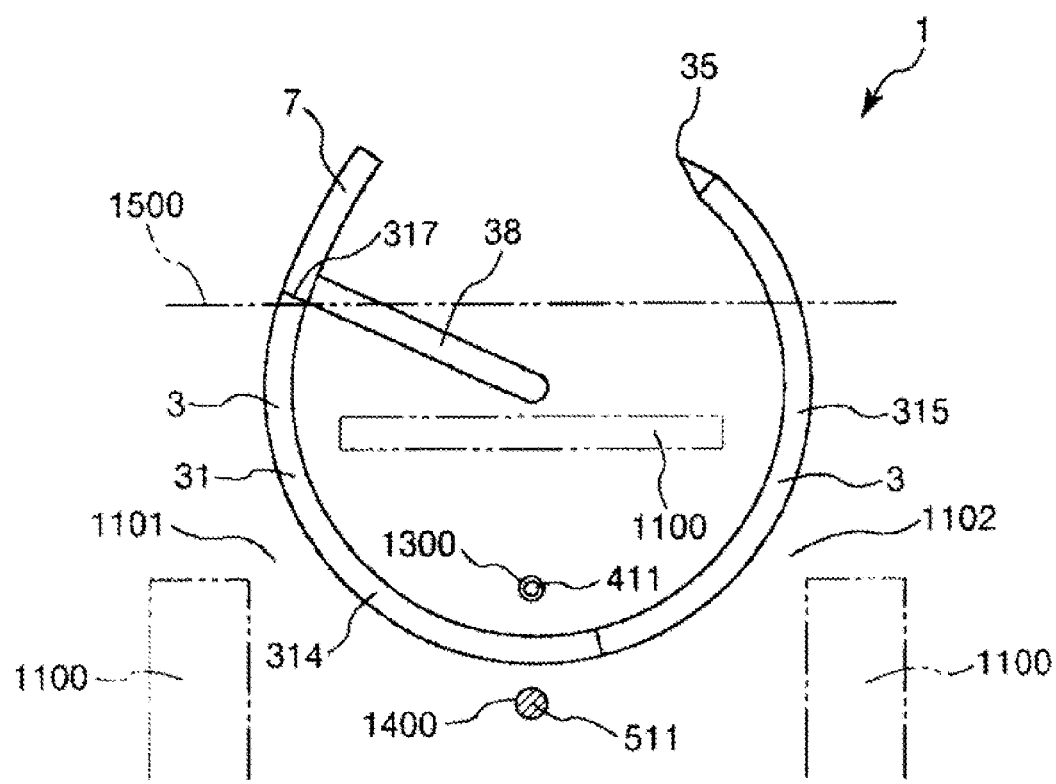
FIG. 28 is a view illustrating the operation procedure of the puncture device depicted in FIG. 25.

It is to be noted that the puncture needle 31 can assume a first state (initial state) depicted in FIGS. 25 to 27 and a state depicted in FIG. 28. In the first state, the extension needle 315 is positioned on the most proximal end side with respect to the needle main body 314, and the needle tip 35 is exposed already (projects). In the second state, the extension needle 315 has moved in the direction toward the distal end with respect to the needle main body 314, and the entire puncture needle 31 is extended. While the center angle of the puncture needle 31 in this state is suitably set in accordance with various conditions, it is set such that, when the puncture needle 31 punctures the living body tissue, it can enter the inside of the body from one portion of the body surface 1500 of the patient, pass below the urethra 1300 and project to the outside of the body from another portion of the body surface 1500. The center angle of the puncture needle 31 preferably is set, for example, to 190 to 270 degrees, and more preferably is 200 to 250 degrees.

The extension needle 315 is hollow, and a hollow portion 316 has an opening 317 open at the proximal end. The opening 317 configures an entrance for the pusher 7 when the pusher 7 is to be inserted into the hollow portion 316.

The pusher 7 is elongated, and is inserted into the hollow portion 316 of the extension needle 315 from the opening 317 and pushes a distal end portion of the extension needle 315 to move the extension needle 315 in the direction toward the distal end. The transverse sectional shape of the pusher 7 corresponds to the transverse sectional shape of the hollow portion 316 of the extension needle 315. Further, the pusher 7 has flexibility so that it is compatible with the shape of the needle main body 314 and the extension needle 315. It is to be noted that, since the distal end portion of the extension needle 315 is closed, the distal end portion of the pusher 7 can be contacted with the distal end portion of the extension needle 315 and push the distal end portion of the extension needle 315.

Now, an operation procedure of the puncture device 1 of the present embodiment is described.

First, the puncture device 1 is placed into a mounted state similarly as in the first embodiment described hereinabove.

Then, the puncture needle 31 is turned in the counterclockwise direction in the first state as depicted in FIG. 26. Consequently, the needle tip 35 punctures the body surface 1500 at the right side inguinal region or in the proximity of the right side inguinal region of the patient and enters the body until it comes to a position between the obturator foramen 1101 and urethra 1300 and the vagina 1400.

Then, as depicted in FIGS. 27 and 28, the pusher 7 is inserted from the opening 317 of the extension needle 315 into the hollow portion 316, and the extension needle 315 is pushed at the distal end portion thereof in the direction toward the distal end by the pusher 7 so that the extension needle 315 is moved in the direction toward the distal end. Consequently, the puncture needle 31 is placed into the second state. Then, the needle tip 35 passes the other obturator foramen 1102 in order and projects to the outside of the body from the body surface 1500 at the left side inguinal region or a region in the proximity of the left side inguinal region.

Thereafter, the puncture needle 31 is turned in the clockwise direction in FIGS. 27 and 28 while it remains in the second state. Consequently, the puncture needle 31 is pulled out to the outside of the body. Thereafter, the puncture device 1 is taken out from the patient.

Then, the implant main body 91 is inserted into a puncture hole formed by the puncture needle 31, and an unnecessary portion of the implant main body 91 is cut away, whereby ending the manipulation.

The device and the method for inserting the implant main body 91 into the puncture hole can be suitably selected in addition to those in the present embodiment. For example, they can be implemented by: inserting, where a sheath is mounted on the puncture needle 31 in advance, an implant into the sheath indwelled at a predetermined place directly or through some other tool as in sixth and ninth embodiments; puncturing in a state in which an implant is inserted in advance in a hollow puncture needle and turning the puncture needle in the reverse direction to indwell the implant in the puncture hole as in the second and third embodiments; indwelling, where the distal end of a puncture needle has a structure capable of coupling the puncture needle to an implant main body or a member connecting to the implant main body, the implant into the puncture hole by turning the puncture needle in the reverse direction as in the fifth and eighth embodiments; or inserting, after puncture of a puncture needle, a sheath from the needle tip and inserting an implant into the sheath after the puncture needle is pulled out as in the seventh embodiment.

In the following, the fifth embodiment of the puncture device of the present disclosure is described with reference to FIGS. 29 to 31. However, description is given principally of differences from the embodiments described hereinabove, and description of similar matters is omitted herein.

The present embodiment is similar to the first embodiment described hereinabove except that it is different in configuration of the puncture member.

Figure 29:
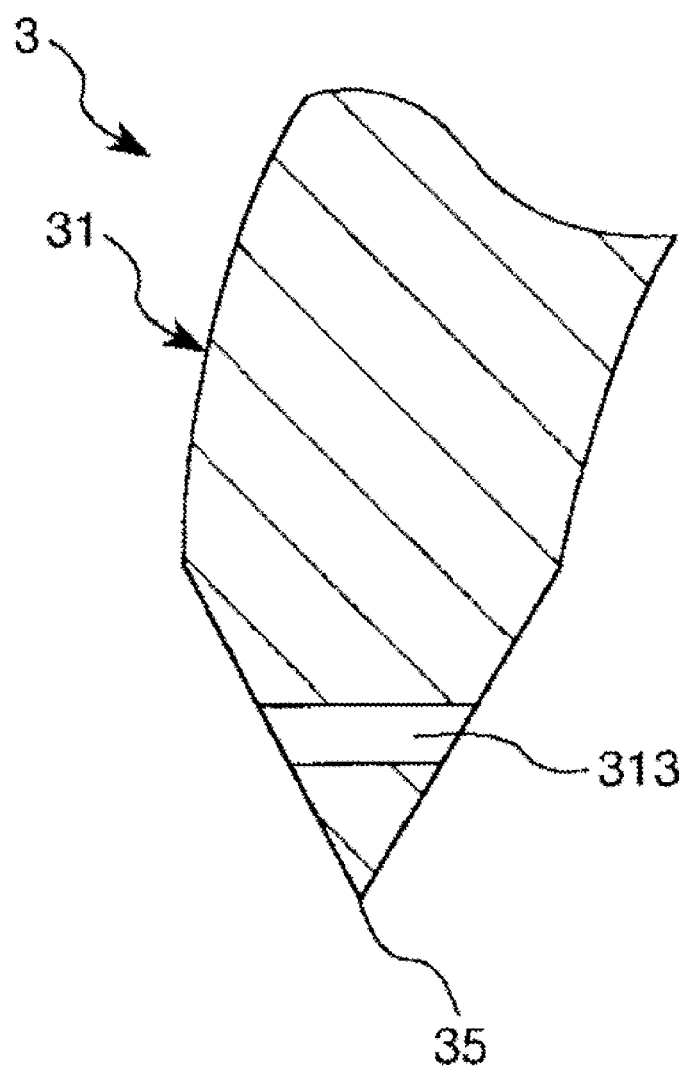
FIG. 29 is a cross sectional view of a puncture member of a puncture device (fifth embodiment) of the present disclosure.

As depicted in FIG. 29, a puncture needle 31 can include, in the proximity of a needle tip 35 thereof, a mechanism which allows mounting of one of strips 912 and 913 of an implant main body. In accordance with an exemplary embodiment, for example, a through-hole 313 is formed in the puncture needle 31 in the proximity of the needle tip 35 such that it extends through the puncture needle 31 in a direction orthogonal to the center axis of the puncture needle 31. One of the strips 912 and 913 of the implant main body 91 is inserted into the through-hole 313. Consequently, the implant main body 91 is engaged with the puncture needle 31. Further, by pulling out the implant main body 91, the implant main body 91 is released from the puncture needle 31.

Now, an operation procedure of the puncture device 1 of the present embodiment is described.

First, similarly as in the first embodiment, the puncture device 1 is placed into a mounted state, and in this state, the puncture member 3 is operated to turn until the needle tip 35 projects from the body surface 1500 to expose the through-hole 313.

Figure 30:
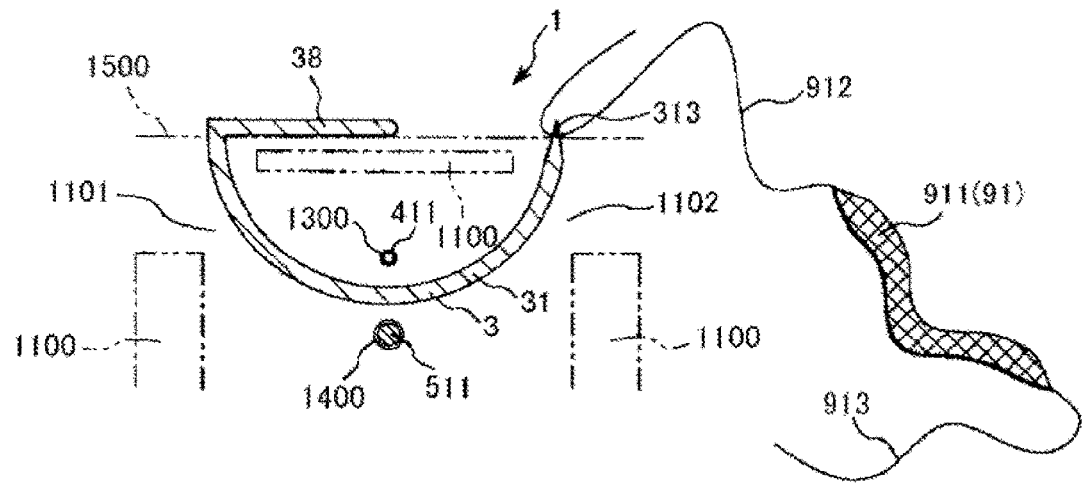
FIG. 30 is a view illustrating an operation procedure of the puncture device depicted in FIG. 29.

Then, the implant main body 91 or an extension of the implant main body 91 is held at the distal end of the puncture needle 31 as depicted in FIG. 30. In accordance with an exemplary embodiment, for example, one of the strips 912 and 913 fixed to the implant main body 91, in the configuration depicted, the strip 912, is threaded at an end portion thereof into the through-hole 313 of the puncture needle 31. Consequently, the end portion of the strip 912 is held at the distal end portion of the puncture needle 31.

Figure 31:
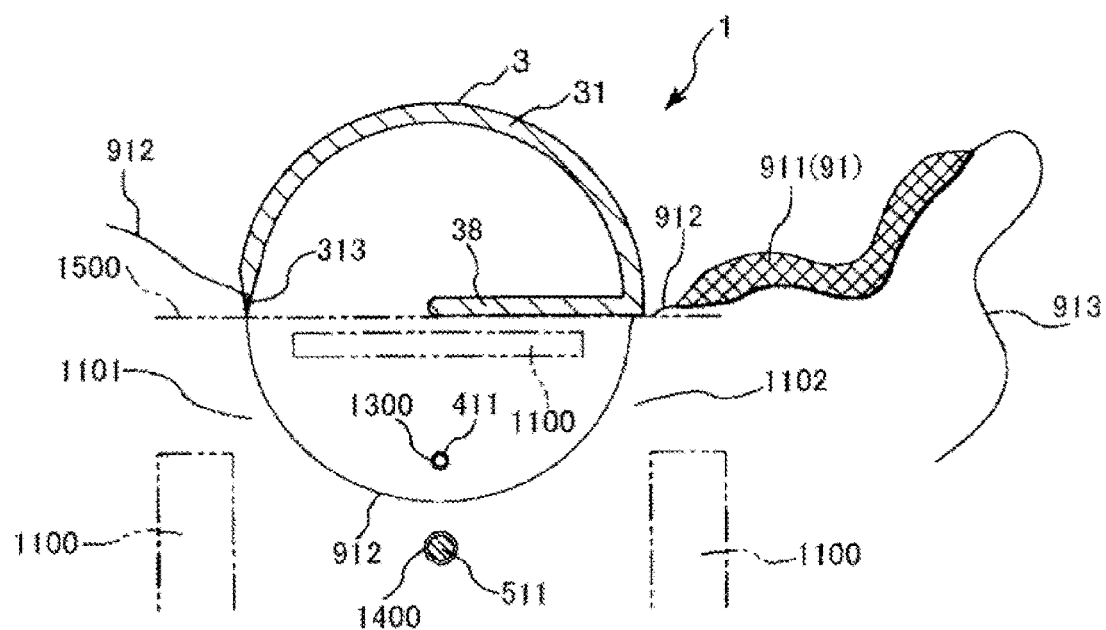
FIG. 31 is a view illustrating the operation procedure of the puncture device depicted in FIG. 29.

Then, the puncture member 3 is turned in the clockwise direction as depicted in FIG. 31. Consequently, the puncture needle 31 is pulled out to the outside of the body and the strip 912 is drawn and pulled out from the obturator foramen 1101 side.

Then, the holding between the implant main body 91 or the extension of the implant main body 91 and the distal end of the puncture needle 31 is canceled. In accordance with an exemplary embodiment, for example, the end portion of the strip 912 is pulled out from the through-hole 313 of the puncture needle 31. Further, the puncture device 1 is removed from the patient.

Thereafter, the strips 912 and 913 are pulled in the opposite directions to each other to adjust the position of the implant main body 91 with respect to the urethra 1300, and an unnecessary portion of the implant main body 91 is cut away, thereby ending the manipulation. The implant main body 91 (implant 9) is embedded into the living body in this manner.

In the following, the sixth embodiment of the puncture device of the present disclosure is described with reference to FIGS. 32 to 40. However, description is given principally of differences from the embodiment described hereinabove, and description of similar matters is omitted herein.

The present embodiment is similar to the first embodiment described hereinabove except that it further can include an implant assembly.

As depicted in FIGS. 32 to 36, the puncture device 1 can include an outer tube 30. The outer tube 30 is in a state in which the puncture needle 31 of the puncture member 3 is fitted and mounted therein (first state depicted in FIGS. 32 and 33), and in a state in which the puncture needle 31 is removed (second state depicted in FIGS. 35 and 36), a guide wire 600 or the like can be inserted into the outer tube 30.

It is to be noted that the outer tube 30 preferably is of the rigid type. In this case, the outer tube 30 is formed entirely as a curved portion which is curved arcuately similarly to the puncture needle 31. Here, the "rigid" signifies a degree by which the outer tube 30 itself can maintain the arcuately curved state. Further, the cross sectional shape of the outer tube 30 is a flattened shape similarly to the transverse sectional shape of the puncture needle 31.

The outer tube 30 has a distal end opening 301 open at the distal end thereof, and a proximal end opening 302 open at the proximal end thereof.

Further, a tapering portion 303 is formed on an outer peripheral portion of a distal end portion of the outer tube 30 such that it has a tapering angle equal to the tapering angle of the puncture needle 31 from the needle tip 35. In the first state, the outer tube 30 can turn together with the puncture needle 31 to puncture (penetrate) the living body readily (refer to FIG. 33).

Further, a flange portion 304 having an expanded outer diameter is formed on an outer peripheral portion of a proximal end portion of the outer tube 30. For example, if the flange portion 304 is contacted with the body surface 1500 (living body surface) in the state depicted in FIG. 33, then the limit of the turning of the puncture needle 31 in the direction toward the distal end is restricted, and therefore, the living body can be punctured in just proportion.

The constituent material of the outer tube 30 is not limited particularly, and, for example, various resin materials such as polyethylene and polypropylene, and various metal materials such as stainless steel, aluminum or aluminum alloy, titanium or titanium alloy can be used.

Further, in the puncture device 1, an implant assembly 100 can be used.

Figure 38:
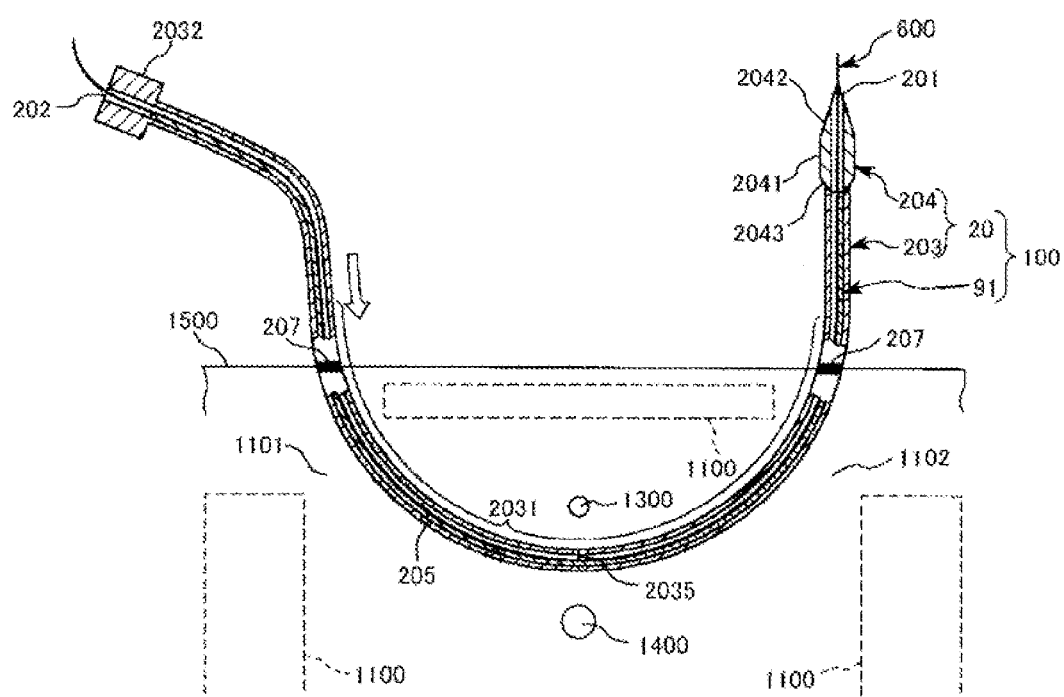
FIG. 38 is a view illustrating the operation procedure of the puncture device (sixth embodiment) of the present disclosure.
Figure 39:
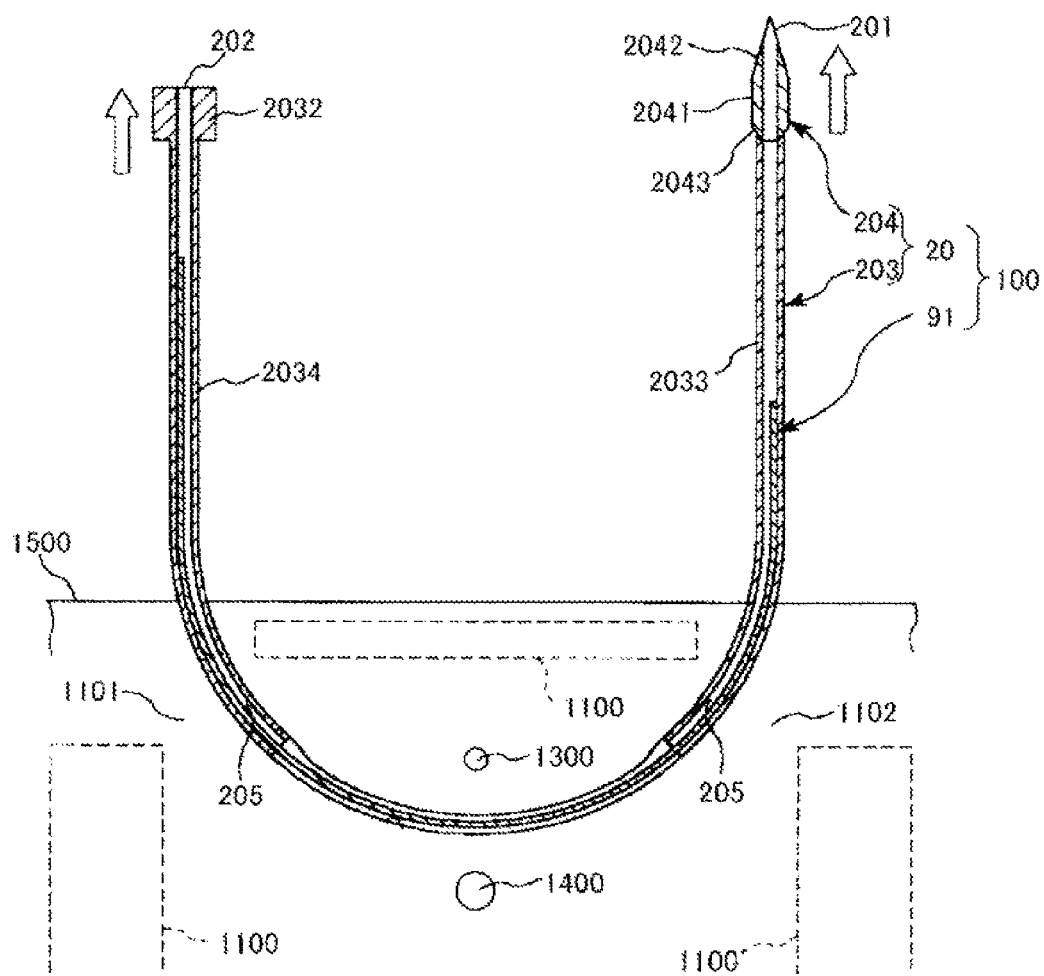
FIG. 39 is a view illustrating the operation procedure of the puncture device (sixth embodiment) of the present disclosure.

As depicted in FIGS. 38 and 39, the implant assembly 100 can include a medical tube (tube) 20, and an implant main body 91 which is inserted into the medical tube 20.

The medical tube 20 is a tube having a distal end opening 201 open at the distal end thereof and a proximal end opening 202 open at the proximal end thereof. In addition, the medical tube 20 can be divided into an elongated tube main body 203 and a head portion 204 provided at a distal end portion of the tube main body 203. The medical tube 20 has a lumen 205 formed therein which extends through the tube main body 203 and the head portion 204, for example, is open to the medical tube 20 and the proximal end opening 202. The implant main body 91 can be inserted into the lumen 205.

As depicted in FIG. 38, the tube main body 203 has a curved portion 2031 curved arcuately at an intermediate portion in the longitudinal direction thereof. In the medical tube 20, at least the curved portion 2031 is of the rigid type. Here, the "rigid" signifies a degree by which the curved portion 2031 itself can maintain the arcuately curved state. Further, the degree of the curve (curvature) of the curved portion 2031 is similar to that of the curve of the puncture needle 31 of the puncture device 1.

By such a configuration as described above, when the medical tube 20 (implant assembly 100) is to be inserted into a puncture hole formed by the puncture needle 31, it can help prevent the curved portion 2031 from being crushed (compressed) in the puncture hole and allows the curved portion 2031 to follow (extend along) the curved shape of the puncture hole readily. Consequently, an operation for inserting the medical tube 20 into the puncture hole (living body) together with the implant main body 91 can be carried out readily and with certainty. Further, by separating the medical tube 20 as hereinafter described after the insertion operation, the implant main body 91 can be indwelled readily and with certainty in the puncture hole (refer to FIGS. 39 and 40).

Further, the transverse sectional shape of the tube main body 203 is a flattened shape similarly to that of the puncture needle 31. Consequently, when the implant main body 91 of a shape of a strip is inserted into the lumen 205 in advance, the insertion operation can be readily carried out. Further, a space can be formed to allow the implant main body 91 to be inserted with relative certainty into the puncture hole, and the direction of the implant main body 91 can be regulated.

Further, a flange portion 2032 having an increased outer diameter is formed at a proximal end portion of the tube main body 203. It is to be noted that the flange portion 2032 can be omitted.

As depicted in FIG. 39, the tube main body 203 (medical tube 20) is configured for separation at an intermediate portion of the tube main body 203 in the longitudinal direction, and is therefore separated into a first tube 2033 on the distal end side and a second tube 2034 on the proximal end side. By the separation, the medical tube 20 can be pulled out relatively rapidly from the puncture hole, and consequently, only the implant main body 91 is indwelled in the puncture hole.

As depicted in FIG. 38, the separation portion 2035 is disposed at a central location of the curved portion 2031 in the longitudinal direction. Consequently, when the tube main body 203 is separated at the separation portion 2035 as depicted in FIG. 39, the urethra 1300 can be supported suitably on the implant main body 91. It is to be noted that the configuration of the separation portion 2035 is not limited particularly, and may have, for example, a configuration by a reduced-width fragile portion, another configuration by a fitting portion or a like configuration.

Preferably, a marker 207 for allowing a central portion of the curved portion 2031 in the longitudinal direction to be grasped is applied to a distal end portion and a proximal end portion of the tube main body 203 (refer to FIG. 38). By the markers 207, the position of a central portion of the curved portion 2031 in the longitudinal direction, for example, of the separation portion 2035, can be grasped with certainty. It is to be noted that, although the marker 207 is provided at both of the distal end portion and the proximal end portion of the tube main body 203, the provision of the marker 207 is not limited to them, and the marker 207 may be provided, for example, at one of the distal end portion and the proximal end portion of the tube main body 203.

As depicted in FIGS. 38 and 39, the head portion 204 is configured from a cylindrical body. It is to be noted that the head portion 204 may be configured integrally with the tube main body 203 or may be configured from a member separate from the tube main body 203 and bonded to the tube main body 203.

The head portion 204 has, provided midway in the longitudinal direction thereof, an increased diameter portion 2041 having an increased outer diameter. Further, a portion of the head portion 204 on the distal end side from the increased diameter portion 2041 is formed as a tapering portion 2042 having an outer diameter gradually decreasing in a direction toward the distal end. In addition, a portion of the head portion 204 on the proximal end side from the increased diameter portion 2041 is formed as a tapering portion 2043 having an outer diameter gradually decreasing in a direction toward the proximal end. It is to be noted that the overall length of the tapering portion 2042 is longer than the overall length of the tapering portion 2043.

Where the head portion 204 has such a shape as described above, the medical tube 20 can be readily inserted into the puncture hole from the head portion 204 side.

It is to be noted that the width of the tube main body 203 having a transverse section of a flattened shape is equal to or greater than the outer diameter of the head portion 204 which has a circular transverse sectional shape. Consequently, as the medical tube 20 is inserted into the puncture hole, it expands the puncture hole with the tube main body 203 thereof. In other words, the living body can be detached.

Now, an operation procedure of the puncture device 1 of the present embodiment is described.

Figure 32:
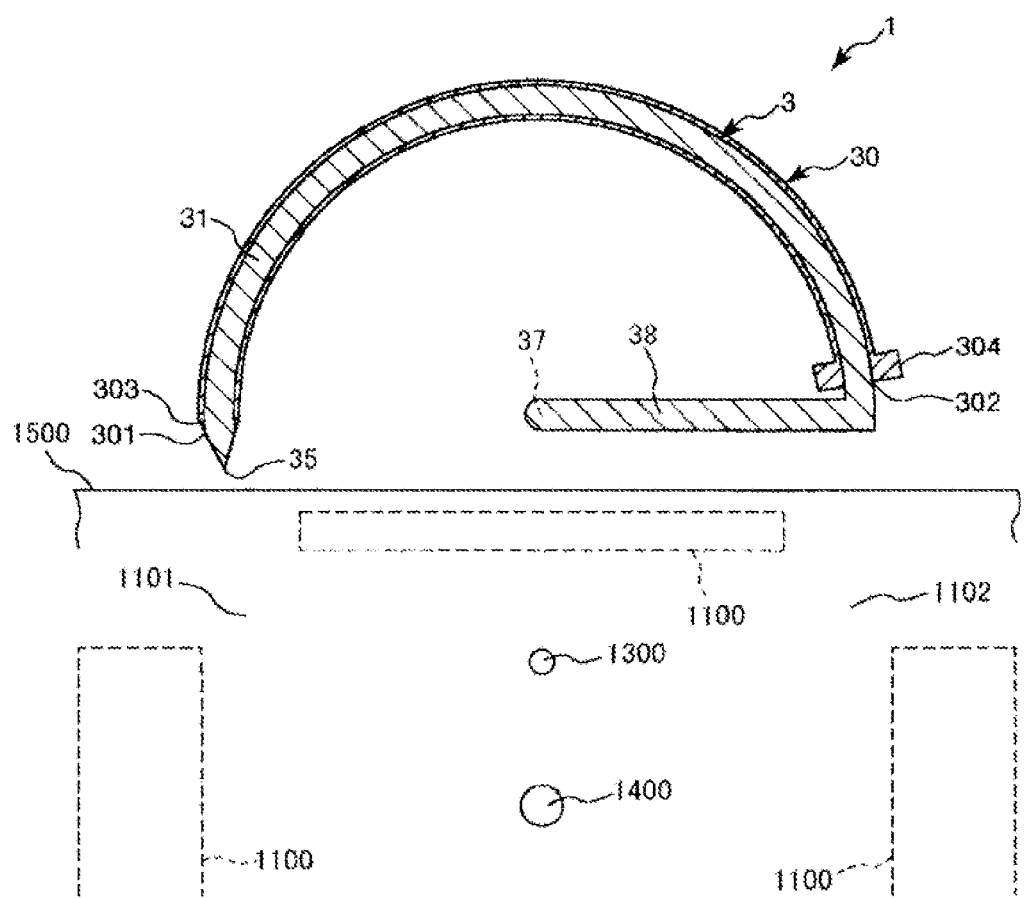
FIG. 32 is a view illustrating an operation procedure of a puncture device (sixth embodiment) of the present disclosure.

First, the puncture device 1 is placed into a mounted state as depicted in FIG. 32 similarly as in the first embodiment. In this state, the puncture needle 31 is in the first state.

Figure 33:
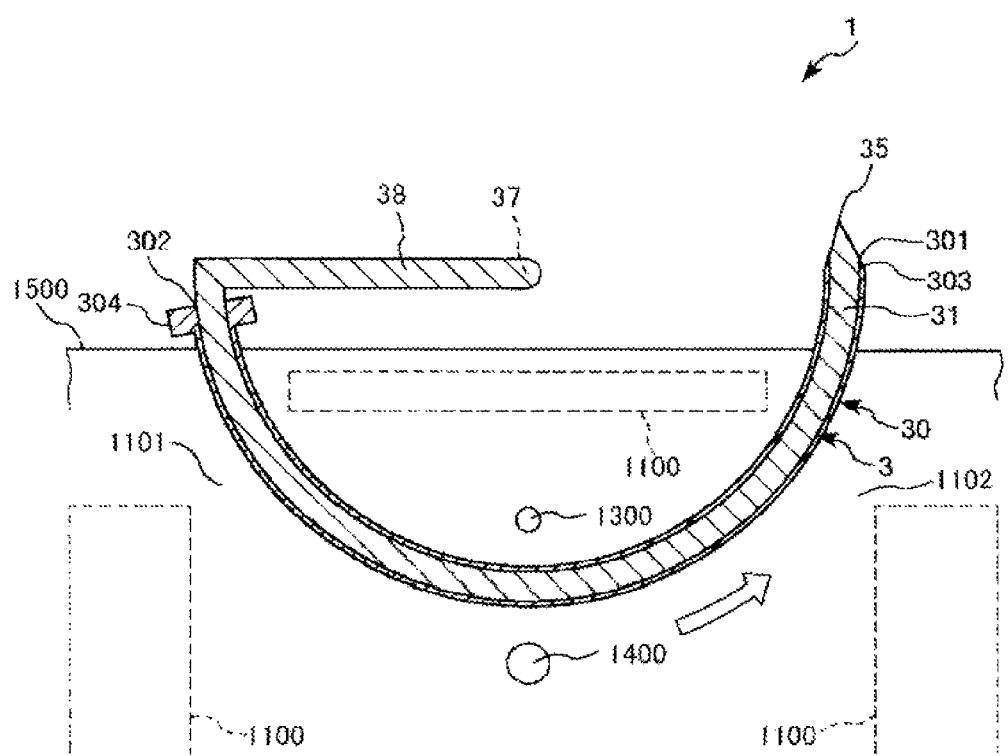
FIG. 33 is a view illustrating the operation procedure of the puncture device (sixth embodiment) of the present disclosure.

Then, the puncture member 3 is turned in the counter-clockwise direction as depicted in FIG. 33. Consequently, the puncture needle 31 turns around the center of turning provided by the shaft portion 37 to puncture the body surface 1500 together with the outer tube 30 at the right side inguinal region or a region in the proximity of the right side inguinal region of the patient to enter the body. Then, the puncture needle 31 passes through the obturator foramen 1101, between the urethra 1300 and the vagina 1400 and through the other obturator foramen 1102, whereafter it projects to the outside of the body from the body surface 1500 at the left side inguinal region or a region in the proximity of the left side inguinal region.

Figure 34:
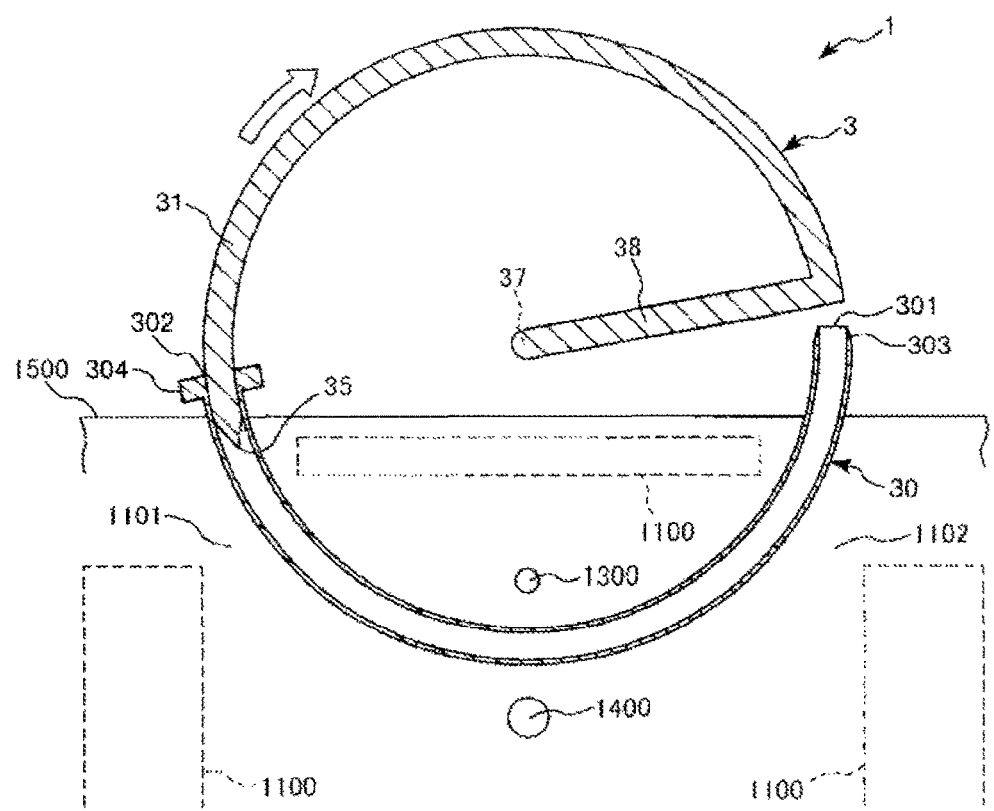
FIG. 34 is a view illustrating the operation procedure of the puncture device (sixth embodiment) of the present disclosure.

Then, the puncture member 3 is turned reversely, for example, in the clockwise direction, as depicted in FIG. 34. Consequently, the puncture needle 31 of the puncture member 3 is pulled out from the outer tube 30. Meanwhile, the outer tube 30 remains indwelled in the living body.

Figure 35:
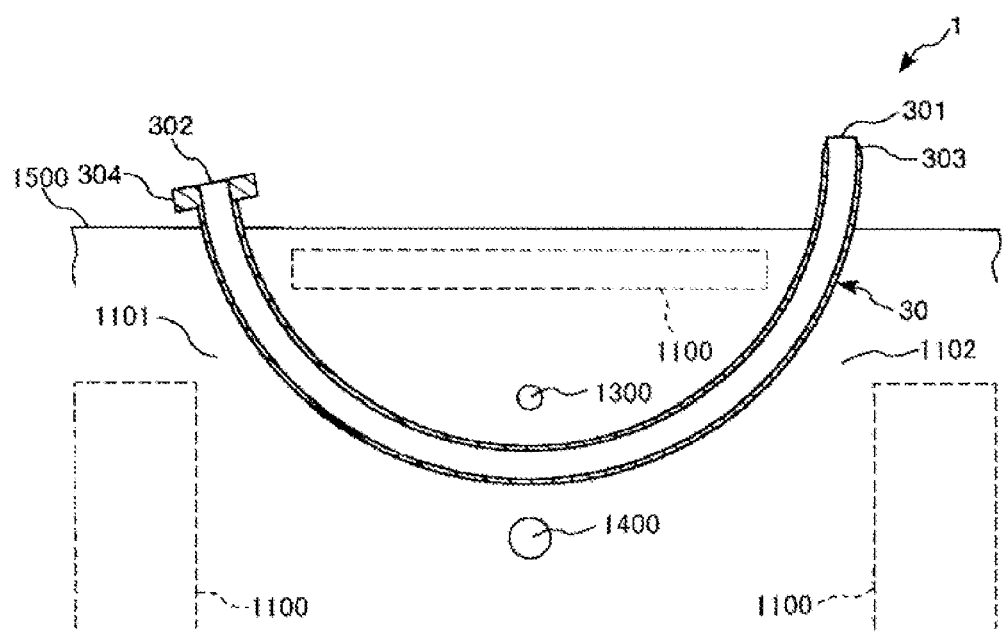
FIG. 35 is a view illustrating the operation procedure of the puncture device (sixth embodiment) of the present disclosure.

Thereafter, the puncture device 1 is removed from the body surface 1500 as depicted in FIG. 35.

Figure 36:
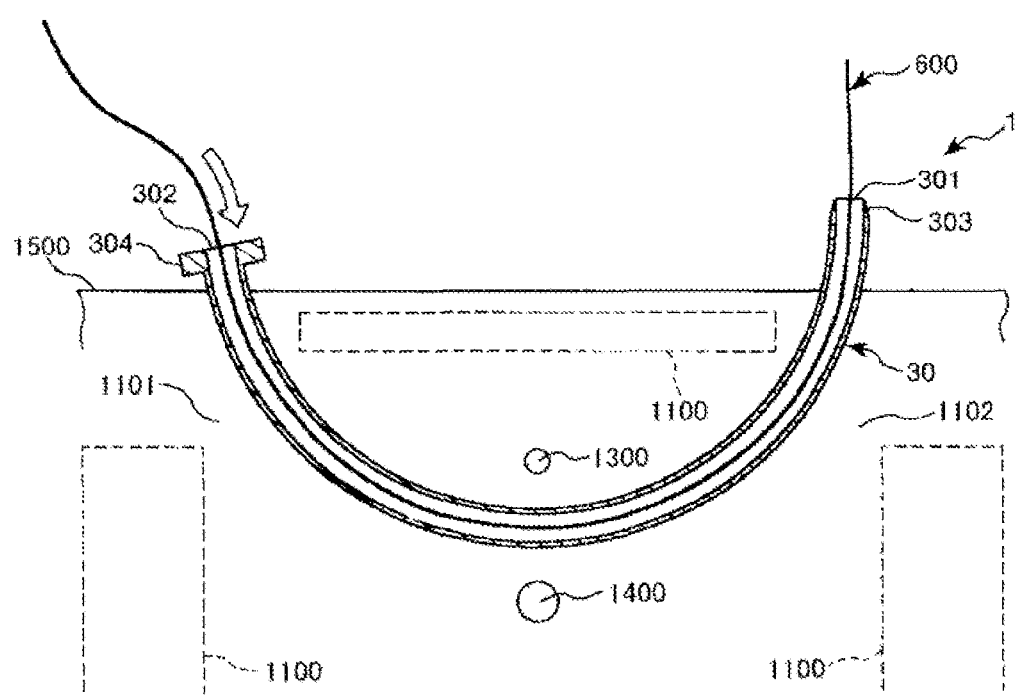
FIG. 36 is a view illustrating the operation procedure of the puncture device (sixth embodiment) of the present disclosure.

Then, a guide member is threaded into the outer tube 30 indwelled in the living body as depicted in FIG. 36. For example, the guide wire 600 is threaded into the outer tube 30 indwelled in the living body. Consequently, the guide wire 600 is placed into a state in which it projects, at a portion thereof on the distal end side, from the distal end opening 301 of the outer tube 30 and it projects, at a portion thereof on the proximal end side, from the proximal end opening 302 of the outer tube 30.

Figure 37:
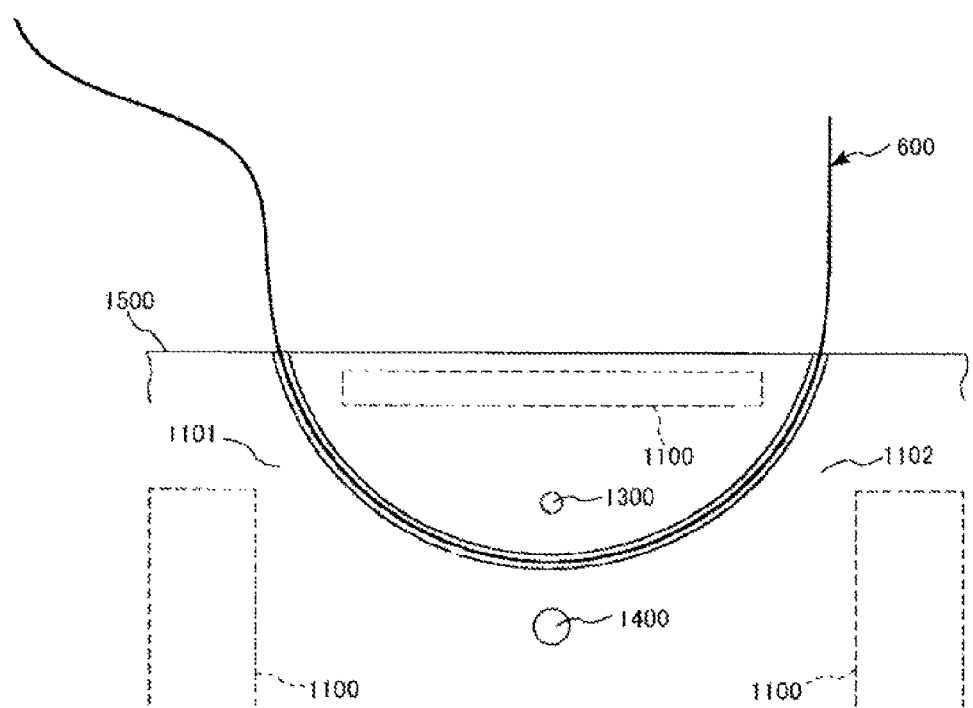
FIG. 37 is a view illustrating the operation procedure of the puncture device (sixth embodiment) of the present disclosure.

Then, a distal end portion of the guide wire 600 is gripped by one hand and kept gripped while the flange portion 304 of the outer tube 30 is gripped by the other hand to pull the flange portion 304 in a direction toward the proximal end. Consequently, the outer tube 30 is pulled out from the puncture hole while the guide wire 600 remains inserted in the puncture hole as depicted in FIG. 37.

Then, an implant assembly 100 is prepared. Then, in the state in which the proximal end portion of the guide wire 600 is inserted in the distal end opening 201 of the medical tube 20, the implant assembly 100 is pushed to advance in a direction toward the distal end with respect to the guide wire 600, as depicted in FIG. 38. Consequently, the implant assembly 100 is fitted in the puncture hole and placed into a state in which it projects at a portion thereof on the distal end side from the obturator foramen 1102 side of the body surface 1500 and projects at a portion thereof on the proximal end side from the obturator foramen 1101 side of the body surface 1500. Thereafter, the guide wire 600 is pulled out from the implant assembly 100.

Thereafter, the medical tube 20 is drawn from the both sides thereof as depicted in FIG. 39. Consequently, the medical tube 20 is separated at the separation portion 2035 into the first tube 2033 and the second tube 2034.

Figure 40:
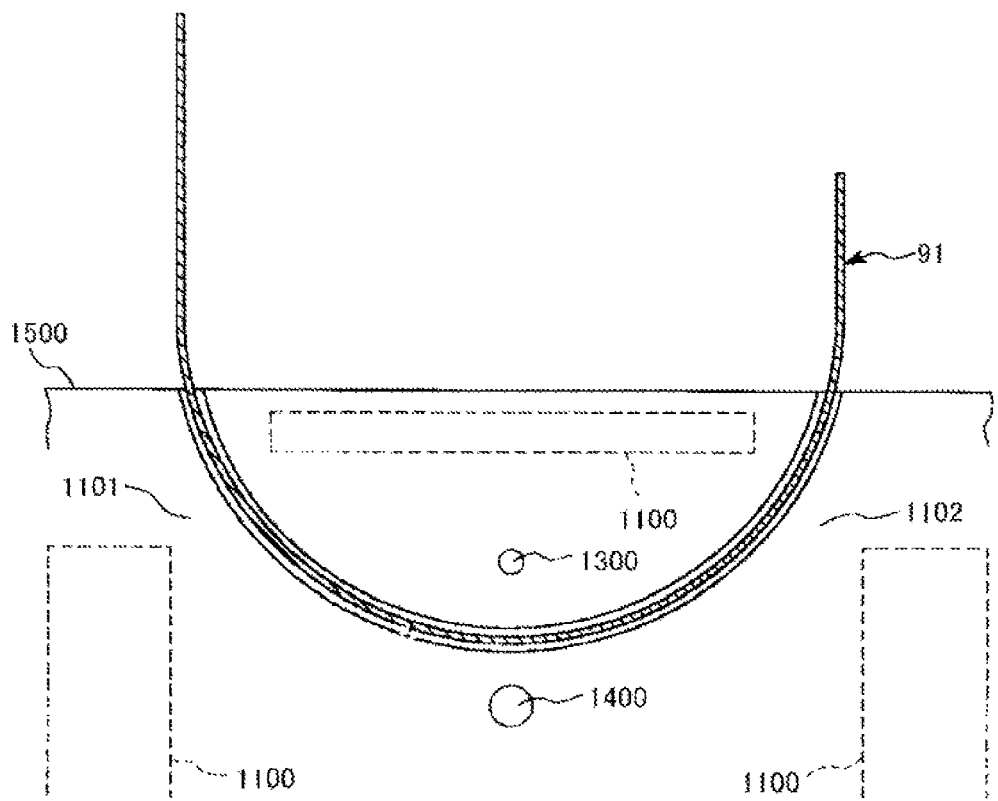
FIG. 40 is a view illustrating the operation procedure of the puncture device (sixth embodiment) of the present disclosure.

Then, the first tube 2033 and the second tube 2034 are pulled out from the puncture hole. Thereupon, the implant main body 91 remains threaded in the puncture hole as depicted in FIG. 40. In accordance with an exemplary embodiment, an unnecessary portion of the implant main body 91 is cut away, thereby ending the manipulation.

It is to be noted that, if the puncture needle 31 has a lumen over the overall length thereof and the removable needle tip 35 is installed at the distal end of the puncture needle 31, then the outer tube 30 described hereinabove can be omitted. In accordance with an exemplary embodiment, for example, after the puncture needle 31 is manipulated to puncture as described hereinabove, the needle tip 35 is removed and the guide wire is inserted into the lumen of the puncture needle 31. After the distal end of the guide wire is projected from one end of the puncture needle 31, the puncture needle 31 is pulled out from the living body. The medical tube 20 is inserted along the guide wire indwelled in the body. Thereafter, a procedure same as that in the present embodiment is followed.

Further, while the present embodiment is described in a mode in which the transverse sectional shape of the outer tube 30 is a flattened shape, the transverse sectional shape of the outer tube 30 may be a circular sectional shape. In this case, the medical tube 20, which has a flattened transverse sectional shape, can be inserted along the guide wire threaded to the body surface passing between the urethra 1300 and the vagina 1400 from the body surface. Although the through-hole of a circular cross section is closed, in a state in which the guide wire is threaded therein, by the pressure of the surrounding tissue, it is expanded to its original circular shape when the medical tube 20 is inserted. As a further mode, the through-hole of a circular cross section extends from the body surface to the body surface passing between the urethra 1300 and the vagina 1400. The medical tube 20 of a flattened shape having a width substantially equal to that of the implant main body 91 can be inserted along the guide wire threaded along the flattened through-hole narrower than the width of the implant main body 91. Although the medical tube described in the description of the present embodiment can be used as the medical tube 20, as a medical tube of another mode, a medical tube can be used which is deformable to an indwelled shape of the guide wire and has a structure which resists against a twist in a circumferential direction around an axis and whose internal space is not crushed by the pressure of the surrounding tissue. According to this mode, while it is ready flexibly for the indwelled shape of the guide wire, a through-hole in the tissue can be formed in parallel to the urethra 1300 by the flattened medical tube 20.

In the following, the seventh embodiment of the puncture device of the present disclosure is described with reference to FIGS. 41 to 46. However, description is given principally of differences from the embodiment described hereinabove, and description of similar matters is omitted herein.

The present embodiment is similar to the first embodiment described hereinabove except that it further can include a sheath.

As depicted in FIGS. 41 to 44, the puncture device 1 further can include a sheath (outer pipe) 70. In the present puncture device 1, the puncture device 1 can assume two states: a first state in which the puncture needle 31 is not inserted in a sheath 70 as yet, or the puncture needle 31 is pulled out from the sheath 70; and a second state (assembled state) in which the puncture needle 31 is inserted in and assembled to the sheath 70.

Figure 41:
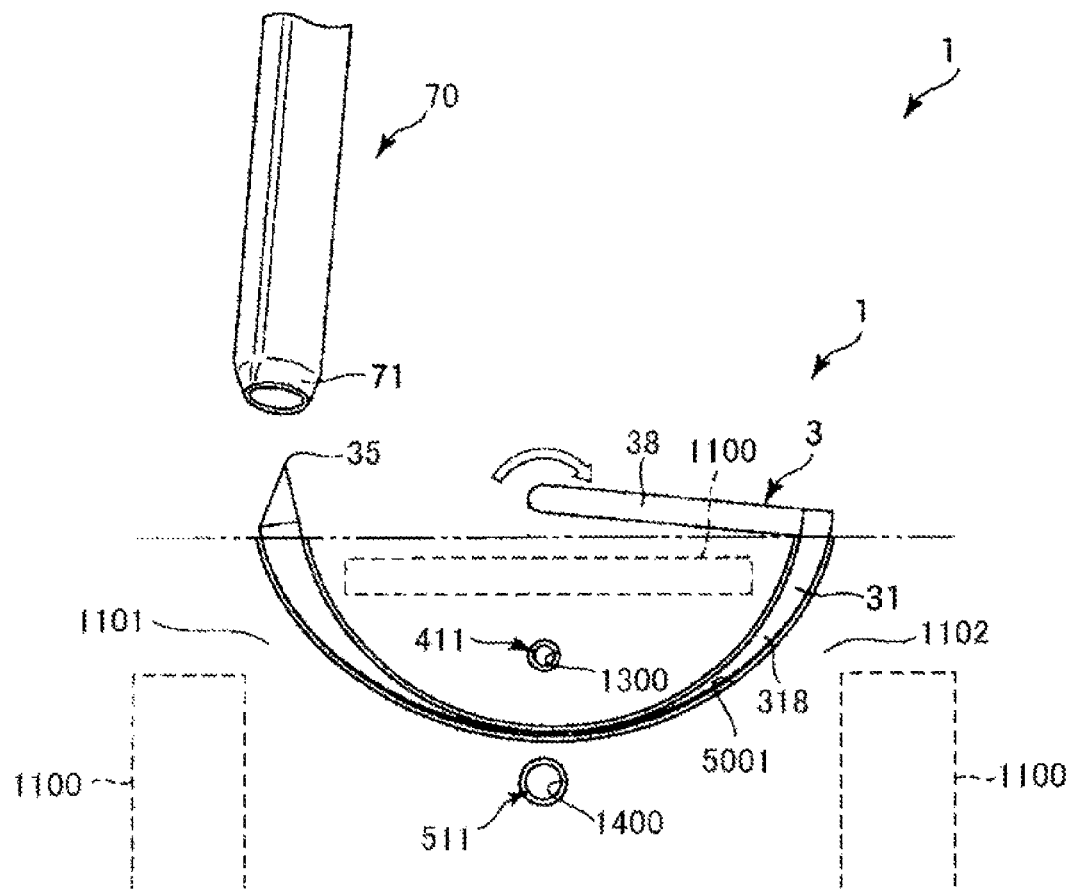
FIG. 41 is a view illustrating an operation procedure of a puncture device (seventh embodiment) of the present disclosure.
Figure 42:
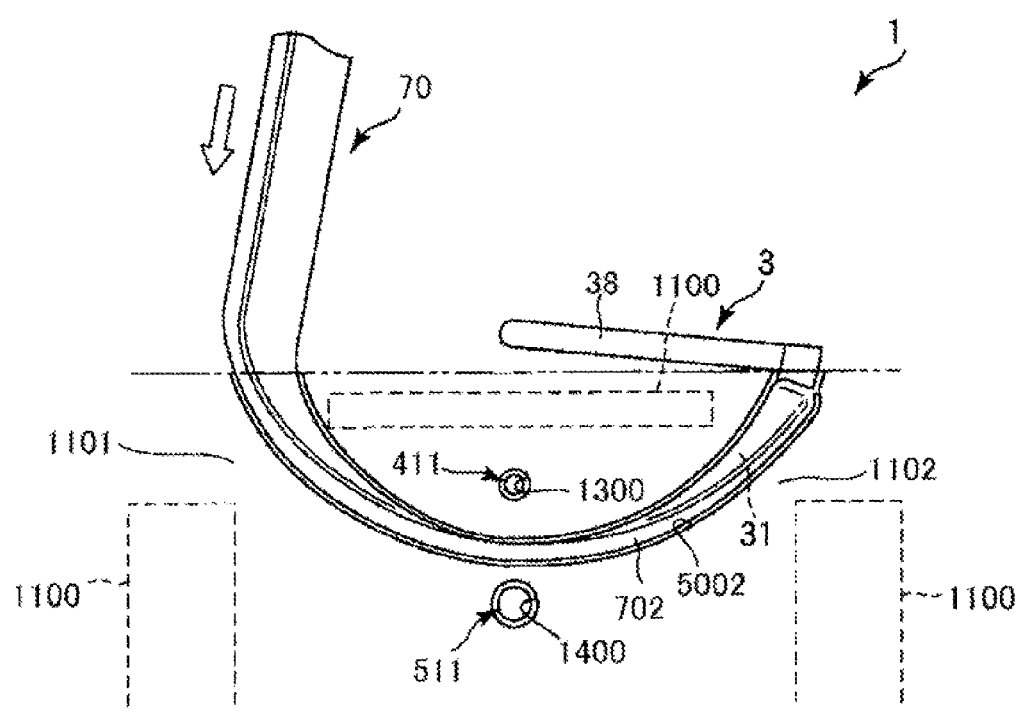
FIG. 42 is a view illustrating the operation procedure of the puncture device (seventh embodiment) of the present disclosure.

The puncture needle 31 punctures the living body in the first state to form a primary puncture hole 5001 in the living body (refer to FIG. 41), and the sheath 70 passes the primary puncture hole 5001 in the second state to change the primary puncture hole 5001 into a secondary puncture hole 5002 (refer to FIG. 42). It is to be noted that the direction in which the puncture needle 31 punctures the living body in the present embodiment is the opposite direction to that in the first embodiment described hereinabove.

As described hereinabove, the transverse sectional shape of the puncture needle 31 is a flattened shape. The flattened portion having the flattened shape is formed over the overall range of the puncture needle 31 in the longitudinal direction, for example, over the overall length of the puncture needle 31, and functions as a puncture needle side expansion portion 318 which forms, when the puncture needle 31 forms the primary puncture hole 5001, so that the primary puncture hole 5001 has a width expanded to a degree similar to that of the implant main body 91 (main body portion 911).

Also the transverse sectional shape of the sheath 70 is a flattened shape similarly to that of the puncture needle 31. The flattened portion having the flattened shape functions as a portion which forms, when the sheath 70 forms the secondary puncture hole 5002, the secondary puncture hole 5002 so as to maintain the expanded state of the primary puncture hole 5001, which has been expanded by the puncture needle side expansion portion 318, with certainty, for example, to form the secondary puncture hole 5002 as an expanded secondary puncture hole expanded with certainty to a similar degree to the width of an outer pipe side expansion portion 702 and the implant main body 91 of the implant 9.

If the implant main body 91 is threaded in the secondary puncture hole 5002 formed in this manner, then the implant main body 91 is prevented from being contracted in the widthwise direction and is placed into a sufficiently developed state. Thus, the implant main body 91 is indwelled stably (refer to FIG. 46). Consequently, the urethra 1300 can be supported sufficiently from the vagina 1400 side, and therefore, the medical treatment of female urinary incontinence can be carried out with relative certainty.

Further, in the second state, the puncture needle side expansion portion 318 of the puncture needle 31 having a flattened transverse sectional shape and the outer pipe side expansion portion 702 of the sheath 70 having a flattened transverse sectional shape overlap with each other. In this manner, in the puncture device 1, since the portions having a flattened transverse sectional shape overlap with each other, a function as a rotation restriction portion for restricting rotation of the sheath 70 is exhibited. Thus, by the rotation restriction portion, the sheath 70 is restricted against rotation around the center axis thereof with respect to the puncture needle 31. Consequently, also the expansion direction of the secondary puncture hole 5002 becomes a same direction as the expansion direction of the primary puncture hole 5001, and therefore, the secondary puncture hole 5002 of such a degree that the implant main body 91 can be expanded sufficiently can be formed with certainty.

Figure 44:
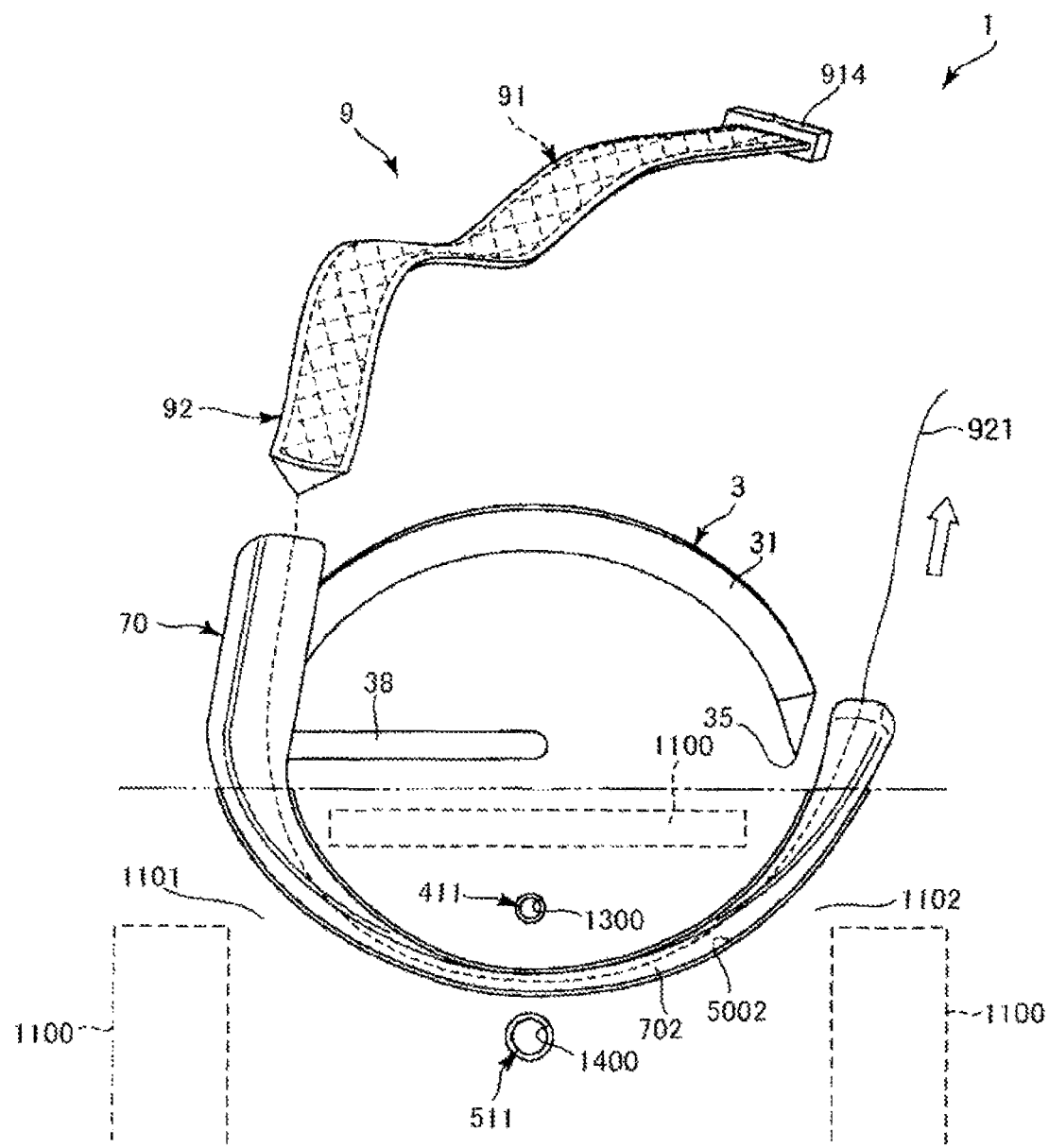
FIG. 44 is a view illustrating the operation procedure of the puncture device (seventh embodiment) of the present disclosure.

As depicted in FIG. 44, the implant main body 91 of the implant 9 has a stopper 914 fixed to one end portion of the main body 91 of the implant. Meanwhile, the packaging material 92 has a string 921 fixed to the both side thereof to the stopper 914 side. In accordance with an exemplary embodiment, it is only necessary for the string 921 to be configured such that it can be threaded in the sheath 70, and, for example, a guide wire configured from, for example, a nickel titanium alloy, or a rope may be used. Further, in the implant 9, the string 921 may be replaced by a strip-like member.

Now, an operation procedure of the puncture device 1 of the present embodiment is described.

First, the puncture device 1 is placed into a mounted state similarly as in the first embodiment described hereinabove. In this state, the puncture device 1 assumes the first state.

Then, the puncture needle 31 is turned in the clockwise direction as depicted in FIG. 41. Consequently, the needle tip 35 of the puncture needle 31 moves in the clockwise direction in FIG. 41 along the arc thereof, and passes through the obturator foramen 1102, a region between the urethra 1300 and the vagina 1400 and through the obturator foramen 1101 of the patient in order and then projects to the outside of the body. Consequently, a primary puncture hole 5001, which passes through the obturator foramen 1102, a region between the urethra 1300 and the vagina 1400 and through the obturator foramen 1101, is formed in the patient. As described hereinabove, the primary puncture hole 5001 is a through-hole expanded to a degree similar to the width of the implant main body 91 of the implant 9.

Then, as depicted in FIG. 42, a sheath 70 is prepared, and the sheath 70 is caused to extend along the puncture needle 31, which remains threaded in the primary puncture hole 5001, and is pushed into the primary puncture hole 5001 from the proximal end side. Consequently, the sheath 70 passes the primary puncture hole 5001 while it is being placed into the second state, and by the passage, the primary puncture hole 5001 changes into the secondary puncture hole 5002. As described hereinabove, the secondary puncture hole 5002 is a through-hole by which the expanded state of the primary puncture hole 5001 is maintained with certainty.

Figure 43:
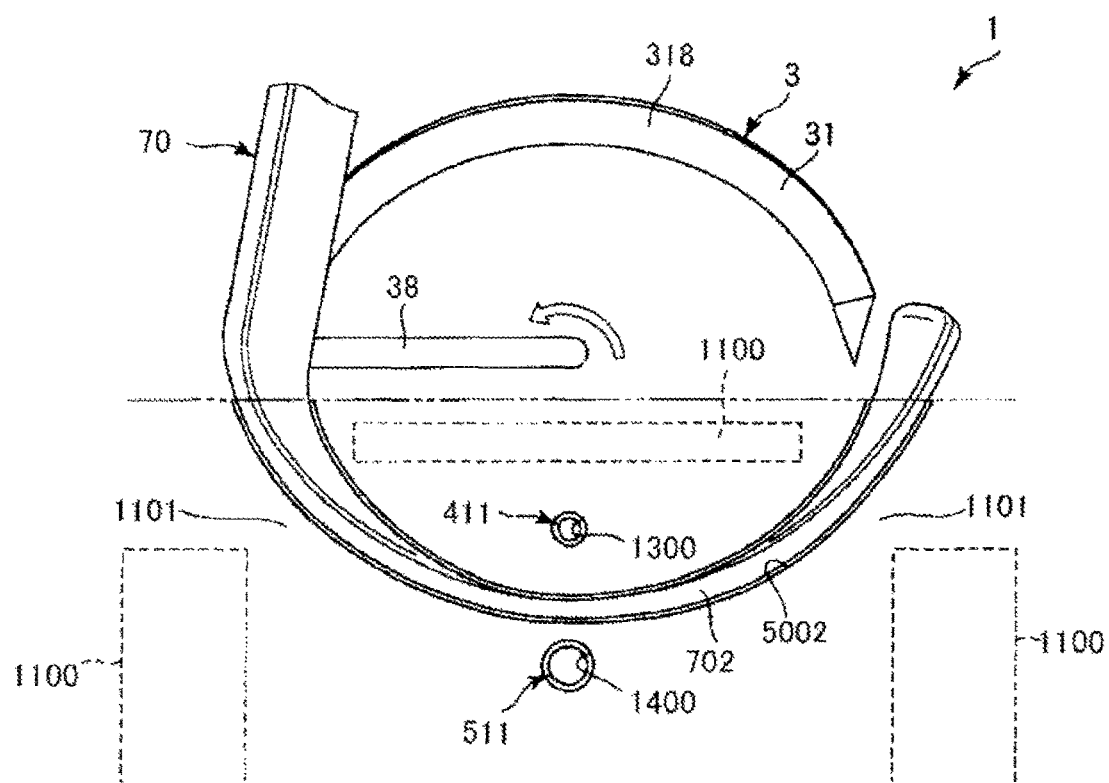
FIG. 43 is a view illustrating the operation procedure of the puncture device (seventh embodiment) of the present disclosure.

Then, while the sheath 70 remains in the secondary puncture hole 5002, the puncture needle 31 is turned in the counterclockwise direction as depicted in FIG. 43. The puncture needle 31 is pulled out to the outside of the body thereby.

Thereafter, the string 921 of the implant 9 is threaded from one side of the sheath 70 as depicted in FIG. 44. Consequently, the string 921 projects from the other end side of the sheath 70. Then, the projected string 921 is gripped and drawn. Consequently, the implant 9 passes, at the portion at which the implant main body 91 exists, through the sheath 70.

Figure 45:
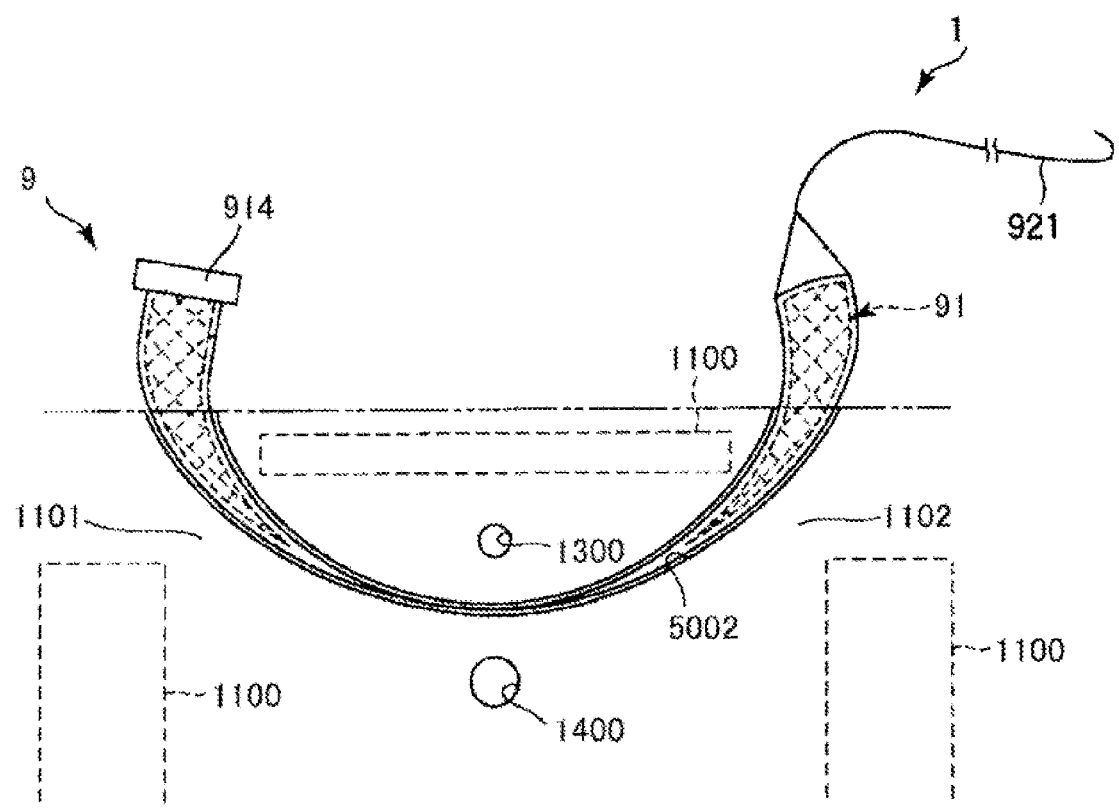
FIG. 45 is a view illustrating the operation procedure of the puncture device (seventh embodiment) of the present disclosure.

Then, while the implant 9 remains in the secondary puncture hole 5002, the sheath 70 is pulled out from the secondary puncture hole 5002 as depicted in FIG. 45. Further, the puncture device 1 is removed from the patient.

Figure 46:
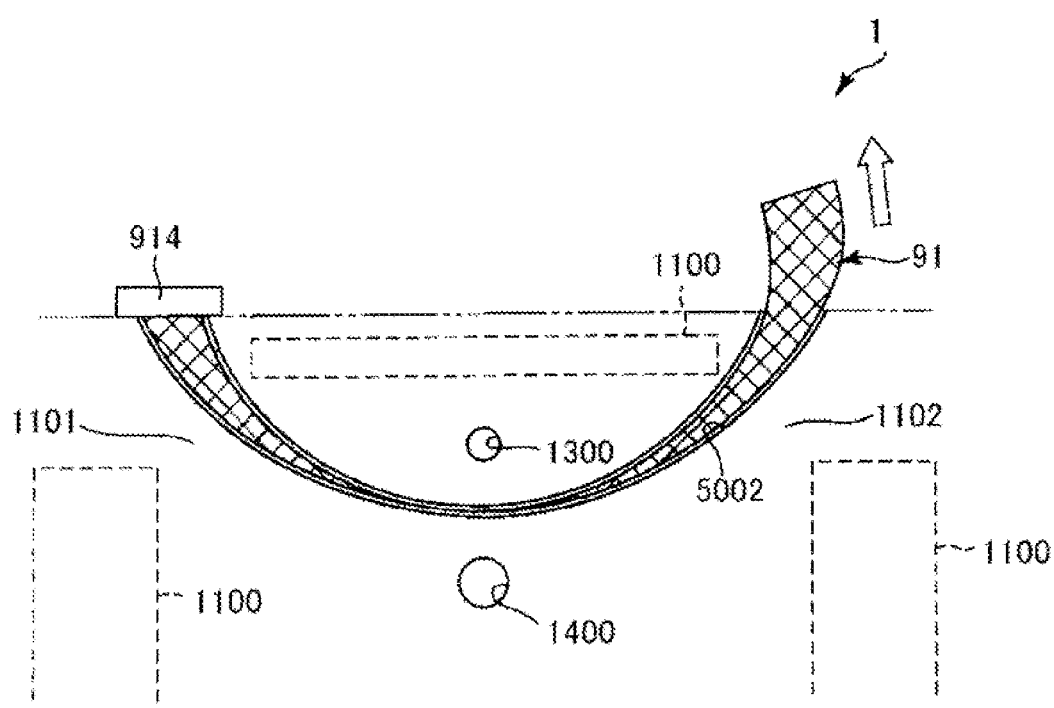
FIG. 46 is a view illustrating the operation procedure of the puncture device (seventh embodiment) of the present disclosure.

Then, the implant 9 is entirely pulled until the stopper 914 is brought into contact with the body surface as depicted in FIG. 46. Thereafter, while the implant main body 91 remains in the secondary puncture hole 5002, the packaging material 92 is drawn. Consequently, the packaging material 92 is pulled out from the secondary puncture hole 5002 while the implant main body 91 is indwelled in the secondary puncture hole 5002. Thereafter, an unnecessary portion of the implant main body 91 is cut away, thereby ending the manipulation.

In the following, the eighth embodiment of the puncture device of the present disclosure is described with reference to FIGS. 47 to 49. However, description is given principally of differences from the embodiment described hereinabove, and description of similar matters is omitted herein.

The present embodiment is similar to the seventh embodiment described hereinabove except that it is different in configuration of the puncture member.

Figure 47:
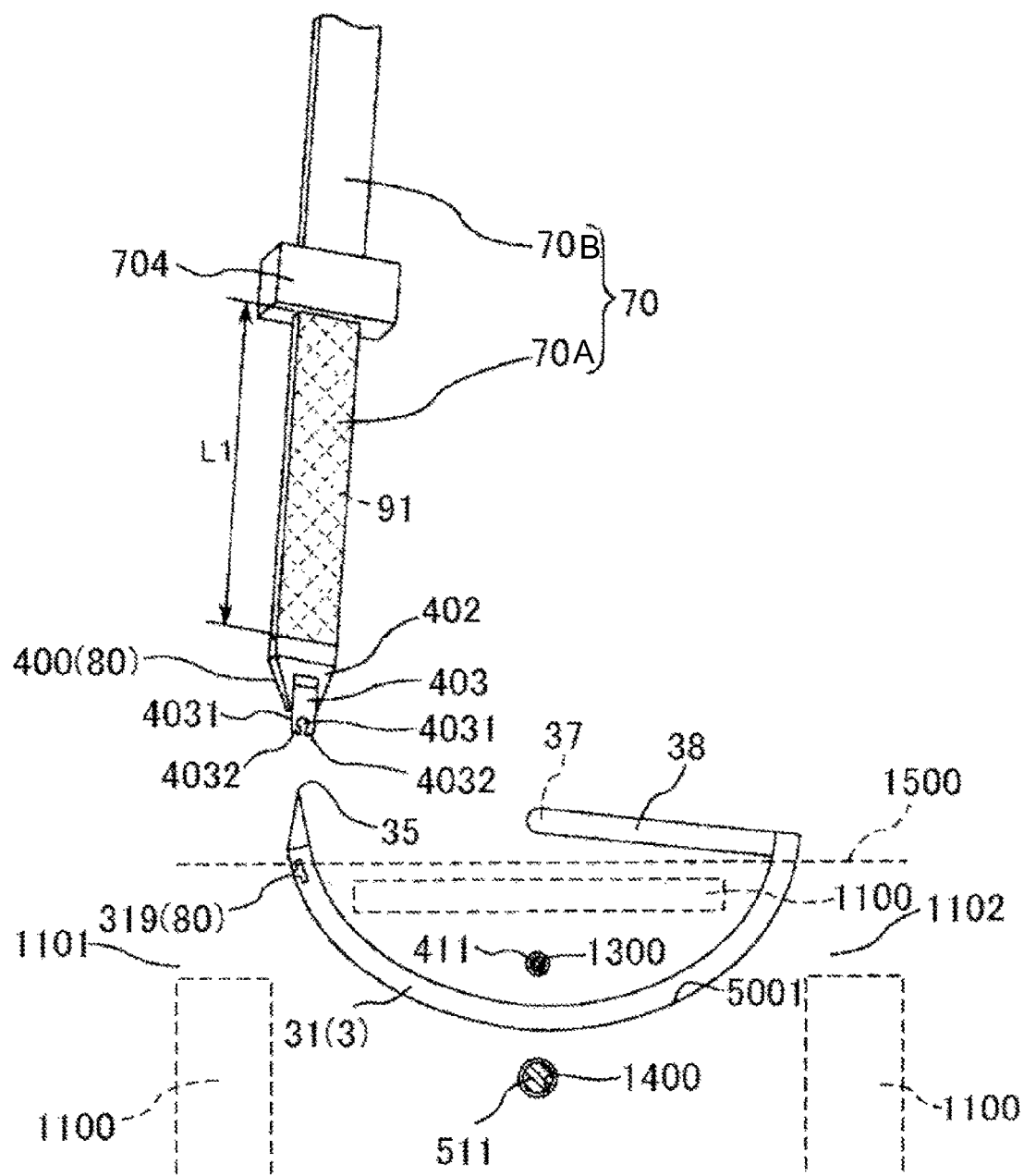
FIG. 47 is a view illustrating an operation procedure of a puncture device (eighth embodiment) of the present disclosure.
Figure 48:
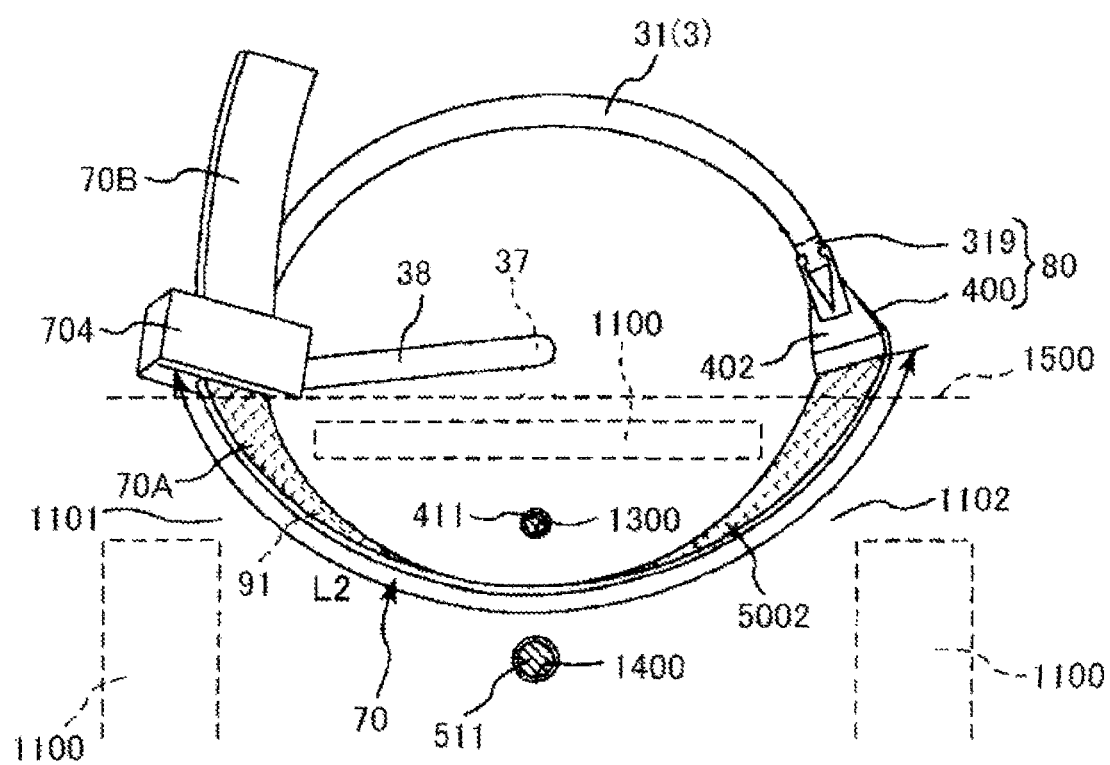
FIG. 48 is a view illustrating the operation procedure of the puncture device (eighth embodiment) of the present disclosure.
Figure 49:
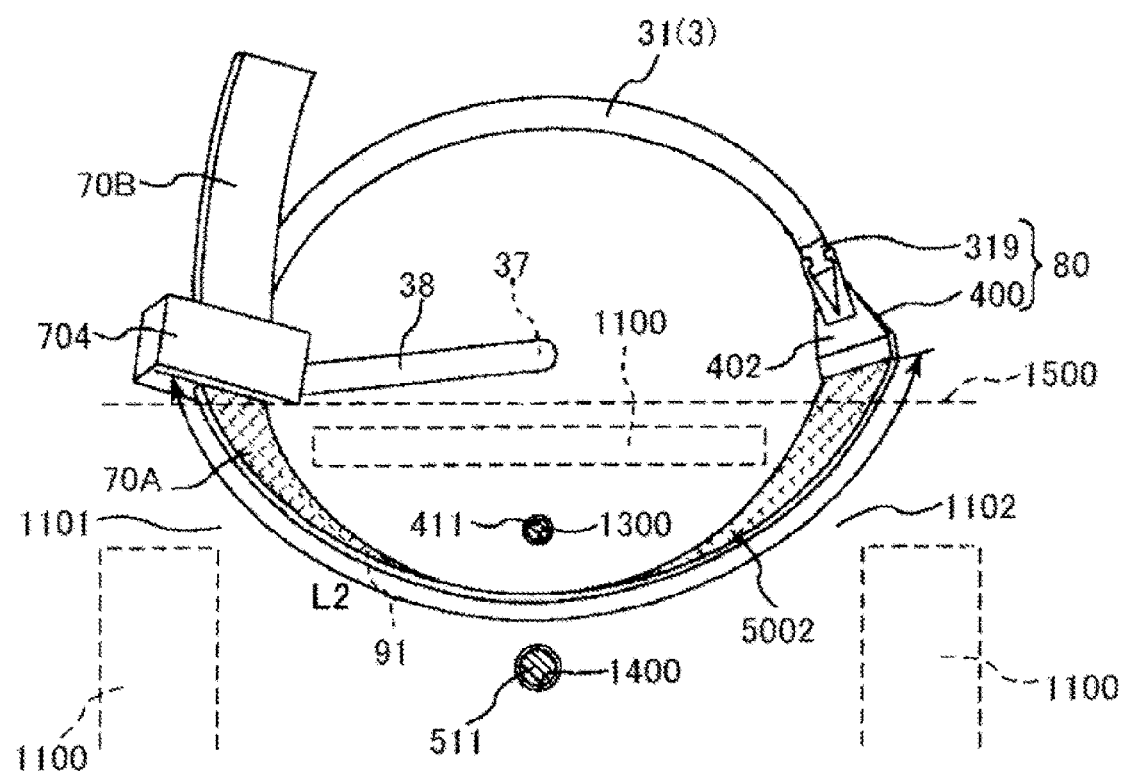
FIG. 49 is a view illustrating the operation procedure of the puncture device (eighth embodiment) of the present disclosure.

As depicted in FIGS. 47 to 49, in the present embodiment, the sheath 70 is configured from an inner pipe 70A and an outer pipe 70B in which the inner pipe 70A is inserted, and the inner pipe 70A and the outer pipe 70B form a double tube structure in which they can move relative to each other. Consequently, the sheath 70 is configured variable in response to the length of the primary puncture hole 5001. It is to be noted that the implant main body 91 is accommodated in advance in the sheath 70.

Further, a flange portion 704 having an expanded outer diameter is formed at a distal end portion of the outer pipe 70B. The flange portion 704 functions as a stopper, which is contacted with the body surface 1500 to restrict a movement limit of the outer pipe 70B (refer to FIG. 48). Consequently, the outer pipe 70B is inhibited from being inserted into the living body together with the inner pipe 70A.

As depicted in FIG. 47, in an initial state in which the sheath 70 is not inserted in the living body as of yet, the length by which the inner pipe 70A projects from the outer pipe 70B is L1. If the inner pipe 70A is connected to the puncture needle 31 and the puncture needle 31 is turned from the initial state, then the flange portion 704 is brought into contact with the body surface 1500. If the puncture needle 31 is turned further, then the inner pipe 70A moves relative to the outer pipe 70B and the length over which the inner pipe 70A projects from the outer pipe 70B becomes L2 which is longer than L1 (refer to FIG. 48). Consequently, when embedding of the inner pipe 70A is completed, the proximal end portion of the inner pipe 70A can be prevented from entering the living body.

When the inner pipe 70A is to be pulled out from the living body, the inner pipe 70A can be cut at a distal end portion thereof and pulled out toward the proximal end side as depicted in FIG. 49. The implant main body 91 can be indwelled in the living body.

Further, in the present embodiment, a connection portion 80 for connecting the inner pipe 70A of the sheath 70 and the puncture needle 31 to each other is provided. The connection portion 80 is configured from a connector 400 on the inner pipe 70A side and a recessed portion 319 on the inner pipe 70A side.

The connector 400 has a projecting piece 403. The projecting piece 403 has a form of a plate and has a pair of arm portions 4031 having elasticity. The arm portions 4031 are provided in parallel along an upward and downward direction in FIG. 10. Further, claws 4032 are formed at a proximal end portion of the arm portions 4031 such that they are opposed to each other and project to the inner side. Besides, in the connection state in which the connector 400 and the recessed portion 319 are connected to each other, the projecting piece 403 is held from the both face sides thereof in the recessed portion 319. Consequently, rotation of the connector 400 around the axis with respect to the puncture needle 31 is stopped and restricted so that the direction in which the peeling off portion 402 hereinafter described peels off the living body tissue may be fixed with respect to the urethral insertion member 4 or the vaginal insertion member 5 (restriction mechanism). Therefore, the implant main body 91 can be suitably embedded so that the direction of the implant main body 91 may be fixed with respect to the urethral insertion member 4 or the vaginal insertion member 5.

Further, the connector 400 has a peeling off portion 402. When the puncture needle 31 turns in the direction opposite to the puncture direction to form the secondary puncture hole 5002 while the connector 400 is in the connection state, the peeling off portion 402 peels off the living body tissue upon such turning motion. This peeling off portion 402 supports the projecting piece 403 and has a width, which decreases gradually toward the projecting piece 403 side. Consequently, peeling off for the living body tissue can be carried out with relative certainty.

In the following, the ninth embodiment of the puncture device of the present disclosure is described with reference to FIG. 50. However, description is given principally of differences from the embodiment described hereinabove, and description of similar matters is omitted herein.

The present embodiment is similar to the first embodiment described hereinabove except that it is different in configuration of the puncture needle.

Figure 50:
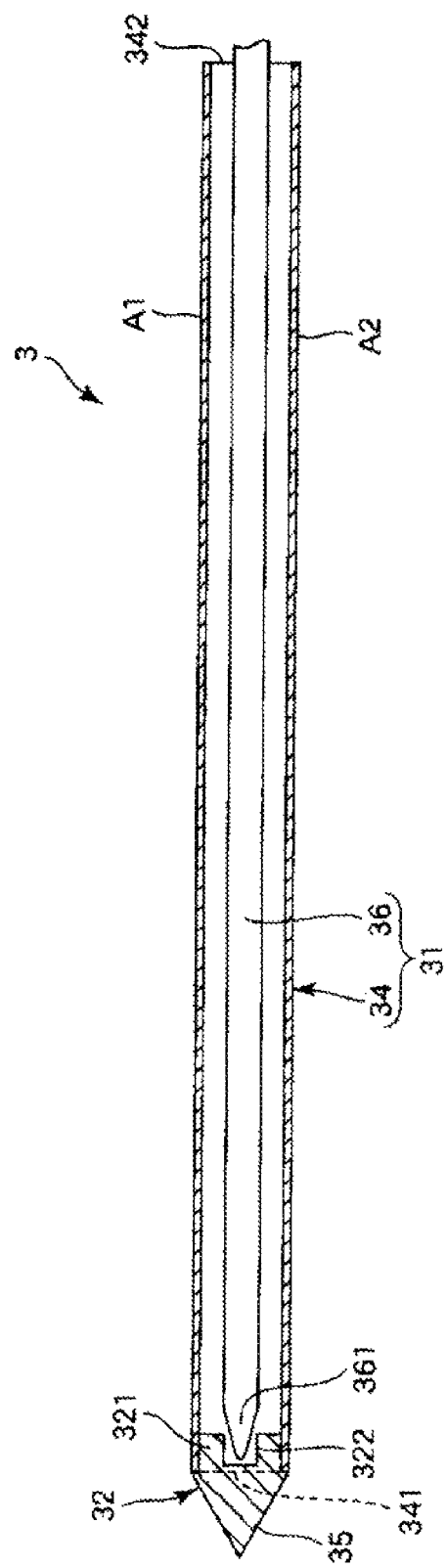
FIG. 50 is a partial vertical sectional view of a yet further puncture device (ninth embodiment) of the present disclosure.

As depicted in FIG. 50, in the present embodiment, the puncture needle 31 is configured from an assembly having a main body portion 34 and an insertion portion 36 inserted in the main body portion 34. The puncture needle 31 can puncture the living body in an assembled state in which the insertion portion 36 is inserted in the main body portion 34.

The main body portion 34 is configured from a pipe body (tube) curved in an arc and has a distal end side opening 341 open at the distal end thereof and a proximal end side opening 342 open at the proximal end thereof. Such a main body portion 34 as just described has an internal space into which the implant main body 91 can be inserted. Further, the main body portion 34 has a transverse sectional shape of a flattened shape similarly to the puncture needle 31 in the first embodiment described hereinabove. Consequently, the posture of the implant main body 91 in the main body portion 34 can be controlled. Further, the width of the internal space of the main body portion 34 is designed substantially equal to the width of the main body portion 911 of the implant main body 91. Consequently, even if the implant main body 91 is moved, the frictional resistance by the internal space of the main body portion 34 is low, and unnecessary force is not applied to the implant main body 91. Consequently, the main body portion 911 can be disposed in a sufficiently developed state in the main body portion 34.

A needle body 32 is removably provided in the distal end side opening 341 of the main body portion 34. The needle body 32 has a tapering needle tip 35 and a proximal end portion 321 provided on the proximal end side of the needle tip 35. Further, the proximal end portion 321 is inserted in the main body portion 34, and the needle body 32 is removably held in the main body portion 34. It is to be noted that the proximal end portion 321 is fitted in the main body portion 34 by such a degree of force that unintended removal of the needle body 32 from the main body portion 34 can be prevented. It is to be noted that the needle body 32 may be configured integrally with the main body portion 34.

Further, an engaging portion 322 is provided on the proximal end portion 321 such that it engages with a distal end portion 361 of the insertion portion 36. The engaging portion 322 is configured from a recessed portion, and in an assembled state, the distal end portion 361 is positioned in the engaging portion 322. By the provision of the engaging portion 322, displacement of the needle body 32 with respect to the insertion portion 36 is suppressed, and puncture into the living body can be carried out relatively smoothly.

The insertion portion 36 is a portion to be inserted into the main body portion 34 and functions as a stylet, which reinforces the main body portion 34 from the inner side. The insertion portion 36 has an arcuate shape corresponding to the shape of the main body portion 34. The central angle of the insertion portion 36 is set in accordance with the central angle of the puncture member 3. Further, the distal end portion 361 of the insertion portion 36 has a tapering shape. Since the insertion portion 36 has the tapering distal end portion 361, insertion of the insertion portion 36 into the main body portion 34 can be carried out relatively smoothly.

In the puncture needle 31 having such a configuration as described above, by operating, after the puncture needle 31 in the assembled state punctures the living body tissue, the puncture needle 31 in the opposite direction so as to retreat, the main body portion 34 remains in the living body together with the needle body 32 while only the insertion portion 36 is pulled out. Then, the needle body 32 can be released from the main body portion 34 and the implant main body 91 can be threaded into the main body portion 34. Thereafter, by drawing only the main body portion 34 while the implant main body 91 is supported, the implant main body 91 is indwelled into the living body, and an unnecessary portion of the implant main body 91 is cut away, thereby ending the manipulation.

While the puncture device of the present disclosure has been described in connection with the embodiments depicted in the drawings, the present disclosure is not limited to them, and the components of the puncture device can be replaced by elements of an arbitrary configuration which can exhibit similar functions. Further, the puncture device may have an arbitrary component added thereto.

Further, the puncture device of the present disclosure may be a combination of two or more arbitrary ones of the components (features) of the embodiments described hereinabove.

Further, while it is described in the foregoing description of the embodiments that the puncture device of the present disclosure is applied to an apparatus which is used to embed an implant, which can be embedded for the treatment of female urinary incontinence, into the living body, the application of the puncture device of the present disclosure is not limited to this.

For example, the present disclosure has an application target including excretion failure (such as urinary urgency, frequent urination, urinary incontinence, fecal incontinence, urinary retention and difficulty in urination), pelvic floor disorders including pelvic organ prolapse, vesicovaginal fistula, urethra vaginal fistula, and pelvic pain, which can be caused by weakening of the pelvic floor muscles. The pelvic organ prolapse can include such diseases as cystocele, enterocele, rectocele, and uterine prolapse. The pelvic organ prolapse further can include such diseases as forward vaginal wall prolapse, rearward vaginal wall prolapse, vaginal vault prolapse, and vaginal vault part prolapse which are ways to call classified depending upon the prolapsed vaginal wall region.

Further, the hypermobility organizations include the bladder, the vagina, the uterus, and intestines. The fine-moving organizations include bones, muscles, fascias, and ligaments. For example, the pelvic floor disorders can include obturator fasciae, coccyx fasciae, ligamentum cardinale, sacrum uterus ligaments, and sacrospinous ligaments.

The manipulations for connecting a hypermobility organization to a fine-moving organization in pelvic floor diseases include a retropubic sling surgery, a transobturator sling surgery (i.e. transobturator tape; TOT), a transvaginal mesh surgery (Tension-free Vaginal Mesh; TVM), a uterosacral ligament suspension (USLS) which utilizes sacrum uterus ligaments, a fixation (Sacrospinous Ligament Fixation; SSLF) which utilizes sacrospinous ligaments, a fixation which utilizes iliococcygeus fascias, a fixation which utilizes coccyx fascias and so forth.

The puncture device of the present disclosure can include a puncture needle curved in an arc, turnably supported around a turning center provided by the center of the arc and having a needle tip which punctures a living body when the puncture needle is turned, and an insertion member having a linear portion of a linear shape at least at part thereof, the linear portion being inserted into the urethra or the vagina. The locus of the needle tip when the puncture needle is turned is inclined with respect to a plane orthogonal to the linear portion. Therefore, when, for example, an implant is to be indwelled into the living body, the implant can be indwelled stably.

Accordingly, the puncture device of the present disclosure has an industrial applicability.

The detailed description above describes a puncture device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A puncture device, comprising:
    a puncture needle curved in an arc and turnably supported around a turning center provided by a center of the arc, the puncture needle having a needle tip configured to puncture a living body when the puncture needle is turned; and
    an insertion member having a linear portion of a linear shape at least at part of the insertion member, the linear portion being configured to be inserted into a urethra or a vagina, wherein
    when the puncture needle is turned, the needle tip enters the living body from one inguinal region, passes between the urethra and the vagina in a plane with an inclination angle with respect to a plane orthogonal to the linear portion, and exits the living body from an other inguinal region on an opposite side of the living body.

2. The puncture device according to claim 1, wherein the inclination angle is about 20 to 60 degrees.

3. The puncture device according to claim 1, comprising:
    a supporting member configured to turnably support the puncture needle; and
    wherein the puncture needle and the insertion member are connectable to each other.

4. The puncture device according to claim 3, wherein
    the insertion member is configured to be inserted into the urethra, and
    the supporting member is configured to regulate a positional relationship between the puncture needle and the insertion member such that, when the puncture needle turns to puncture the living body, the needle tip passes a farther side from the turning center of the puncture needle than the insertion member.

5. The puncture device according to claim 3, wherein the insertion member comprises a urethral insertion member configured to be inserted into the urethra and a vaginal insertion member configured to be inserted into the vagina, and
    the supporting member is configured to regulate a positional relationship between the puncture needle and the vaginal insertion member such that, when the puncture needle turns to puncture a tissue of the living body, the needle tip does not interfere with the vaginal insertion member.

6. The puncture device according to claim 1, wherein the puncture needle has a flattened transverse sectional shape in a longitudinal direction of at least a portion of the puncture needle, the longitudinal direction being in a direction of a curvature of the arc of the puncture needle.

7. The puncture device according to claim 6, wherein, in a state in which the puncture needle punctures the living body, the flattened portion transverse sectional shape of the puncture needle is positioned between the urethra and the vagina, the longitudinal axis of the flattened transverse sectional shape being directed substantially in parallel to the urethra.

8. The puncture device according to claim 1, wherein
the puncture needle has a portion configured from a hollow body, the hollow body accommodating therein an implant having flexibility and having an elongated shape.

9. The puncture device according to claim 1, wherein
the puncture needle has a through-hole in proximity of the needle tip, the through-hole being engageable with an implant having flexibility and having an elongated shape.

10. The puncture device according to claim 1, comprising:
a medical tube into which an elongated implant is inserted, wherein the medical tube is configured from a tube open at both ends of the tube;
the medical tube having a curved portion in which at least midway of the medical tube in a longitudinal direction is curved in an arc, the curved portion maintaining the curved arc state; and
the medical tube is used after the puncture needle is turned.

11. The puncture device according to claim 1, wherein
the puncture needle has a needle main body and an extension needle having the needle tip provided thereon, the extension needle being provided for relative movement with respect to the needle main body along a longitudinal direction of the needle main body; and
the puncture device further comprises a pusher for pushing the extension needle in a direction toward a distal end of the needle main body with respect to the needle main body to extend the puncture needle.

12. The puncture device according to claim 1, comprising:
a support member movably supports the puncture needle and supports the insertion member; and
a peeling off portion configured to peel off the living body tissue on an inner side of the living body in accordance with a turning movement of the puncture needle when the puncture needle is turned; and
a restriction mechanism for restricting a direction in which the peeling portion peels off the living body tissue, the direction being fixed with respect to the insertion member.

13. The puncture device according to claim 1, comprising:
an implant, which is indwelled between the urethra and the vagina for use for medical treatment of a disease of pelvic viscera.

14. A method of forming a path in living body tissue, the method comprising:
inserting an insertion member into a urethra or a vagina, the insertion member having a linear portion of a linear shape at least at part of the insertion member;
puncturing the living body with a puncture needle, the puncture needle being curved in an arc and turnably supported around a turning center provided by a center of the arc, the puncture needle having a needle tip configured to puncture the living body when the puncture needle is turned; and
turning the puncture needle such that the needle tip enters the living body tissue from one inguinal region, passes between the urethra and the vagina in a plane with an inclination angle with respect to a plane orthogonal to the linear portion, and exits the living body from an other inguinal region on an opposite side of the living body.

15. The method according to claim 14, comprising:
regulating a positional relationship between the puncture needle and the insertion member such that, when the puncture needle turns to puncture the living body, the needle tip passes a farther side from the turning center of the puncture needle than the insertion member.

16. The method according to claim 15, wherein the insertion member comprises a urethral insertion member configured to be inserted into the urethra and a vaginal insertion member configured to be inserted into the vagina, the method further comprising:
regulating a positional relationship between the puncture needle and the vaginal insertion member such that, when the puncture needle turns to puncture a tissue of the living body, the needle tip does not interfere with the urethral insertion member and the vaginal insertion member.

* * * * *